(12) United States Patent
Florkiewicz et al.

(10) Patent No.: US 6,306,613 B1
(45) Date of Patent: *Oct. 23, 2001

(54) MODULATORS OF LEADERLESS PROTEIN EXPORT AND METHODS FOR IDENTIFYING AND USING THE SAME

(75) Inventors: Robert Z. Florkiewicz, Ramona; Andrew Baird; Dale E. Warnock, both of San Diego, all of CA (US)

(73) Assignee: Ciblex Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/451,905

(22) Filed: Dec. 1, 1999

Related U.S. Application Data

(63) Continuation-in-part of application No. 09/030,613, filed on Feb. 25, 1998, now Pat. No. 6,083,706, which is a continuation-in-part of application No. 08/807,014, filed on Feb. 26, 1997.

(51) Int. Cl.[7] .................. G01N 33/53; A01N 43/04; A01N 45/00; C12N 9/99; C07K 1/00
(52) U.S. Cl. ............... 435/7.1; 435/7.2; 435/184; 514/25; 514/26; 514/27; 514/28; 514/29; 514/30; 514/31; 514/443; 530/351; 530/396; 530/399
(58) Field of Search ................. 435/7.1, 7.2, 184; 514/25, 26, 27, 28, 29, 30, 31, 443; 530/351, 396, 399

(56) References Cited

U.S. PATENT DOCUMENTS

| | | | |
|---|---|---|---|
| 4,975,467 | 12/1990 | Ku et al. | 514/712 |
| 5,545,623 | 8/1996 | Matsumori | 514/26 |
| 6,083,706 | * 7/2000 | Florkiewicz et al. | 435/7.1 |

FOREIGN PATENT DOCUMENTS

| | | |
|---|---|---|
| WO 92/16226 | 10/1992 | (WO) . |
| WO 93/09135 | 5/1993 | (WO) . |
| WO 96/04921 | 2/1996 | (WO) . |
| WO 97/28808 | 8/1997 | (WO) . |

OTHER PUBLICATIONS

Barinaga, "A Shared Strategy for Virulence," *Science* 272:1261–1263, 1996.

Bost and Belin, "A new genetic selection identifies essential residues in SecG, a component of the *Escherichia coli* protein export machinery," *The EMBO Journal* 14(18):4412–4421, 1995.

DeTomaso et al., "The α and β Subunits of the Na, K–ATPase Can Assemble at the Plasma Membrane into Functional Enzyme," *The Journal of Cell Biology* 127:55–69, 1994.

Florkiewicz et al., "Cardenolides inhibit FGF–2 protein expor: A novel regulatory function for Na+, K+–ATPase," *FASEB Journal* 11(9): No. 1222, p. A1066, 1997.

Florkiewicz et al., "Quantitative Export of FGF–2 Occurs Through an Alternative, Energy–Dependent, Non–ER/Golgi Pathway," *Journal of Cellular Physiology* 162:388–399, 1995.

Florkiewicz et al., "Regulation Of FGF–2 Export By Cardenolides," *Molecular Biology Of The Cell* 7(Suppl.): No. 1080, p. 186a, 1996.

Floriewicz et al., "The Inhibition of Fibroblast Growth Factor–2 Export by Cardenolides Implies a Novel Function for the Catalytic Subunit of Na$^{30}$, K$^+$–ATPase," *The Journal of Biological Chemistry* 273(1):544–551, 1998.

Goldstein, "HIV–1 Tat protein as a potential AIDS vaccine," *Nature Medicine* 1(9):960–964, 1996.

Hamon et al., "Interleukin–1β Secretion Is Impaired by Inhibitors of the Atp Binding Cassette Transporter, ABC1," *Blood* 90(8):2911–2915, 1997.

Harlow et al., *Antibodies: A Laboratory Manual*, pp. 421–466 and 511–551.

Jackson et al., "The Release of Fibroblast Growth Factor–1 from NIH 3T3 Cells in Response to Temperature Involves the Function of Cysteine Residues," *The Journal of Biological Chemistry* 270(1):33–36, 1995.

Jarvis et al., "Enteropathogenic *Escherichia coli* contains a putative type III secretion system necessary for the export of proteins involved in attaching and effacing lesion formation," *Proc. Natl. Acad. Sci. USA* 92:7996–8000, 1995.

Jerse et al., "A genetic locus of enteropathogenic *Escherichia coli* necessary for the production of attaching and effacing lesions on tissue culture cells," *Proc. Natl. Acad. Sci. USA* 87:7839–7843, 1990.

(List continued on next page.)

Primary Examiner—Lynette R. F. Smith
Assistant Examiner—Padma Baskar
(74) Attorney, Agent, or Firm—Seed Intellectual Property Law Group PLLC

(57) ABSTRACT

Methods of modulating the export of a leaderless protein from a cell by contacting the cell with a compound that alters the binding of the leaderless protein and a transport molecule are provided. Transport molecules include gastrin binding protein/alpha subunit of mitochondrial fatty acid β-oxidation multienzyme complex (p70, GenBank Accession Nos. U04627/D16480), phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components. Leaderless proteins include, for example, FGF-1, FGF-2, IL-1α, IL-1β, CNTF, MIF, and HIV tat. These methods are useful in treatment of various conditions, including tumors and diabetes as well is in identifying small molecules for export modulation.

8 Claims, 41 Drawing Sheets

OTHER PUBLICATIONS

Kaelin Jr. et al., "Identification of Cellular Proteins That Can Interact Specifically with the T/E1A–Binding Region of the Retinoblastoma Gene Product," *Cell 64* :521–532, 1991.

Kenny and Finlay, "Protein secretion by enteropathogenic *Escerichia coli* is essential for transducing signals to epthelial cells," *Proc. Natl. Acad. Sci. USA 92*:7991–7995, 1995.

Kent et al., "Ouabain Resistance Conferred by Expression of the cDNA for a Murine $Na^{30}$, $K^{30}$ –ATPase α Subunit," *Science 237*:901–903, 1987.

Levenson, "Isoforms of the Na, K–ATPase: Family Members in Search of Foundation," *Rev. Physiol. Biochem. Pharmacol. 123*:1–45, 1994.

Lewis, "Multidrug resistance pumps in bacteria: variations on a theme," *TIBS 19*:119–124, 1994.

McDaniel et al., "A genetic locus of enterocyte effacement conserved among diverse enterobacterial pathogens," *Proc. Natl. Acad. Sci. USA 92*:1664–1668, 1995.

Mignatti et al., "Basic Fibroblast Growth Factor, a Protein Devoid of Secretory Signal Sequence, Is Released by Cells via a Pathway Independent of the Endoplasmic Reticulum–Golgi Complex," *Journal Of Cellular Physiology 151*:81–93, 1992.

Neyfakh et al., "Efflux–mediated multidrug resistance in *Bacillus subtilis*: Similarities and dissimilarities with the mammalian system," *Proc. Natl. Acad. Sci. USA 88*:4781–4785, 1991.

Nilsson et al., "Fusion Proteins in Biotechnology and Structural Biology," *Current Opinion in Structural Biology 2*:569–575.

Rubartelli et al., "A novel secretory pathway for interleukin–1β, a protein lacking a signal sequence," *The EMBO Journal 9*(5):1503–1510, 1990.

Rubartelli et al., "Secretion of Thioredoxin by Normal and Neoplastic Cells through a Leaderless Secrtory Pathway," *The Journal Of Biological Chemistry 267*(34):24161–24164, 1992.

Russel, "Phage Assembly: A Paradigm for Bacterial Virulence Factor Export," *Science 265*:612–614, 1994.

Salmond and Reeves, "Membrane traffic wardens and protein secretion in Gram–negative bacteria," *TIBS 18*:7–12, 1993.

* cited by examiner

| cat# | molstructure | molename | µM | % Inhibition FGF2 | nM | % Inhibition FGF2 | % Inhibition hCG 50 µM | % Inhibition hCG 50 nM |
|---|---|---|---|---|---|---|---|---|
| 501428 | | N-PHENACYL-N-PHENYLTRIFLUOR OMETHYLSULFON AMIDE | 14.6 | 74 | 145.6 | | 0 | 0 |
| 01800050 | | ATEBRINE | 13.97 | 64 | 139.7 | 22 | 35 | 0 |
| 01800123 | | ECHINOCYSTIC ACID | 10.6 | 63 | 105.8 | | 36 | 16 |
| 01901031 | | N,N¹-DI-(2,4-DIAMINOPHENYLIS OPHTHALAMIDE | 13.3 | 62 | 132.8 | 58 | 9 | 0 |
| 00924321 | | 2-BENZAMIDO-3-CARBOXY-4,5,6,7-TETRAHYDRO BENZ[b]THIOPHEN E | 16.6 | 60 | 165.9 | 11 | 27 | 14 |

Fig. 29A

| cat# | molstructure | molename | μM | % Inhibition FGF2 | nM | % Inhibition FGF2 | % Inhibition hCG 50 μM | % Inhibition hCG 50 nM |
|---|---|---|---|---|---|---|---|---|
| 00926838 | | N,N¹-DI-(4-DIMETHYLAMINOBENZYLIDENE)HYDRAZINE | 17.0 | 60 | 169.8 | 63 | 0 | 7 |
| 922645 | | 6-PENTYLIDENEAMINOPURINE | 24.6 | 59 | 246 | | 0 | 0 |
| 00927210 | | DI-(4-CYCLOHEXYLOXYETHOXYCARBONYL AMINOPHENYL)METHANE | 9.3 | 58 | 92.8 | | 0 | 6 |
| 01100596 | | 2-(t-BUTYLAMINOSULFONYL)-3-PHENYLACRYLIC ACID, ETHYL ESTER | 16.06 | 55 | 160.6 | 0 | ND | ND |

Fig. 29B

| 01100194 |  | 2-BENZYLOXYCARBONYL-5-[(2,2-DIETHOXYCARBONYL)ETHYLIDENYL]PYRROLE | 13.46 | 69 | 134.6 | 0 | ND | ND |

Characterization of
The p62-FGF2 Interaction

Endogenous p62 from COS and HEC-1B binds to
GST-FGF2 (immunoblot analysis)

MODULATORS OF LEADERLESS PROTEIN EXPORT AND METHODS FOR IDENTIFYING AND USING THE SAME

CROSS-REFERENCE TO RELATED APPLICATION

The application is a continuation-in-part of U.S. patent application Ser. No. 09/030,613, filed Feb. 25, 1998, U.S. Pat. No. 6,083,706, which is a continuation-in-part of U.S. patent application Ser. No. 08/807,014, filed Feb. 26, 1997.

TECHNICAL FIELD

The present invention relates generally to leaderless protein export pathway and to modulators of leaderless protein export, and more specifically, to methods of identifying components of the leaderless protein export pathway and compounds that increase or decrease export of leaderless proteins into the extracellular environment.

BACKGROUND OF THE INVENTION

Many proteins exert an effect on cell growth, differentiation, and inflammation through signal transduction, mediated by binding to a cell surface receptor. Yet other proteins, such as factors that initiate or are necessary for blood clot formation, act enzymatically in blood. While these actions are generally part of normal processes, tinder certain circumstances, it may be desirable to limit or inhibit the action of certain proteins and the effects of subsequent signaling. For example, tumor growth that is promoted by a growth factor, such as bFGF acting on melanoma cells, is deleterious and often leads to fatalities.

Approaches to inhibit specific proteins have concentrated primarily on interfering with protein-substrate or protein-receptor interactions. Typically, this involves using an antibody or other molecule that competitively binds the protein, by administration of competitors for receptor binding, or by protease digestion of the protein. An alternative approach, not generally pursued, is to reduce the level of the protein by inhibiting its expression at a transcriptional or translational level. Methods of reducing protein levels by inhibiting the transcription or translation of the protein have been difficult to achieve because of inherent problems of inhibiting the specific expression of one or a few proteins.

The discovery that certain proteins, such as growth factors, mediators of inflammation, and mediators of blood clotting, are exported through a nonclassical secretory pathway allows the development of specific inhibitors for these proteins. These proteins are identified by their lack of a hydrophobic leader sequence that mediates secretion by the classical ER/Golgi pathway.

This invention provides modulators of the export of these leaderless proteins, allowing control of undesired proliferation and inflammation, as well as other related advantages.

SUMMARY OF THE INVENTION

The present invention generally provides methods of modulating the export of a leaderless protein from a cell and of identifying one or more components of a cell transport pathway. In one aspect, methods are provided for decreasing export of a leaderless protein from a cell, by contacting a cell with an effective amount of a modulator, wherein the modulator directly or indirectly prevents formation of or alters the stability of a complex or indirectly alters export, where the complex comprises a leaderless protein and a transport molecule, thereby decreasing export of the leaderless protein from the cell. In certain preferred embodiments, the transport molecule may comprise a gastrin binding protein/alpha subunit of mitochondrial fatty acid β-oxidation multienzyme complex (p70, GenBank Accession Nos. U04627/D16480), a phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components. In certain other embodiments, the cell may be bacterial, yeast, plant, COS-1, BHK, CHO, HeLa, 293, NS-1, HepG2, J744, HEC-1-A, HEC-1-B, 3T3, D10.G4.1, P388$D_1$, 5637, SK-HEP-1, THP-1, Caco-2, MDCK, Jurkat, U87, LnCap, primary tumor biopsies, and tumor derived cell lines. In yet other embodiments, the leaderless protein may be FGF-1, FGF-2, IL-1α, IL-1β, aldose reductase, PD-ECGF, CNTF, prothymosin ax, parathymosin, galectin-1, Factor XIIIa, ATL-derived factor, annexin-1, transglutaminase, mammary-derived growth inhibitor, macrophage migration inhibitory factor (MIF), HIV tat, ATP synthase, aminoacyl-tRNA synthetase, EMAP, rhodanase, and thioredoxin-like protein.

In another aspect, modulators that decrease export of a leaderless protein from a cell are provided. The modulator should decrease export of a leaderless protein; should not inhibit secretion of a leader sequence-containing protein; and should alter the stability of a complex, the complex comprising a leaderless protein and a transport molecule. In certain preferred embodiments, the transport molecule may include, for example, a gastrin binding protein/alpha subunit of mitochondrial fatty acid β-oxidation multienzyme complex (p70, GenBank Accession Nos. U04627/D16480), a phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components.

In yet another aspect, methods are provided for detecting one or more components of a cell transport pathway, by contacting cell extracts or cell membranes containing components of a cell transport pathway with a fusion protein of a transport molecule and a tag, to form a complex of the fusion protein with one or more components of the cell transport pathway; isolating the complex; and detecting one or more components of the cell transport pathway in the complex. In certain embodiments, one or more components of the cell transport pathway may include a leaderless protein and/or a transport molecule. In certain preferred embodiments, the transport molecule may include, for example, a gastrin binding protein/alpha subunit of mitochondrial fatty acid β-oxidation multienzyme complex (p70, GenBank Accession Nos. U04627/D16480), a phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components. In certain other embodiments, the tag may be glutathione-S-transferase or a fragment thereof that binds glutathione.

In addition, methods for decreasing export of a leaderless protein are provided, comprising contacting a cell with an effective amount of a modulator, the modulator comprising a nucleic acid molecule capable of binding and reducing translation of RNA encoding a transport molecule, wherein the transport molecule may be a gastrin binding protein/alpha subunit of mitochondrial fatty acid β-oxidation multienzyme complex (p70, GenBank Accession Nos. U040271D16480), a phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components. In one embodiment, the nucleic acid molecule may be DNA or RNA encoding at least 10 nucleotides (e.g., antisense molecules) of a transport molecule RNA.

Methods are also provided for identifying a compound that modulates leaderless protein export, which comprises contacting a cell with a candidate compound; and detecting a change in extracellular or intracellular levels of a leaderless protein. In one embodiment, the leaderless protein may be fused to a polypeptide tag or detection. In certain embodiments, the polypeptide tag may be green fluorescent protein. In one embodiment, the extracellular levels of the leaderless protein may be detected concomitantly with intracellular levels.

In another aspect, methods are provided for detecting a modulator that alters a leaderless protein/transport molecule complex, which includes contacting a protein complex comprising at least one leaderless protein and at least one transport molecule, with a candidate modulator for a time sufficient to alter the stability of the complex; and detecting a change in free transport molecule or free leaderless protein. In certain preferred embodiments, the transport molecule may include at least one of a gastrin binding protein/alpha subunit of mitochondrial fatty acid ,-oxidation multienzyme complex (p70, GenBank Accession Nos. U04627/D16480), a phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components.

In a related aspect, high throughput methods are provided for identifying a modulator that alters a leaderless protein/transport molecule complex stability, providing one or more transport molecules or leaderless proteins adsorbed to a solid support; contacting the adsorbed transport molecule or leaderless protein with a leaderless protein or transport molecule, respectively, wherein the leaderless protein or transport molecule is fused to a polypeptide tag for detection, and a candidate modulator under conditions suitable and for a time sufficient for the leaderless protein and transport molecule to form a complex; and detecting increased or decreased levels of tag at the solid surface as a measure of complex formation. In certain preferred embodiments, the transport molecule may be at least one of a gastrin binding protein/alpha subunit of mitochondrial fatty acid β-oxidation multienzyme complex (p70, GenBank Accession Nos. U04627/D16480), a phosphotyrosine-independent ligand of the SH2 domain of p56lck (p62, GenBank Accession No. U46751), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components.

Methods are provided for increasing export of a leaderless protein from a cell, by contacting a cell with an effective amount of a modulator, wherein the modulator alters the stability of a complex, where the complex comprises a leaderless protein and a transport molecule, thereby increasing export of the leaderless protein from the cell. In certain preferred embodiments, the transport molecule may include, for example, a gastrin binding protein/alpha subunit of mitochondrial fatty acid β-oxidation multienzyme complex (p70, GenBank Accession Nos. U04627/D16480), a phosphotyrosine-independent ligand of the SH2 domain of p56lck (p62. GenBank Accession No. U46751), mitochondrial fatty acid β-oxidation trifunctional protein β subunit (TP-β) (p48, GenBankl Accession No. D16481). actin related protein 3 (Arp3) (p48, GenBank Accession No. U29610), K-glypican (GenBank Accession No. X83577), tubulin (p50, GenBank Accession No. AF081484) and related polypeptides that are functionally equivalent in their role as leaderless protein trafficking components.

These and other aspects of the present invention will become evident upon reference to the following detailed description and attached drawings. Various references are set forth below which describe in more detail certain procedures or compositions (e.g., plasmids). All of these references are incorporated by reference in their entirety.

BRIEF DESCRIPTION OF THE DRAWINGS AND SEQUENCE LISTING

FIG. 1 is a drawing indicating four models for inhibition of FGF-2 export by cardioglycosides. A, $Na^+/K^+$ ATPase is a component of a plasma membrane translocation apparatus (PMTA/exporter) for FGF-2; B, the transmembrane electrochemical gradient established by $Na^+/K^+$ ATPase is functionally necessary for some other protein required for FGF-2 export; C, cardioglycosides interact with an unidentified protein required for FGF-2 export; D, cardioglycosides interact with $Na^+/K^+$ ATPase which interacts with another component of plasma membrane translocation apparatus.

FIG. 2 is an autoradiogram of an immunoprecipitation electrophoresed on an SDS-polyacrylamide gel. Panel A, immunoprecipitation of cell (C) and media (M) fractions with anti-FGF-2 antibodies at various times following co-transfection of plasmids expressing FGF-2 and $Na^+/K^+$ ATPase. (S) contains molecular weight standards. The double arrow points to a 110 kDa protein, which is the size of rat $Na^+/K^+$ ATPase α1 subunit. Panel B, immunoprecipitation following transfection of FGF-2 plasmid alone.

FIG. 3 is an autoradiogram of an immunoprecipitation electrophoresed on an SDS-PAGE. Panel A, immunoprecipitation of cell (C) and media (M) fractions with anti-FGF-2 antibodies at various times following co-transfection of plasmids expressing FGF-2 and $Na^+/K^+$ ATPase; 1 mM ouabaini was included during cell culture. The arrow points to a 110 kDa protein, which is the size of rat $Na^+/K^+$ ATPase α1 subunit. Panel B, immunoprecipitation following co-transfection and culture with or without ouabain.

Figure 7:
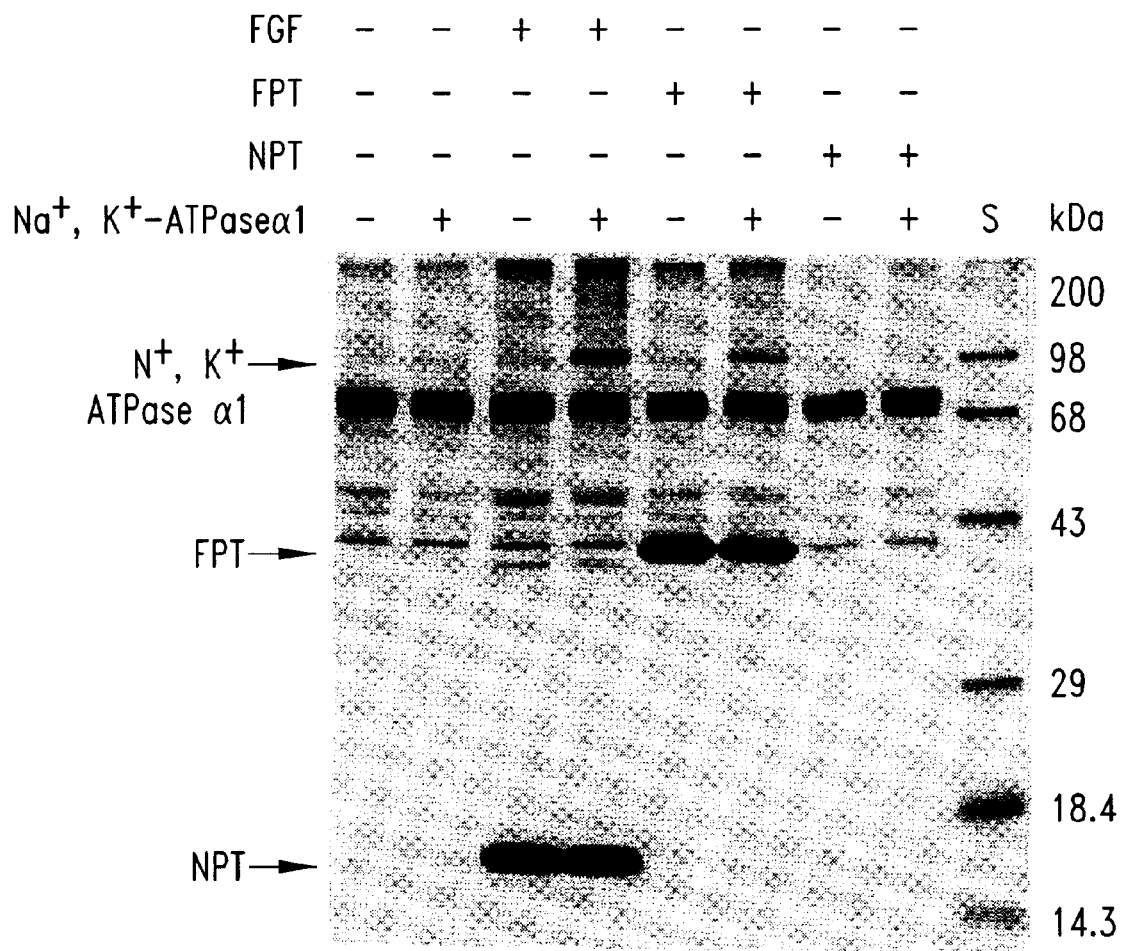

FIG. 7 is an autoradiogram of an immunoprecipitation with anti-FGF-2 immune serum following transfection of COS cells. The table at the top indicates the transfected genes. The lane marked "S" contains molecular weight standards. FPT is a chimera between FGF-2 and neomycin phosphotransferase.

Figure 8:
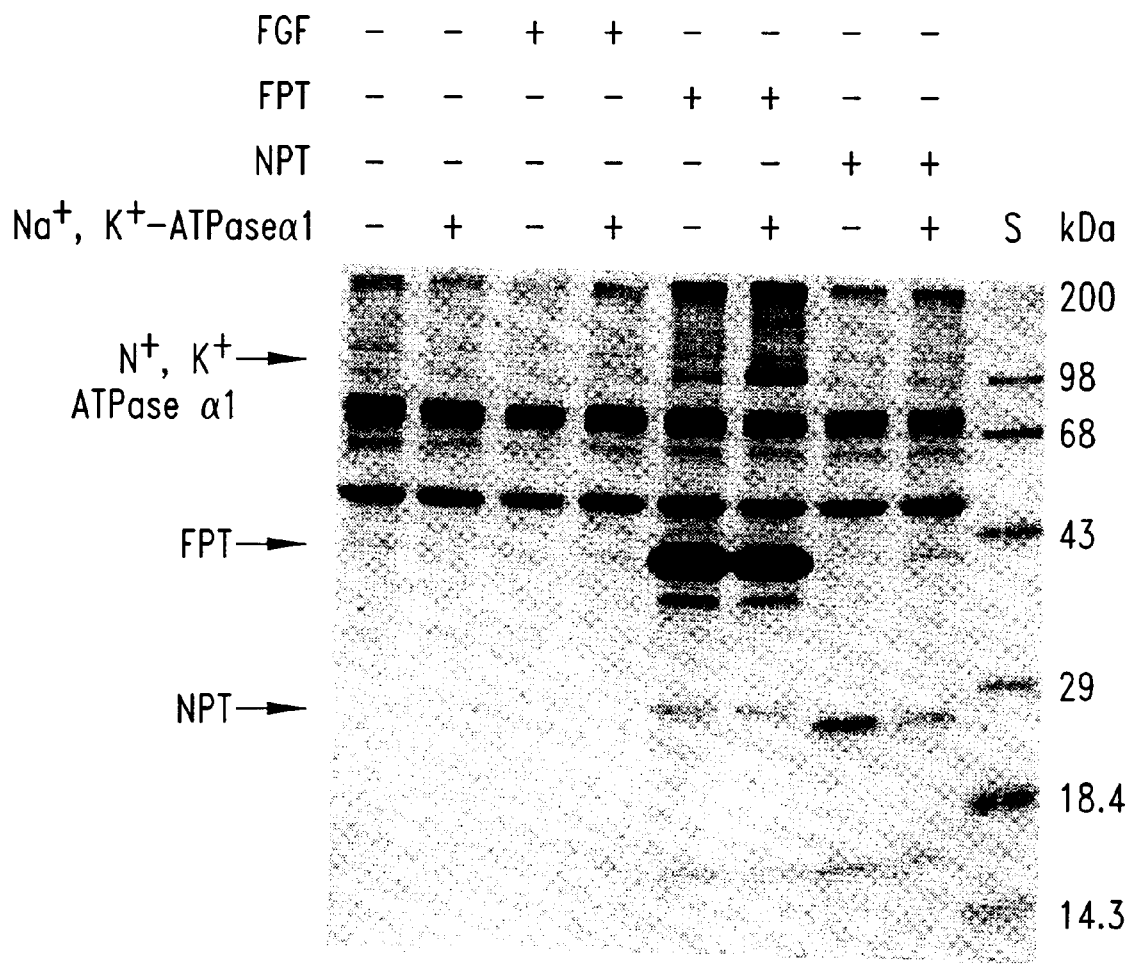

FIG. 8 is an autoradiogram of an immunoprecipitation with anti-neomycin phosphotransferase antibody following transfection of COS cells. The table at the top indicates the transfected genes. The lane marked "S" contains molecular weight standards. FPT is a chimera between FGF-2 and neomycin phosphotransferase.

Figure 9:
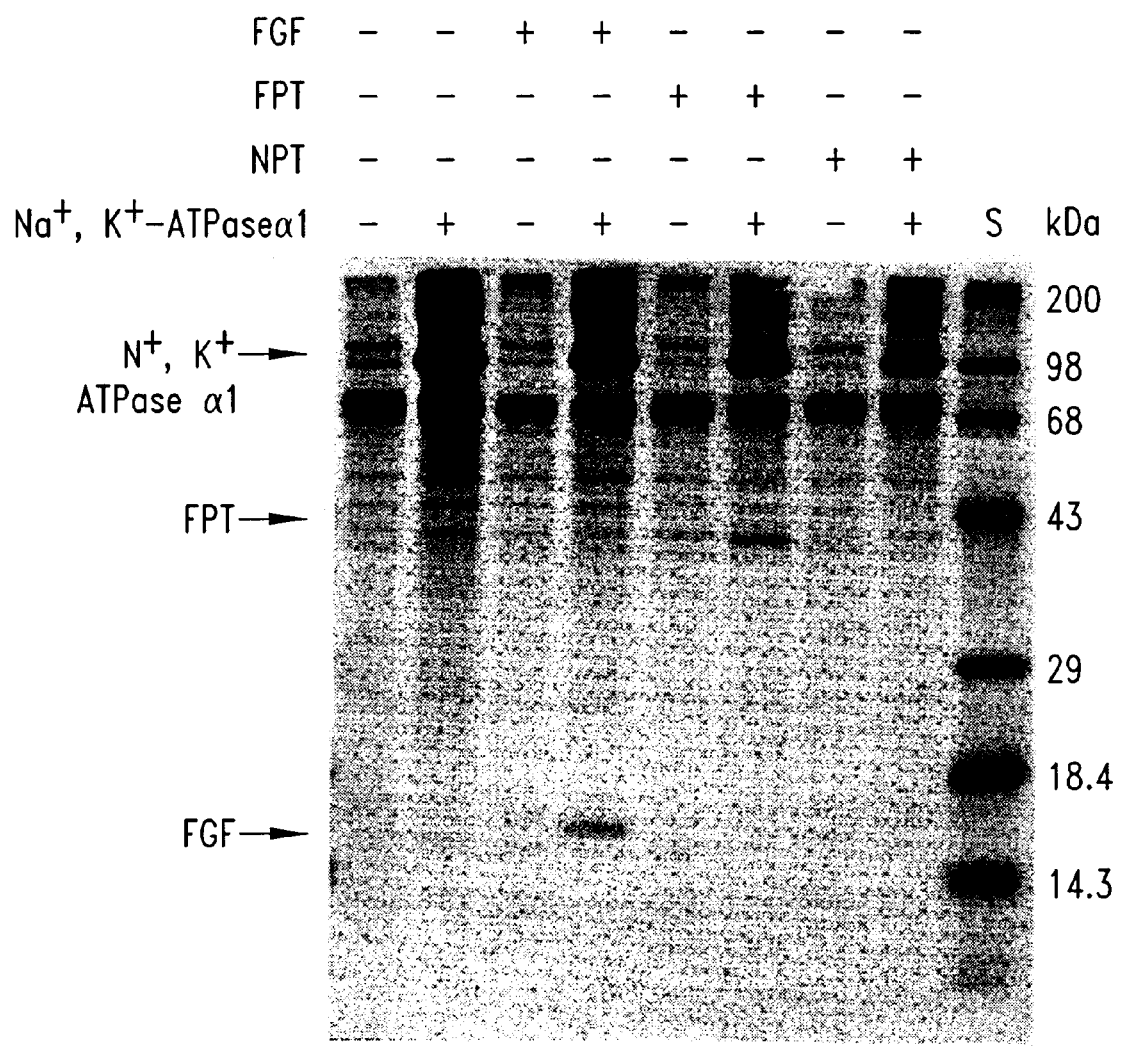

FIG. 9 is an autoradiogram of an immunoprecipitation with anti-Na$^+$/K$^+$ ATPase antibody following transfection of COS cells. The table at the top indicates the transfected genes. The lane marked "S" contains molecular weight standards. FPT is a chimera between FGF-2 and neomycin phosphotransferase.

Figure 10:
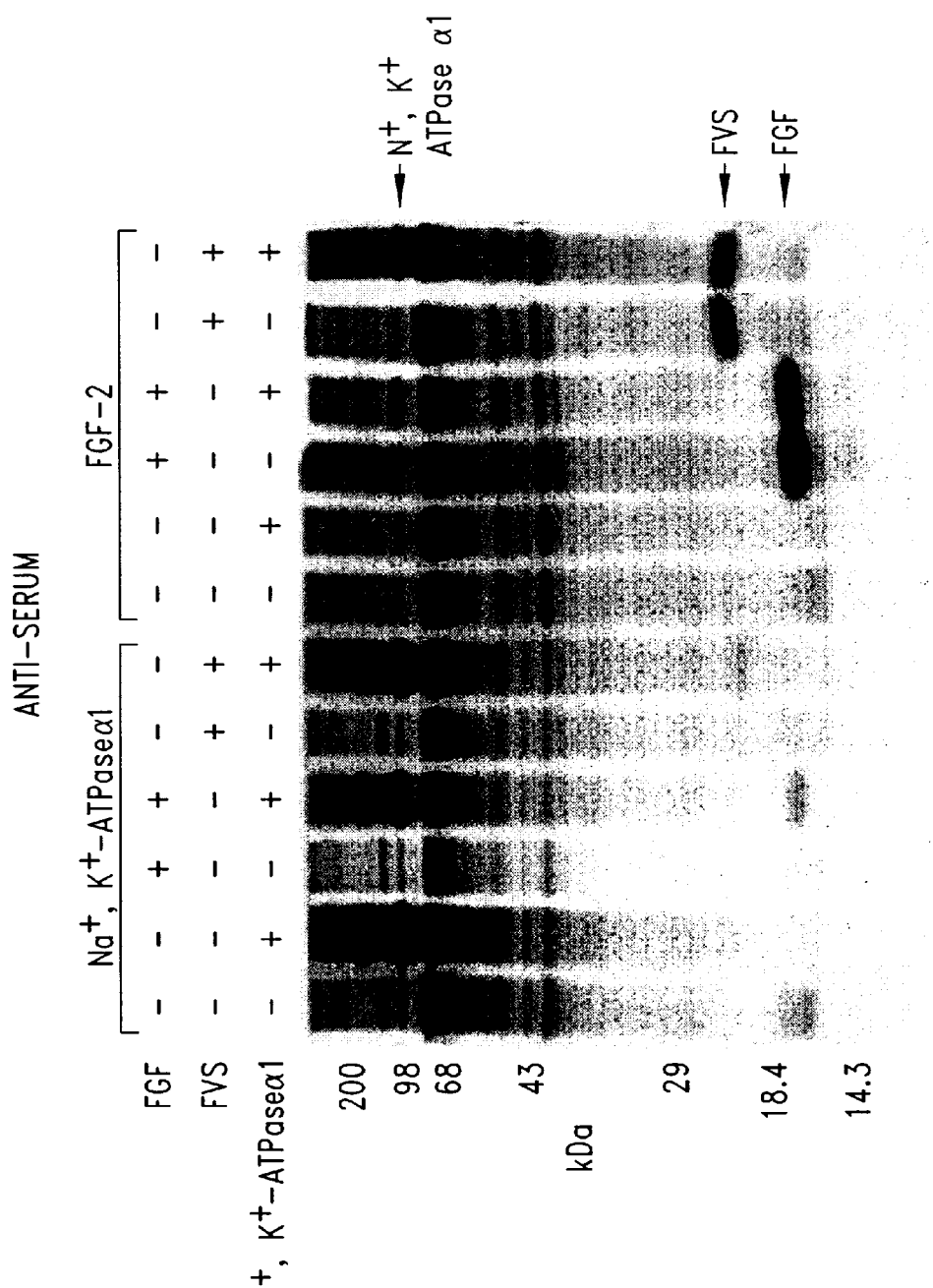

FIG. 10 is an autoradiogram of an immunoprecipitation with either anti-Na$^+$/K$^+$ ATPase antibody or anti-FGF-2 antibody following transfection of COS cells. The table at the top indicates the transfected genes. FVS is a chimeria between vesicular stomatitis virus transmembrane domain and FGF-2.

Figure 11:
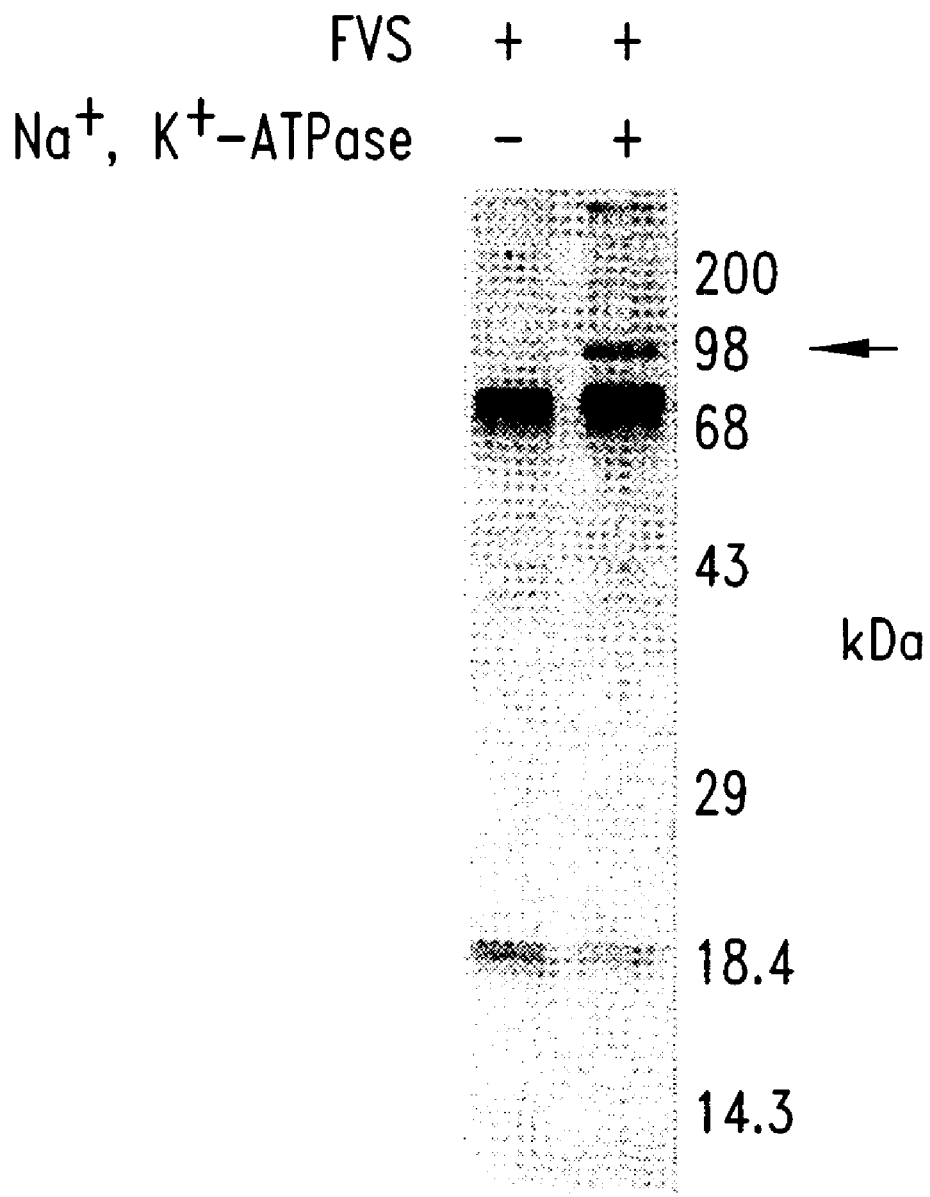

FIG. 11 is an autoradiogram of an immunoprecipitation with anti-FGF-2 antibody following transfection of COS cells. The table at the top indicates the transfected genes. FVS is a chimera between vesicular stomatitis virus transmembrane domain and FGF-2.

Figure 12A:
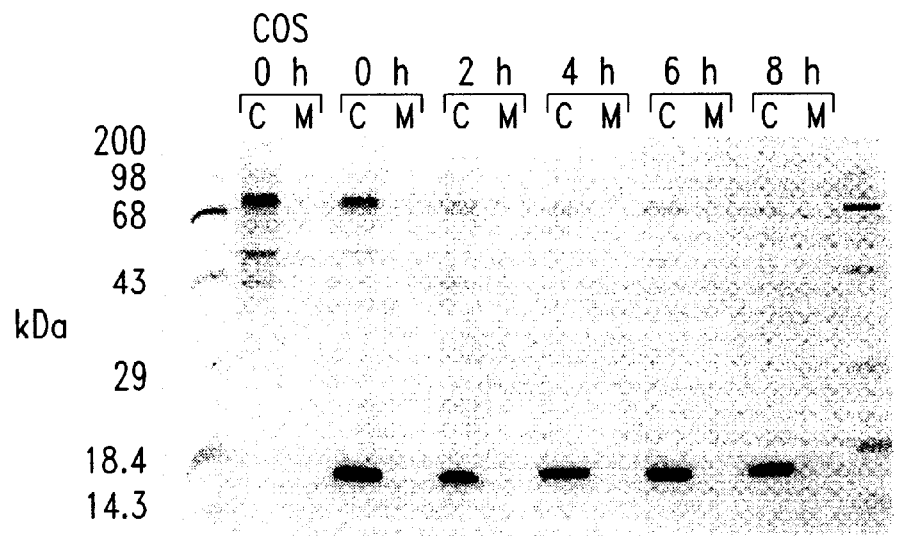
Figure 12B:
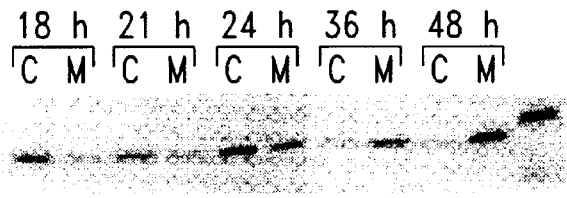

FIGS. 12A and 12B present an autoradiogram of an immunoprecipitation with anti-IL-1 antibody following transfection of COS cells with a plasmid encoding IL-1.

Figure 13:
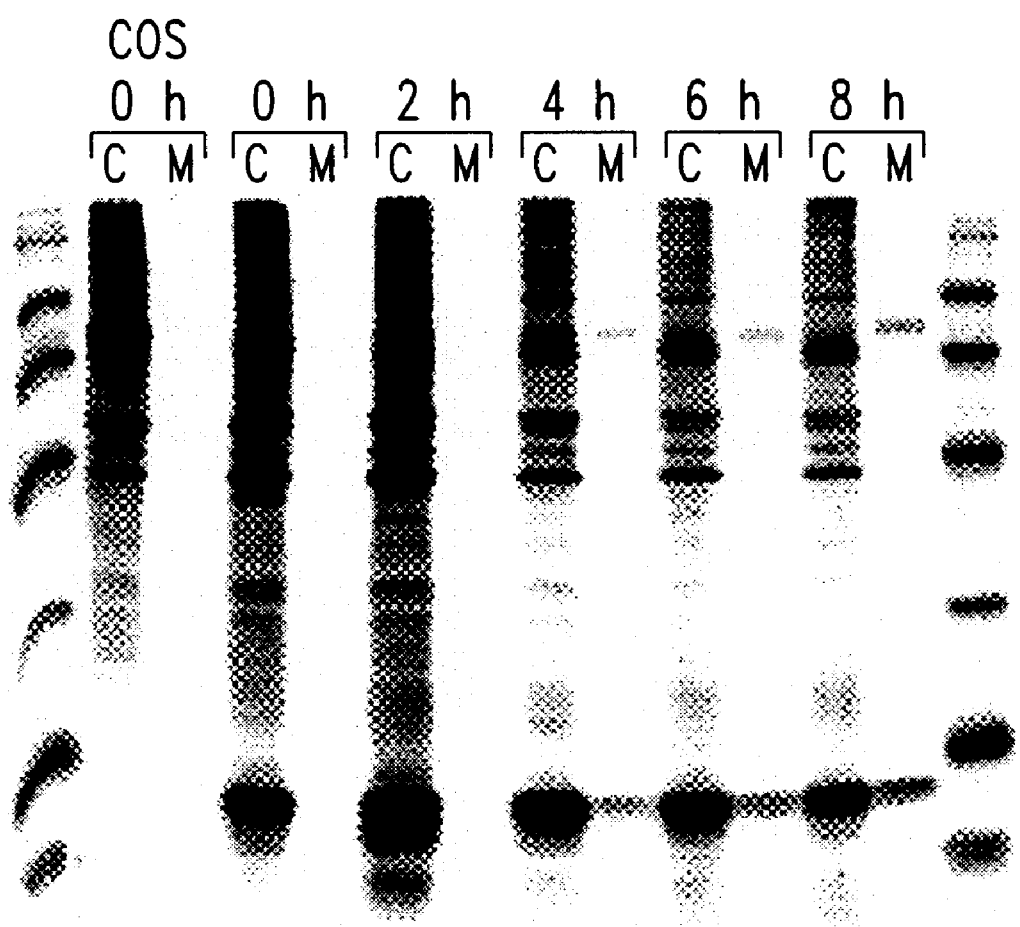

FIG. 13 is an autoradiogram of an immunoprecipitation with anti-FGF2 antibody following transfection of COS cells with plasmids expressing FGF2 and rat α2 subunit of Na$^+$/K$^+$ ATPase.

Figure 14:
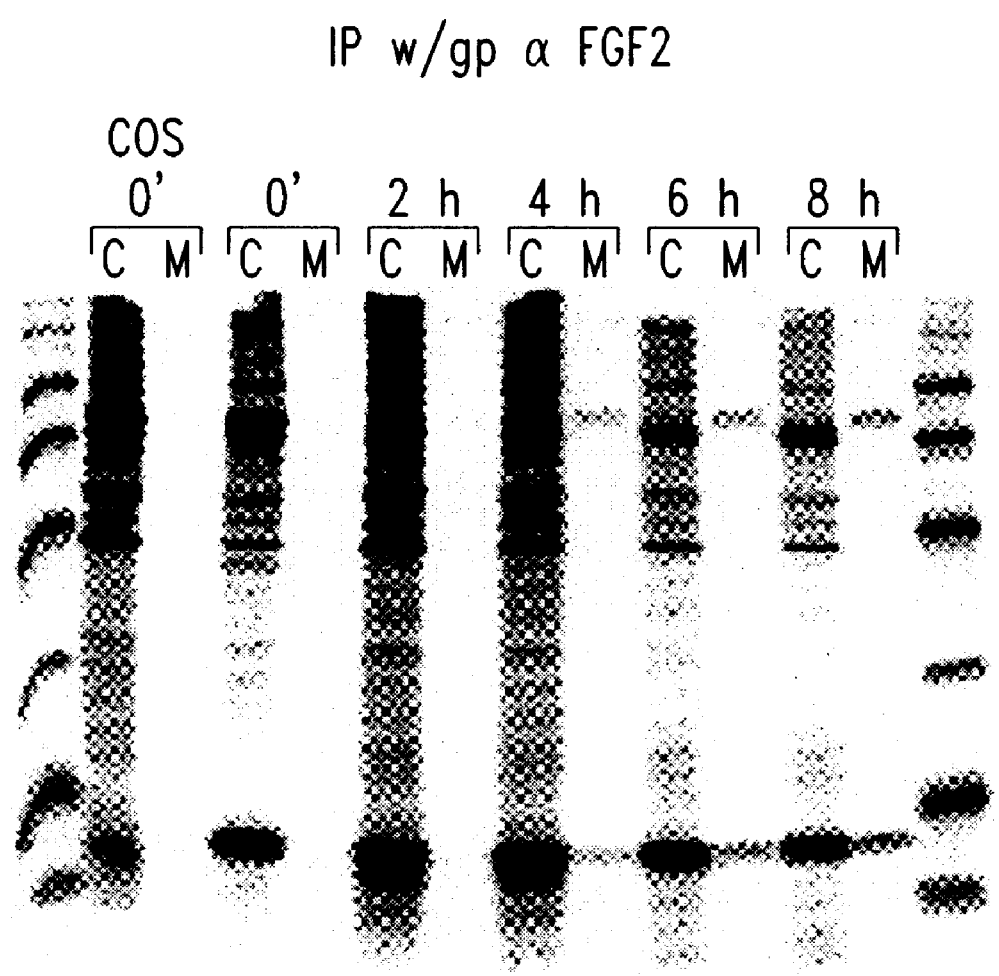

FIG. 14 is an autoradiogram of an immunoprecipitation with anti-FGF2 antibody following transfection of COS cells with plasmids expressing FGF2 and rat α3 subunit of Na$^+$/K$^+$ ATPase.

Figure 15:
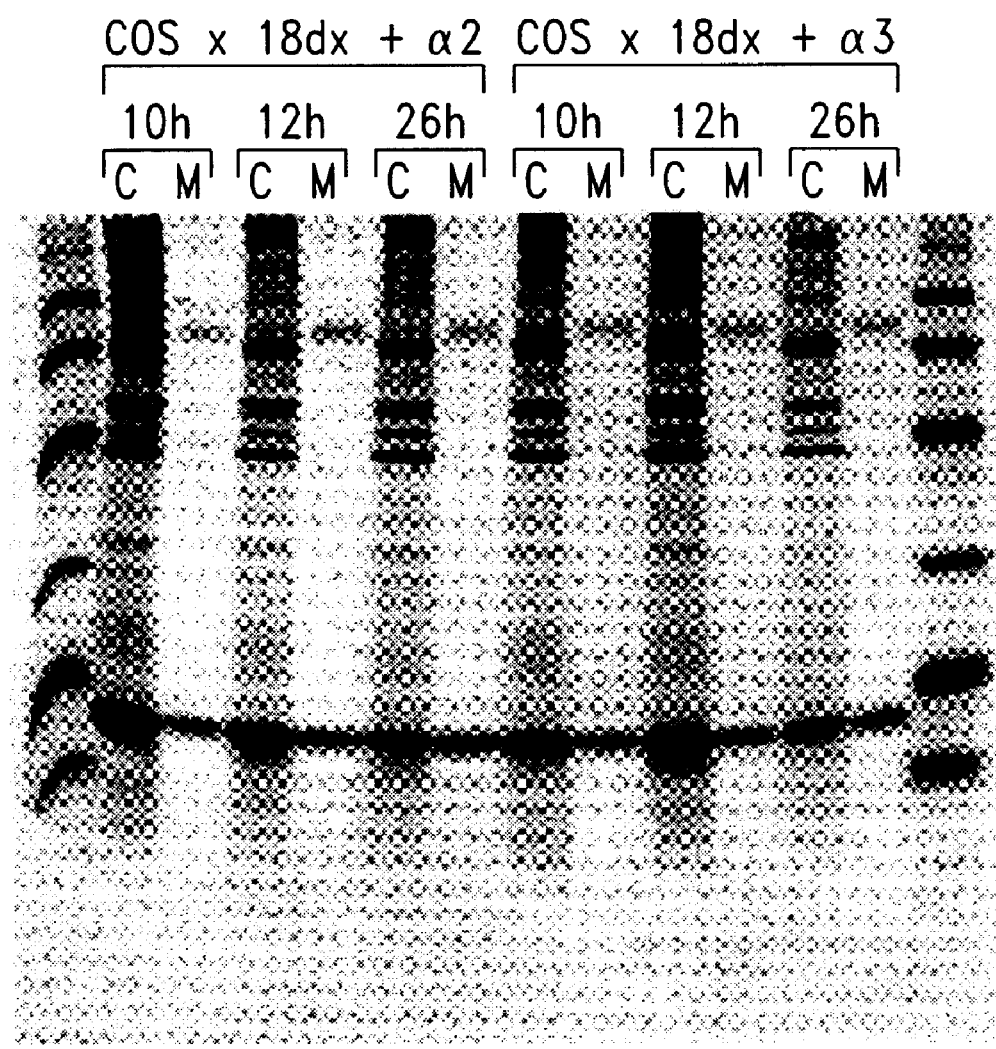

FIG. 15 is an autoradiogram of an immunoprecipitation with anti-FGF2 antibody following transfection of COS cells with plasmids expressing FGF2 and rat α2 subunit or FGF2 and rat α3 subunit.

Figure 16:
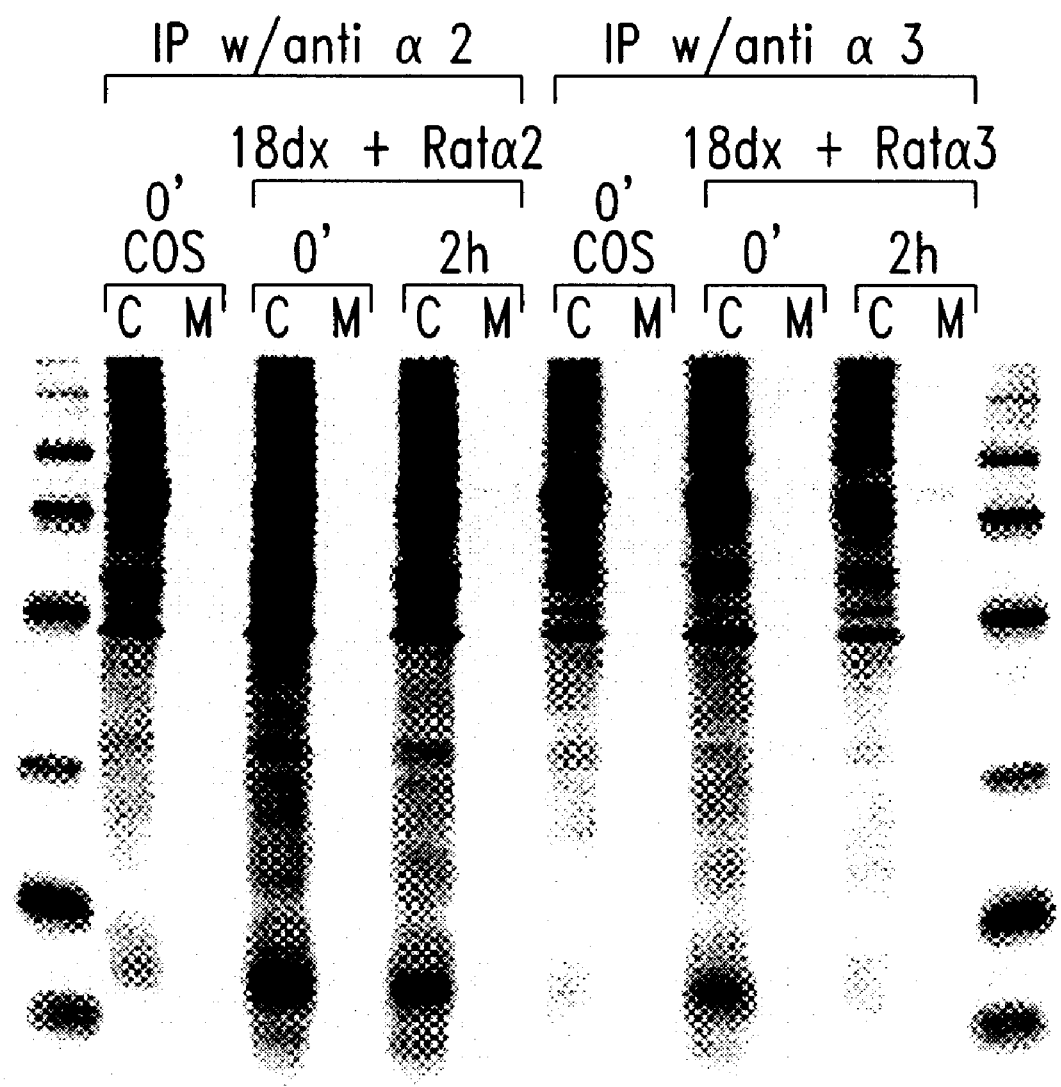

FIG. 16 is an autoradiogram of an immunoprecipitation with anti-α2 or anti-α3 subunit antibody following transfection of COS cells with plasmids expressing FGF2 and rat α2 subunit or FGF2 and rat α3 subunit.

Figure 17:
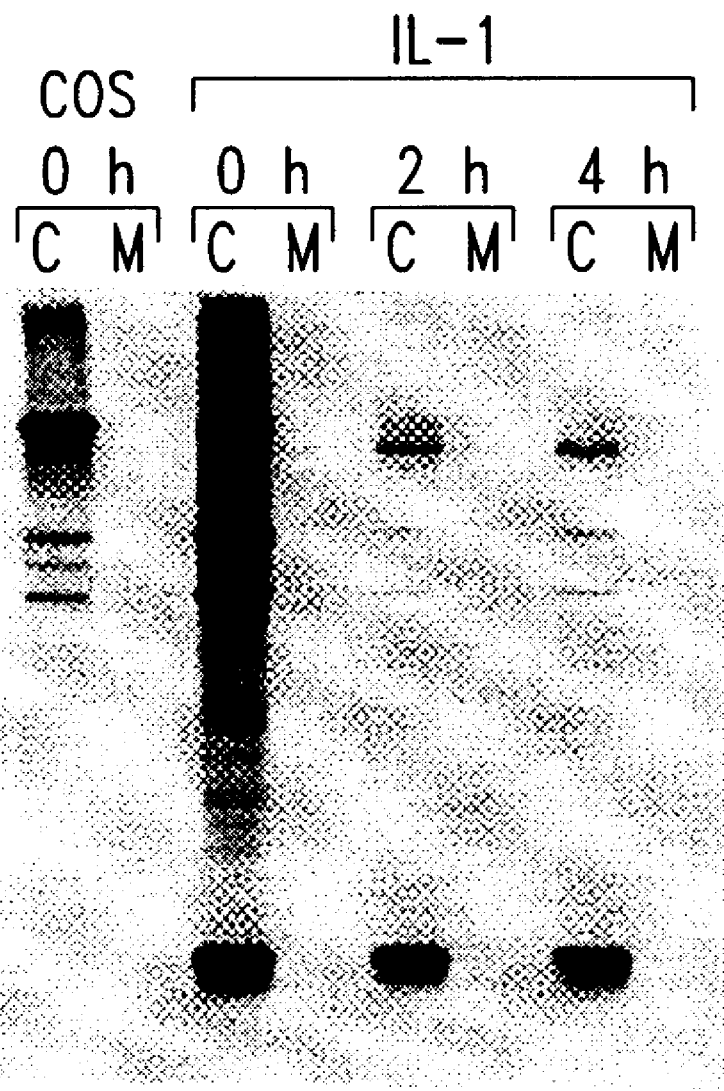

FIG. 17 is an autoradiogram of an immunoprecipitation with anti-IL-1 antibody following transfection of COS cells with a plasmid expressing IL-1.

Figure 18:
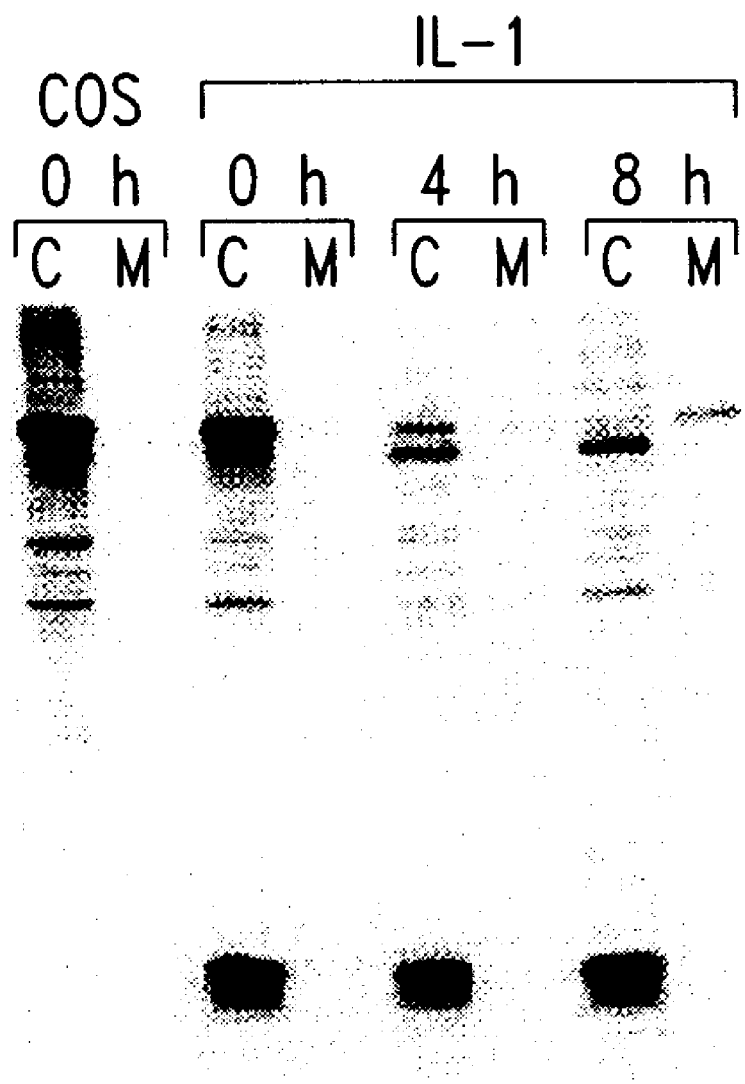

FIG. 18 is an autoradiogram of an immunoprecipitation with anti-IL-1 antibody following transfection of COS cells with a plasmid expressing IL-1 and treated with ouabain.

Figure 19:
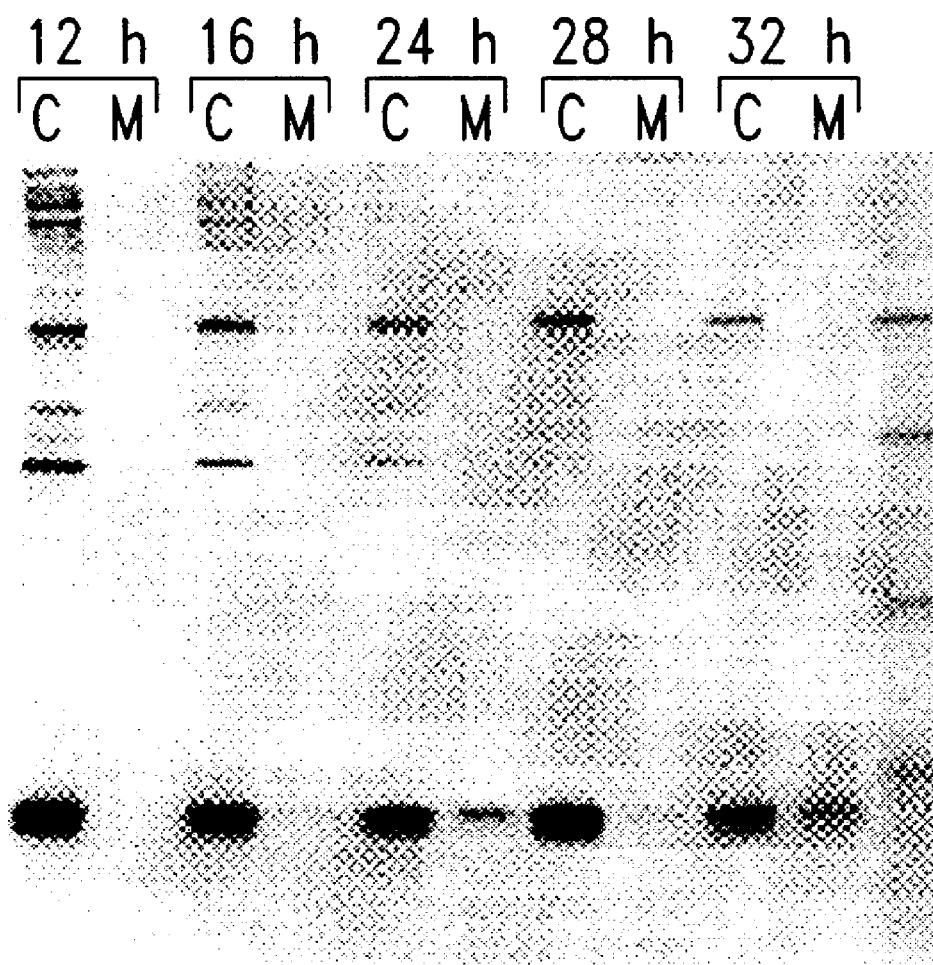

FIG. 19 is an autoradiogram of an immunoprecipitation with anti-IL-1 antibody following transfection of COS cells with a plasmid expressing IL-1.

Figure 20:
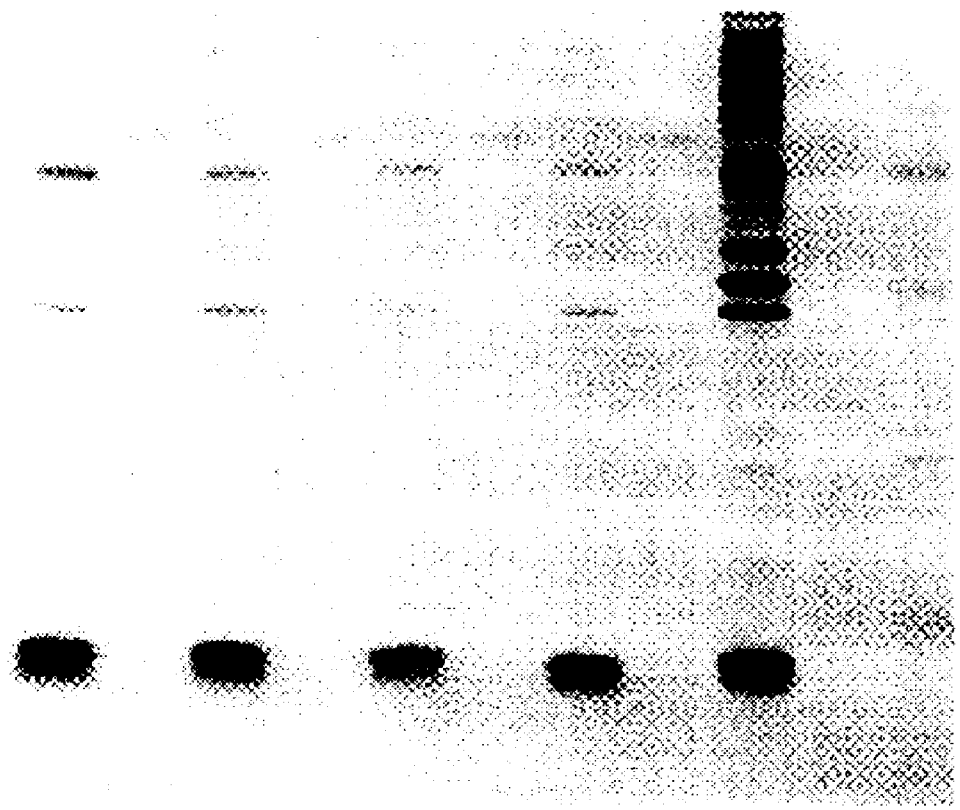

FIG. 20 is an autoradiogram of an immunoprecipitation with anti-IL-1 antibody following transfection of COS cells with a plasmid expressing IL-1 and treated with ouabain.

Figure 21:
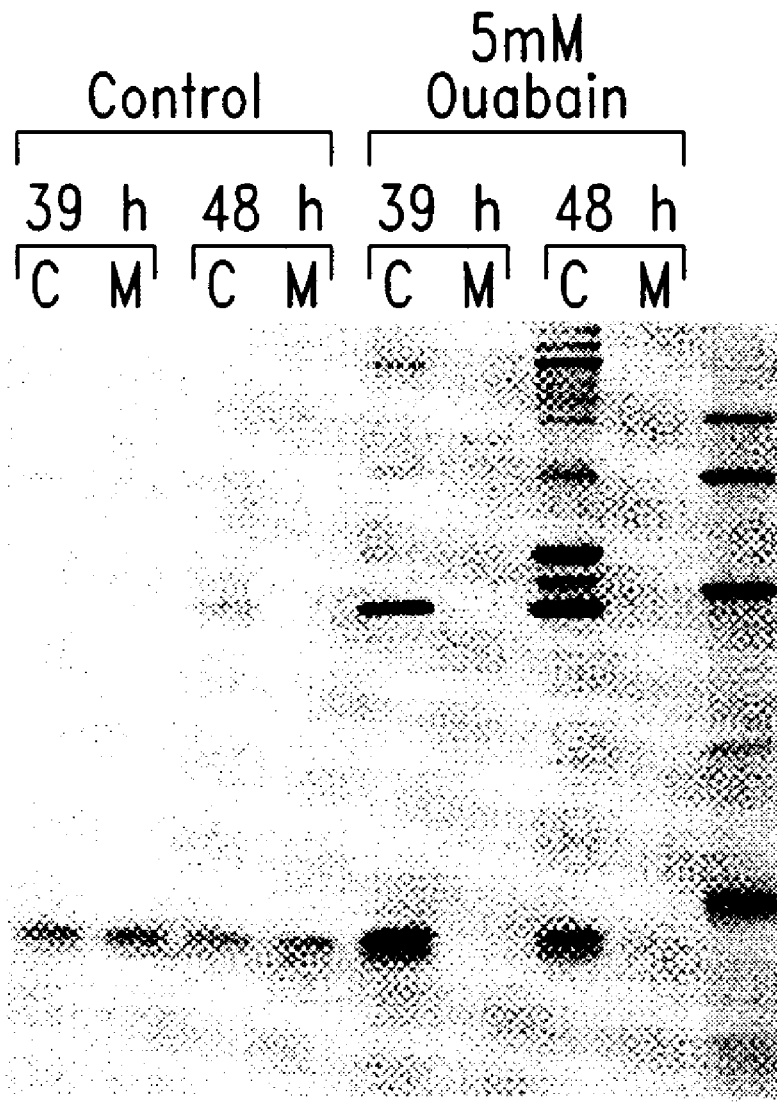

FIG. 21 is an autoradiogram of an immunoprecipitation with anti-IL-1 antibody following transfection of COS cells with a plasmid expressing IL-1 and either treated with ouabain or receiving no treatment.

Figure 22:
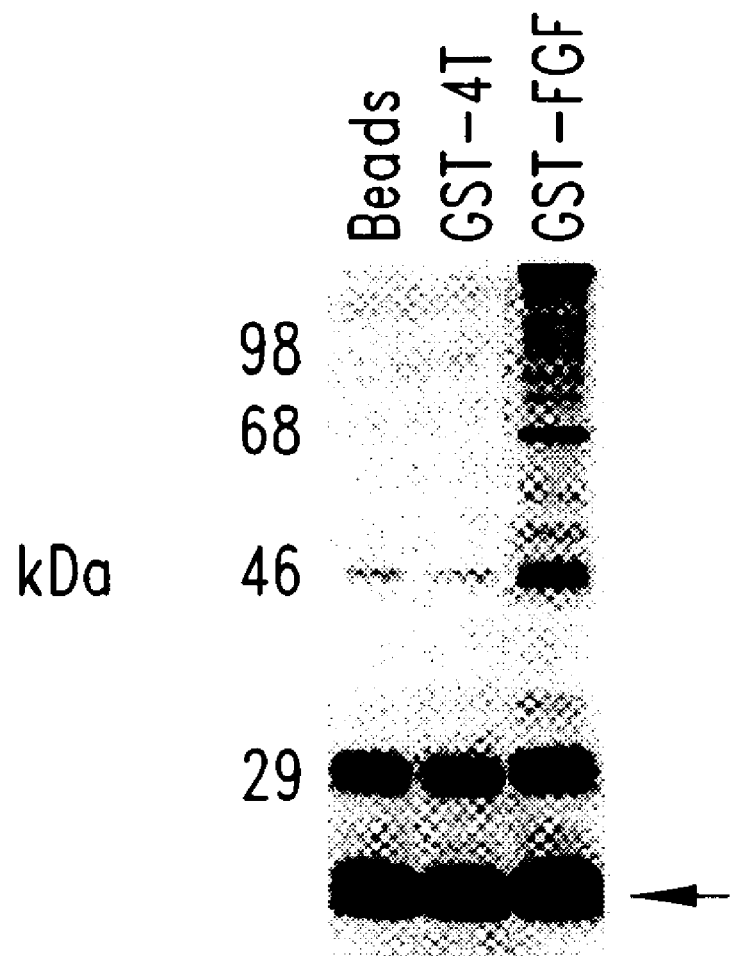

FIG. 22 is an autoradiogram of metabolically-labeled COS cell proteins that bind to an FGF-2/GST chimeric protein (GST-FGF). GST-4T is glutathione-s-transferase, beads are without any GST-based protein.

Figure 23:
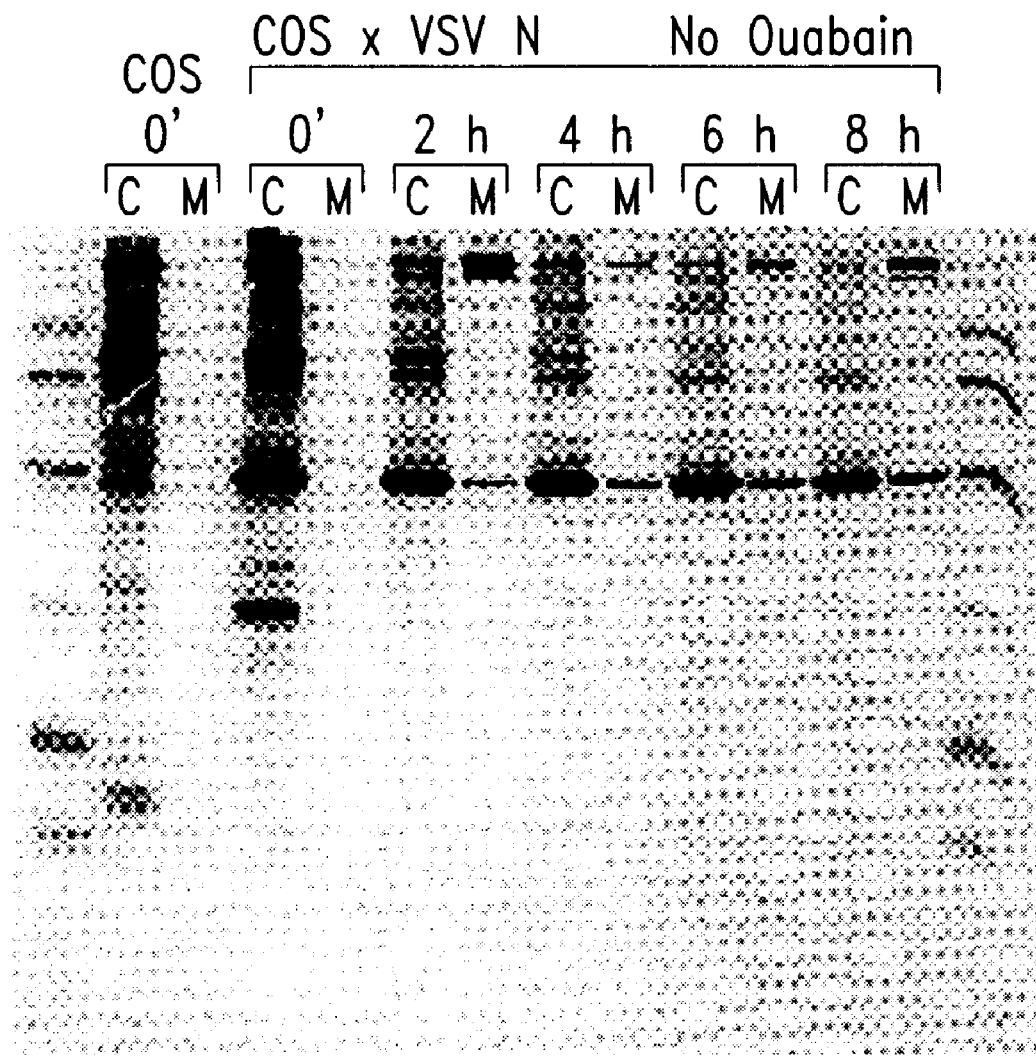

FIG. 23 is an autoradiogram of an immunoprecipitation with anti-VSV antibody following transfection of COS cells with a plasmid expressing VSV N protein.

Figure 24:

FIG. 24 is an autoradiogram of an immunoprecipitation with anti-VSV antibody following transfection of COS cells with a plasmid expressing VSV N protein and treated with ouabain.

Figure 25:
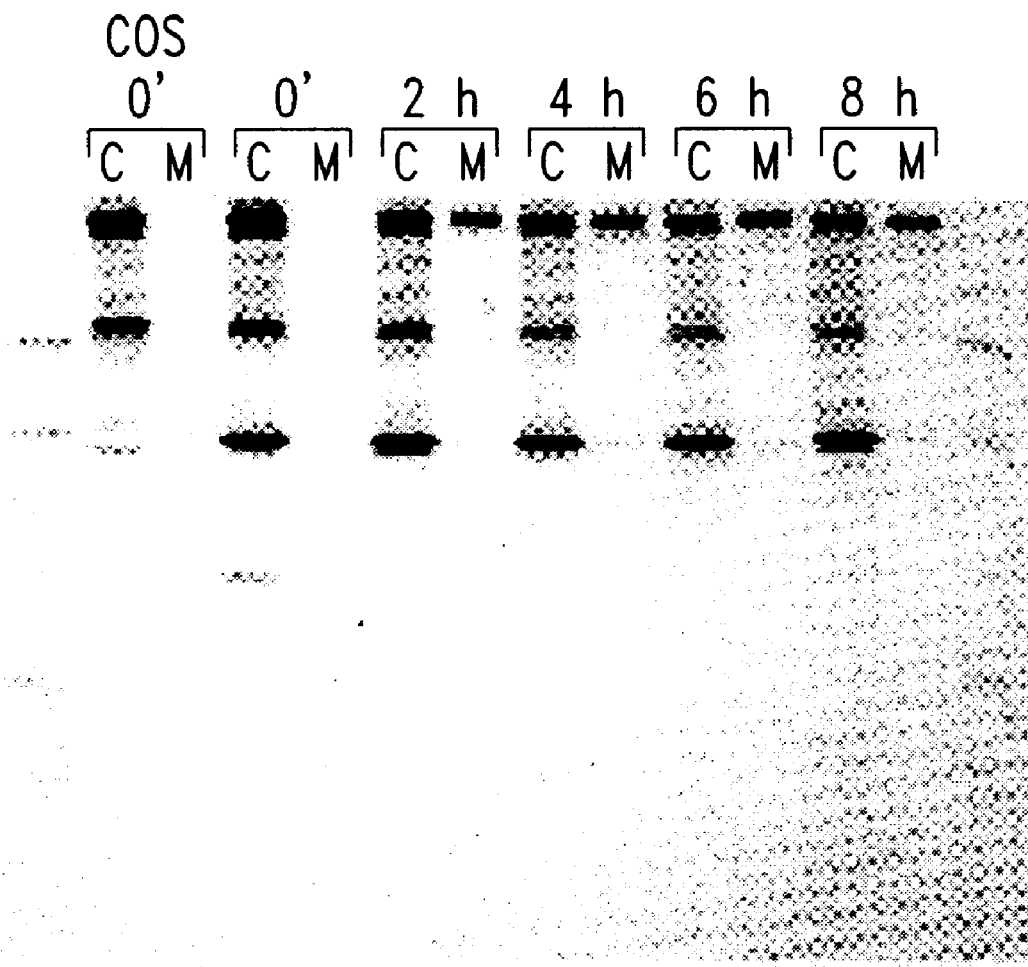

FIG. 25 is an autoradiogram of an immunoprecipitation with anti-VSV antibody following transfection of COS cells with a plasmid expressing VSV N protein and treated with 2-deoxyglucose and NaN$_3$.

Figure 26:
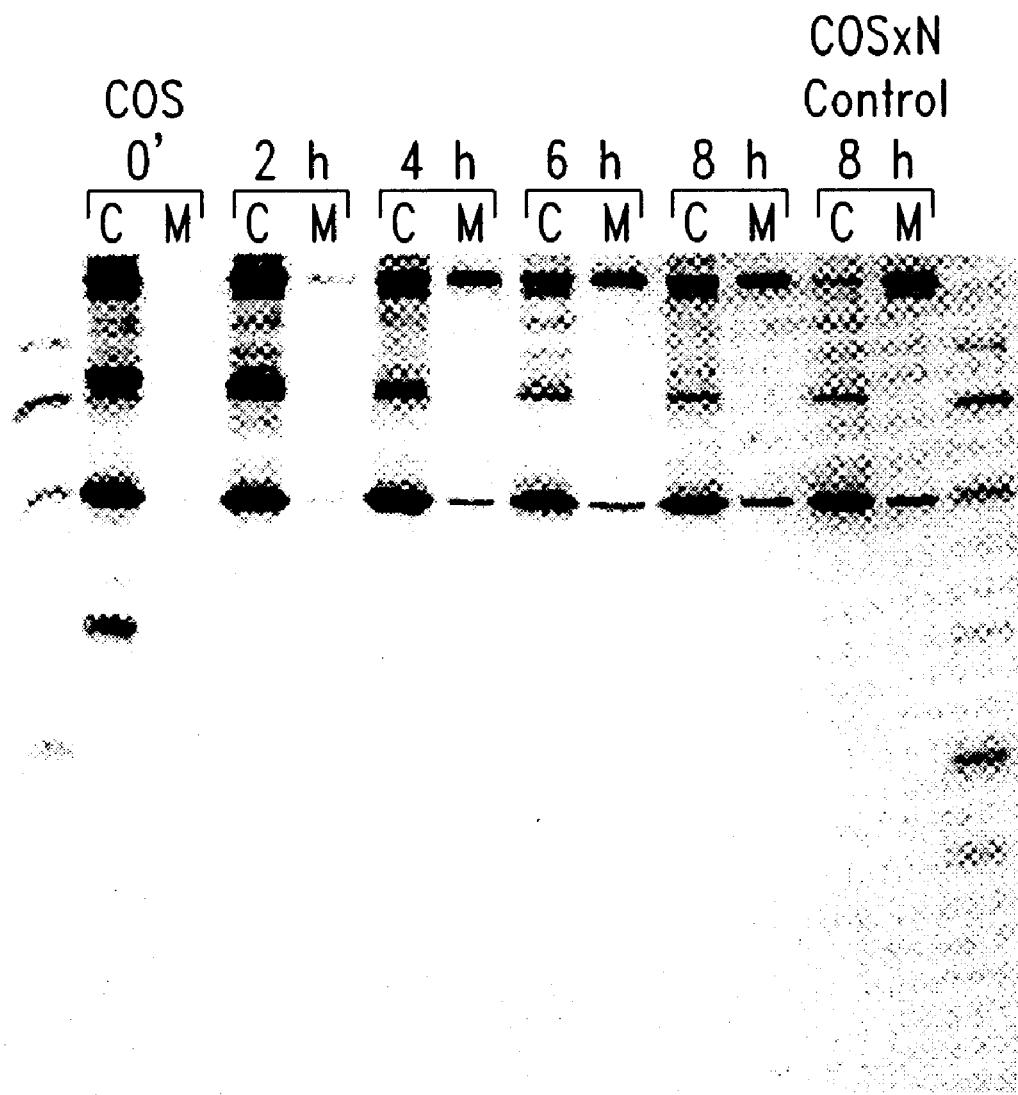

FIG. 26 is an autoradiogram of an immunoprecipitation with anti-VSV antibody following transfection of COS cells with a plasmid expressing VSV N protein and treated with brefeldin A.

Figure 27:
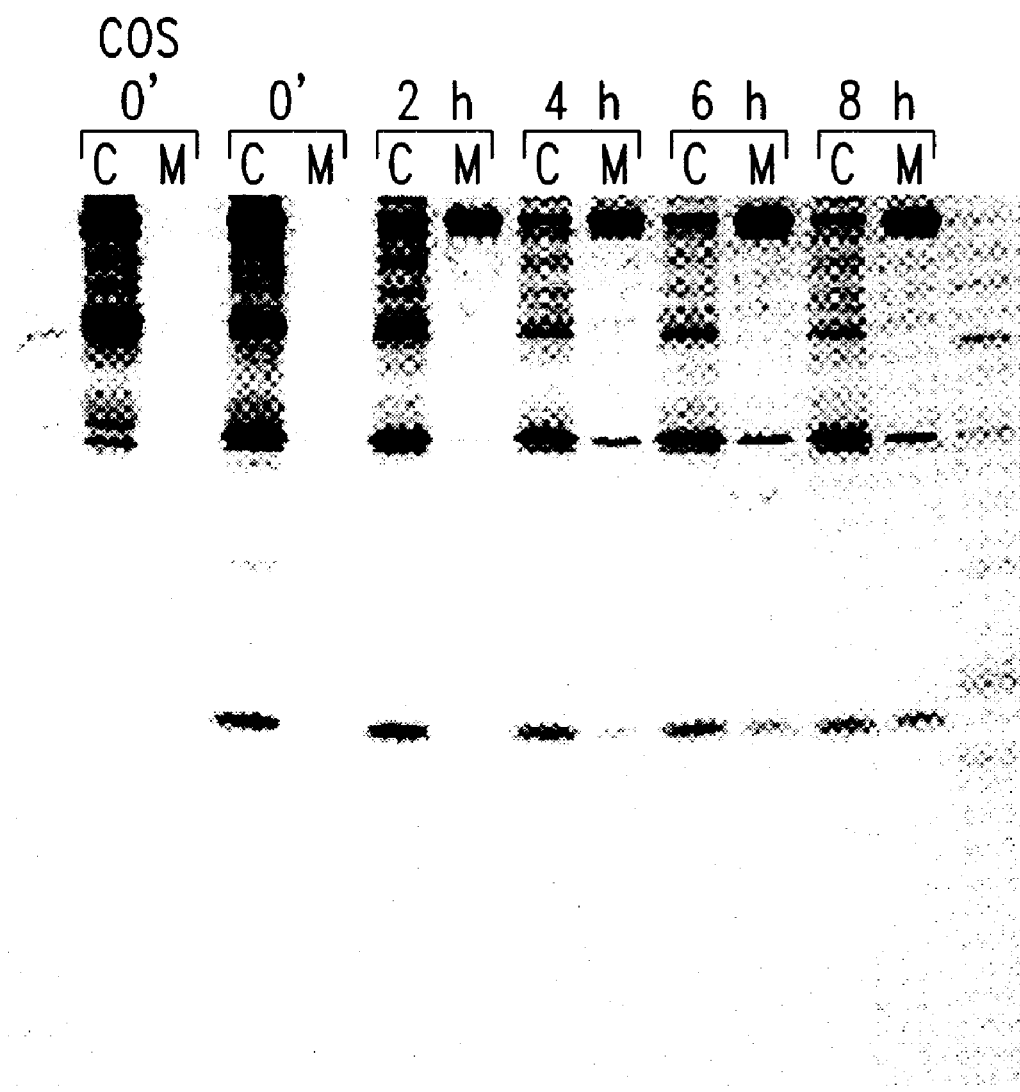

FIG. 27 is an autoradiogram of an immunoprecipitation with anti-FGF2 antibody following transfection of COS cells with plasmids expressing VSV N protein and FGF2.

Figure 28:
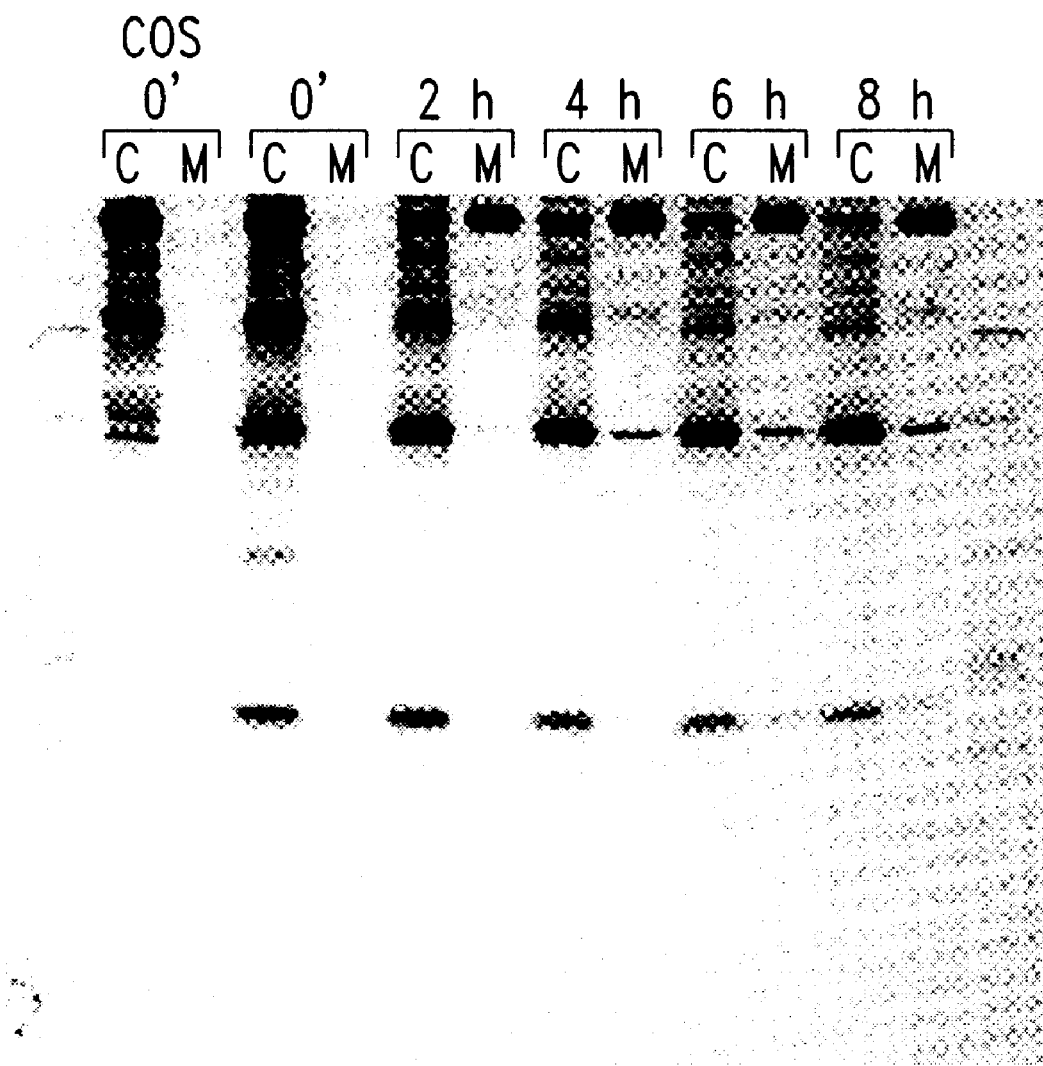

FIG. 28 is an autoradiogram of an immunoprecipitation with anti-FGF2 antibody following transfection of COS cells with plasmids expressing VSV N protein and FGF2 and treated with ouabain.

Figure 29C:
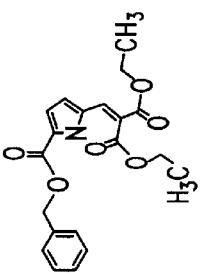

FIGS. 29A–29C present structures of small molecules that act as inhibitors of FGF-2 export.

Figure 30:
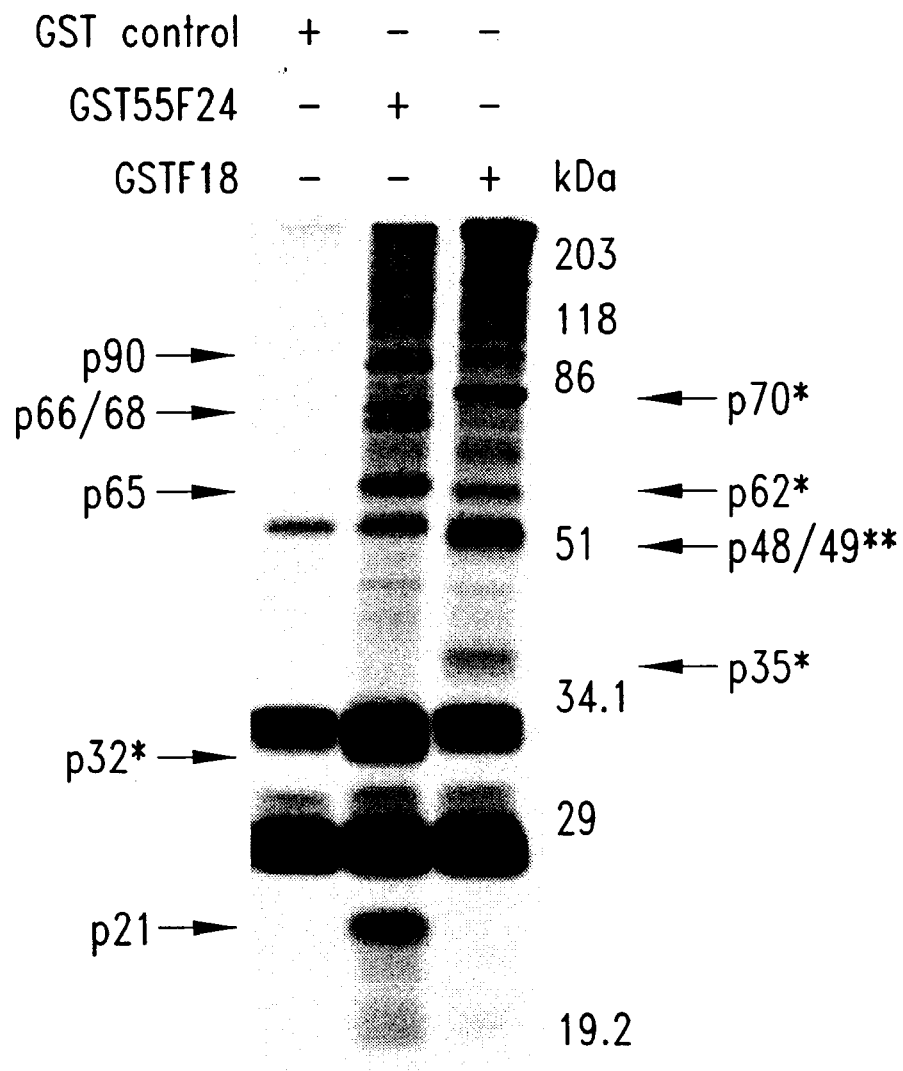

FIG. 30 is an autoradiogram of metabolically-labeled COS cell proteins that bind to an 18-kDa FGF-2/GST chimeric protein (GSTF18), a 55 amino acid NH$_2$-terminal domain specific to the 24-kDa isoform of FGF-2/GST (GST55F24). GST is glutathione-s-transferase without a fusion construct attached. Bands denoted by. asterisk have been identified by sequence analysis.

Figure 31:
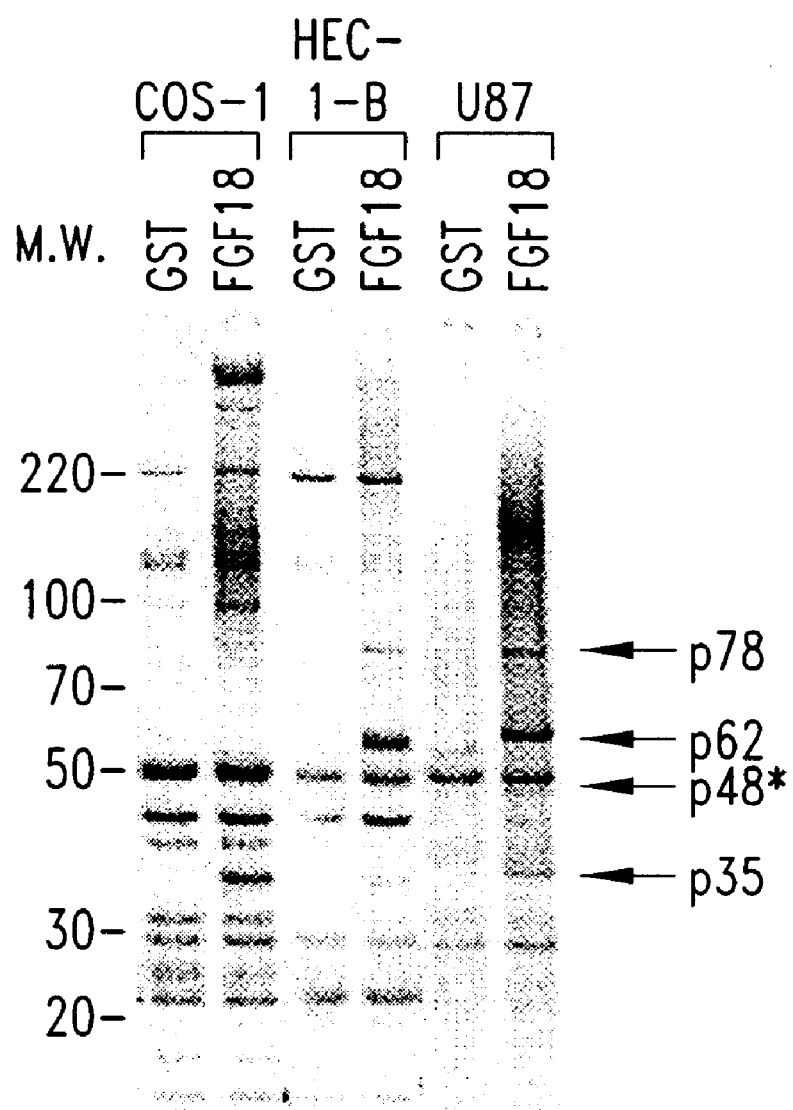

FIG. 31 is an autoradiogram of metabolically-labeled COS-1, HEC-1-B, and U87 cell proteins that bind to an 18-kDa FGF-2/GST chimeric protein (GSTF 18). GST is glutathione-s-transferase without a fusion construct attached.

Figure 32:
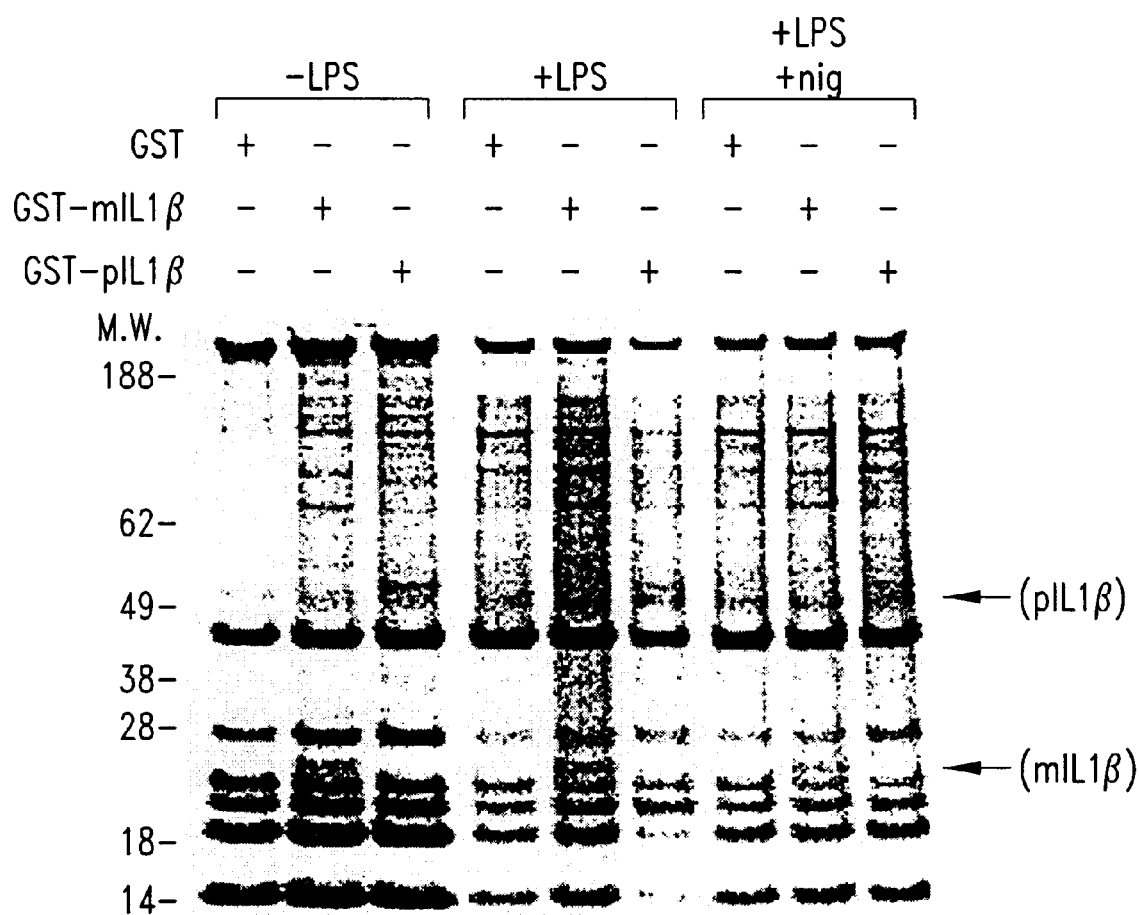

FIG. 32 is an autoradiogram of metabolically-THP-1 cell proteins that bind to a mature interleukin-1β/GST chimeric protein (GST-mIL 1β), a precursor interleukin-1β/GST chimeric protein (GST-pIL1β). GST is glutathione-s-transferase without a fusion construct attached. LPS represents lipopolysaccharide stimulation while nig represents nigericin stimulation.

Figure 33:
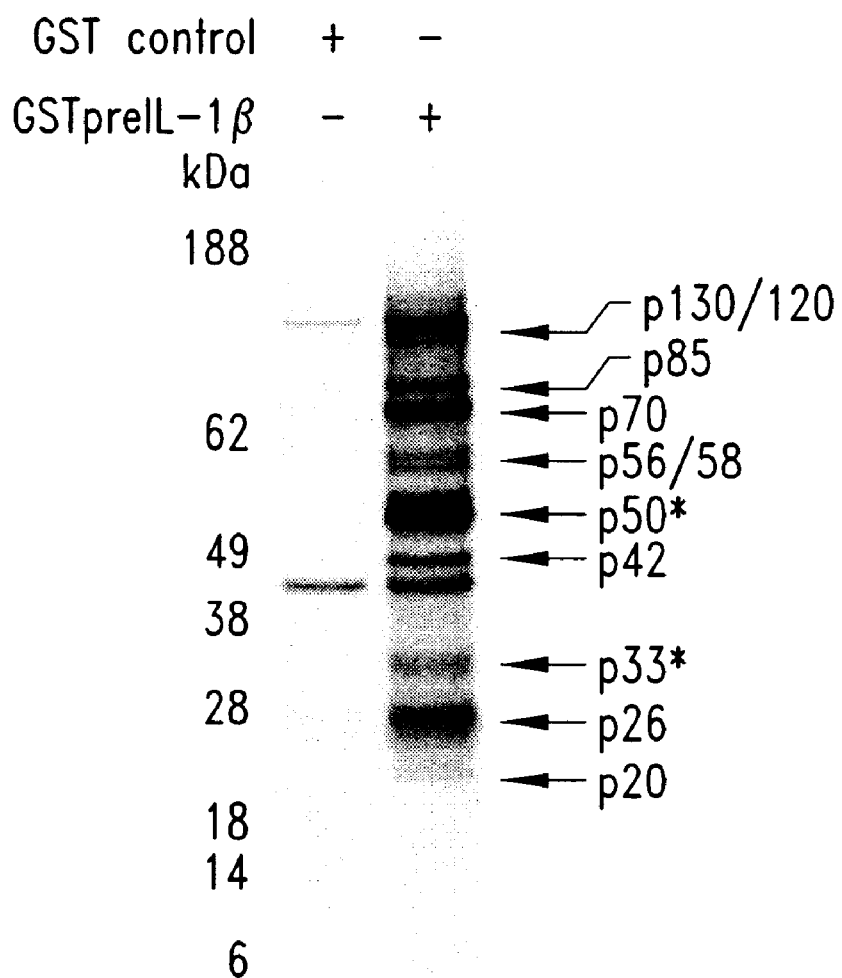

FIG. 33 is an autoradiogram of metabolically-THP-1 cell proteins that bind to a precursor interleukin-1β/GST chimeric protein (GST-pIL1β) in the absence of LPS. GST is glutathione-s-transferase without a fusion construct attached.

Figure 34:
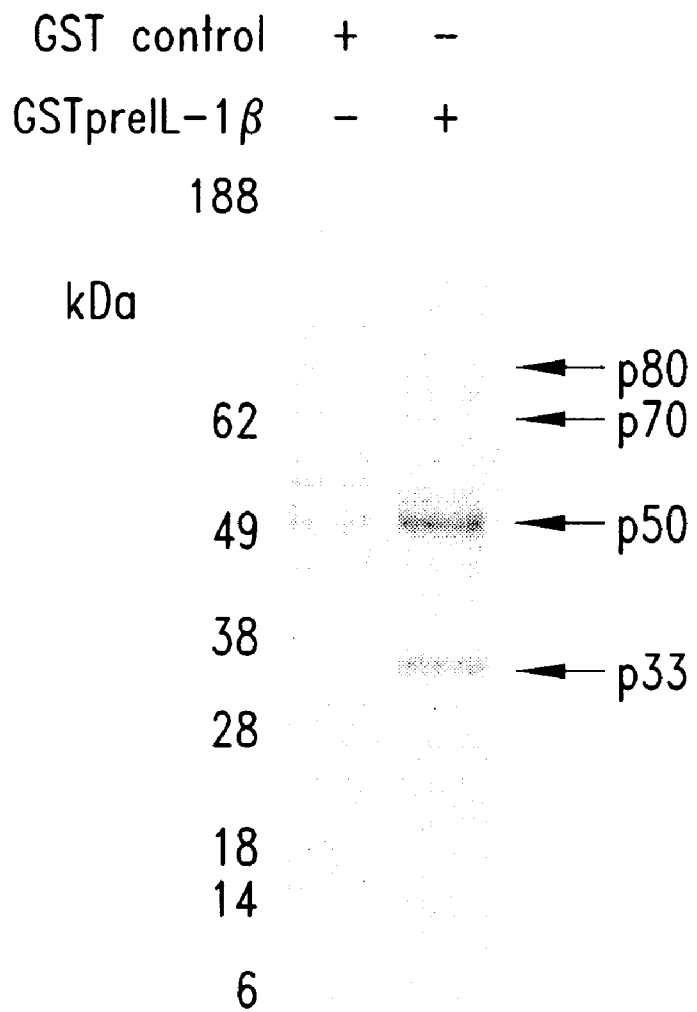

FIG. 34 is an autoradiogram of media derived metabolically-THP-1 cell proteins that bind to a precursor interleukin-1β/GST chimeric protein (GST-pIL1β) in the absence of LPS. GST is glutathione-s-transferase without a fusion construct attached.

Figure 35:
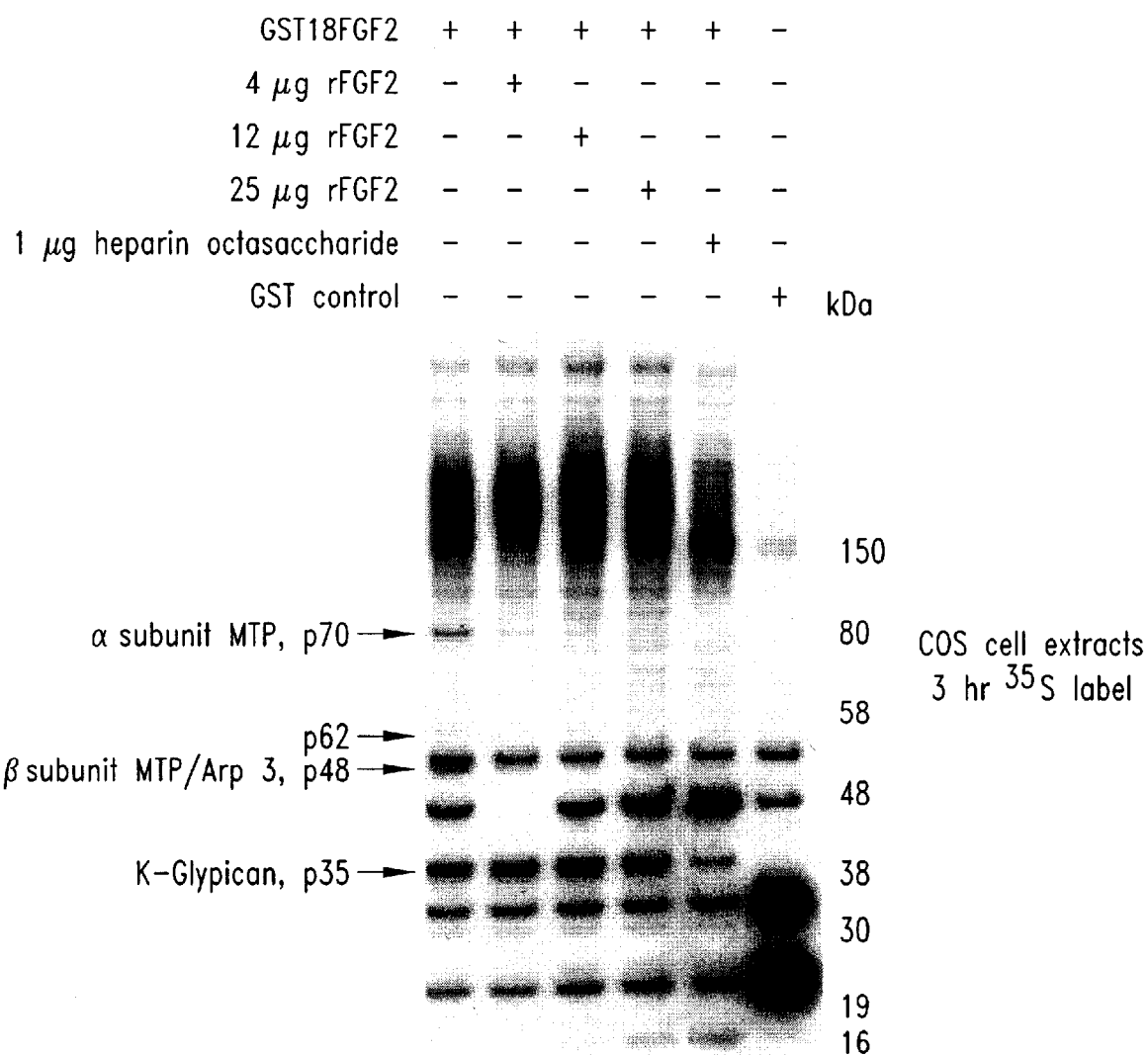

FIG. 35 is an autoradiogram representing the ability of varying levels of 18-kDa FGF2 to compete with GST18FGF2 interacting proteins.

Figure 36:
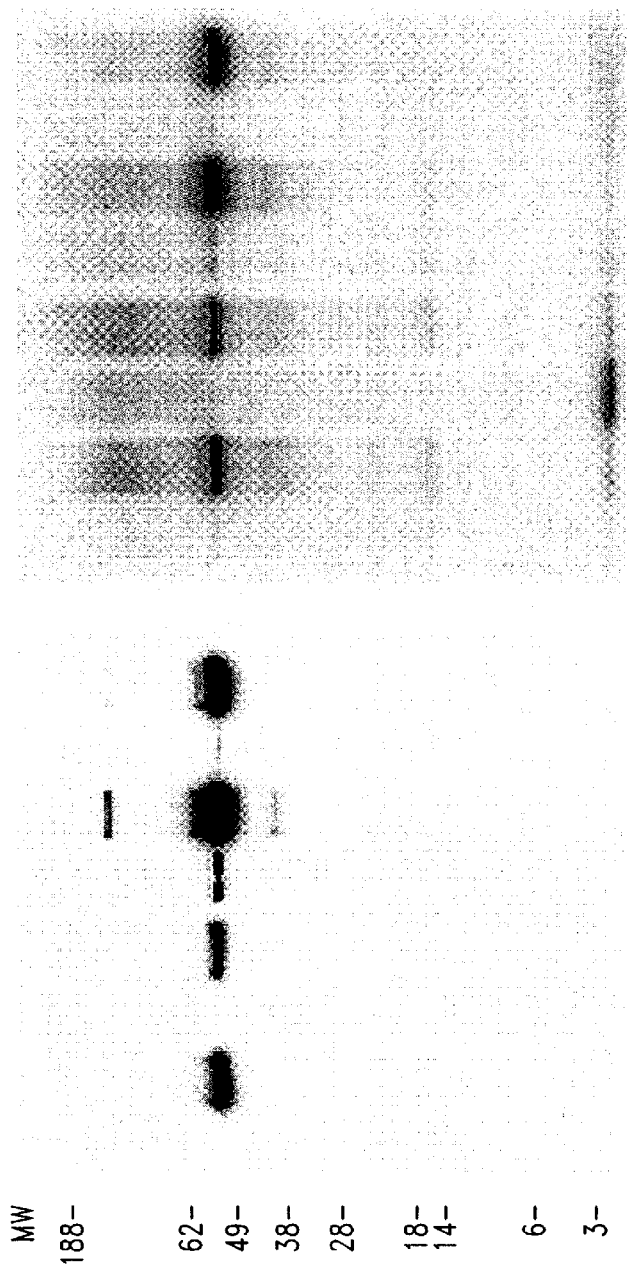

FIG. 36 is a western blot and an autoradiogram representing isolation of p62 from COS and HEC cels using HA tagged and untagged p62.

Figure 37:
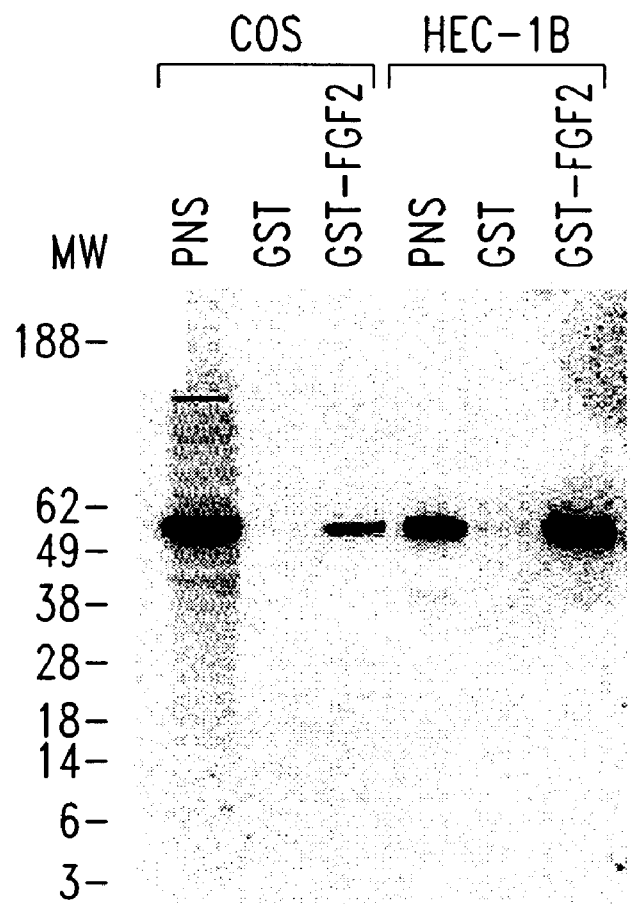

FIG. 37 represents western blot analysis using anti-HA antibodies to probe for the presence of p62HA in various fractions from using various fractions from COS and HEC-1B cells.

Figure 38:
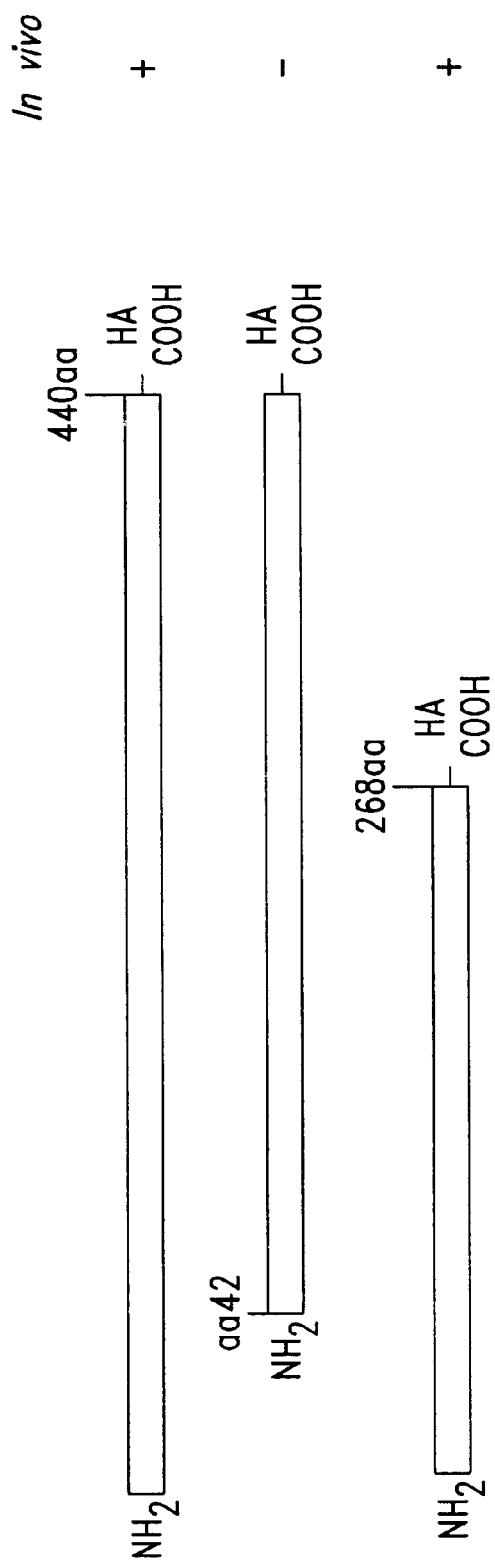

FIG. 38 represents a diagram of full-length p62 and two truncated forms along with an indication of binding to GST18FGF2.

Figure 39:
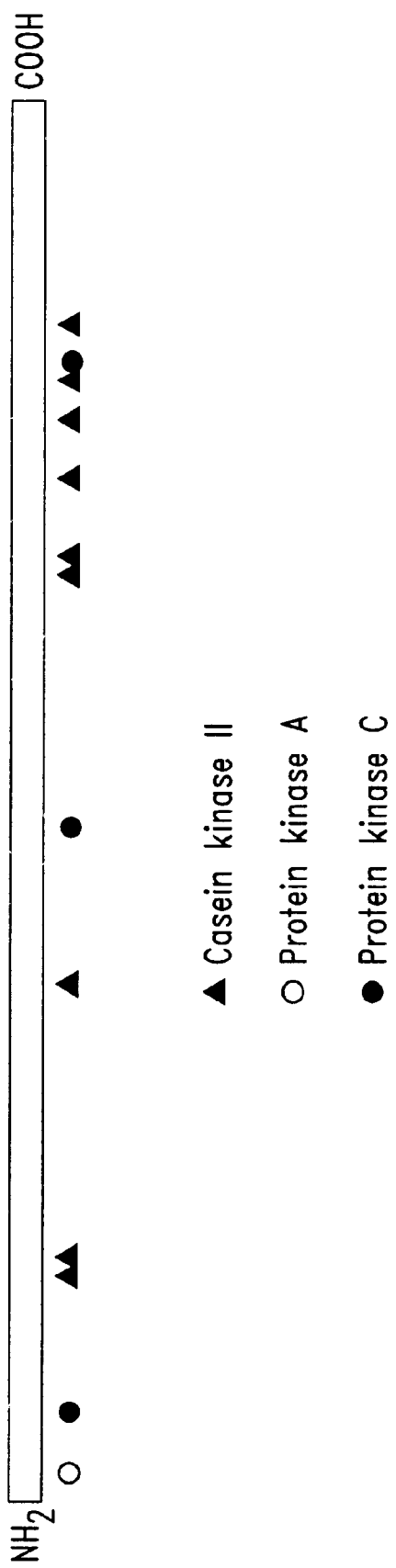

FIG. 39 is a diagrammatic representation of predicted p62 phosphorylation sites.

SEQ ID NO:1 is a cDNA sequence of FGF-2.

SEQ ID NO:2 is a cDNA sequence of 18 kD form of FGF-2.

SEQ ID NO:3 is an amino acid sequence of 18 kD form of FGF-2.

SEQ ID NO:4 is a cDNA sequence of hCG.

SEQ ID NO:5 is an amino acid sequence of hCG.

SEQ ID NO:6 is a cDNA sequence of the piecursor form of IL-1α.

SEQ ID NO:7 is an amino acid sequence of the precursor form of IL-1α.

SEQ ID NO:8 is a cDNA sequence of the mature form of IL-1α.

SEQ ID NO:9 is an amino acid sequence of the mature form of IL-1α.

SEQ ID NO:10 is a cDNA sequence of the precursor form of IL-1β.

SEQ ID NO:11 is an amino acid sequence of the precursor form of IL-1β.

SEQ ID NO:12 is a cDNA sequence of the mature form of IL-1β.

SEQ ID NO:13 is an amino acid sequence of the mature form of IL-1β.

SEQ ID NO:14 is a nucleotide sequence of FGF1.

SEQ ID NO:15 is an amino acid sequence of FGF1.

SEQ ID NO:16 is a nucleotide sequence of HIV Tat 72.

SEQ ID NO:17 is an amino acid sequence of HIV Tat 72.

SEQ ID NO:18 is a nucleotide sequence of HIV Tat 85.

SEQ ID NO:19 is an amino acid sequence of HIV Tat 85.

SEQ ID NO:20 is a forward amplification primer for the 18 kDa isoform of FGF-2.

SEQ ID NO:21 is a reverse amplification primer for the 18 kDa isoform of FGF-2.

SEQ ID NO:22 is a forward amplification primer for the wild type FGF-1.

SEQ ID NO:23 is a reverse amplification primer for the wild type FGF-1.

SEQ ID NO:24 is the N-terminal amino acid sequence recreated by the forward primer for wild type FGF-1.

SEQ ID NO:25 is a reverse amplification primer adding the HA epitope tag to FGF-1.

SEQ ID NO:26 is a reverse amplification primer adding the fig epitope tag to FGF-1.

SEQ ID NO:27 is a forward amplification primer for HIV Tat 72 or Tat 85.

SEQ ID NO:28 is a reverse amplification primer for wild type Tat 85.

SEQ ID NO:29 is a reverse primer encoding the C-terminal HA tag epitope.

SEQ ID NO:30 is a reverse primer for Tat 72.

SEQ ID NO:31 is a reverse primer encoding the C-terminal flg tag epitope.

SEQ ID NO:32 is a reverse primer for Tat 72 plus C-terminal HA-tag epitope.

SEQ ID NO:33 is a forward primer for IL-1α.

SEQ ID NO:34 is a reverse primer for IL-1α.

SEQ ID NO:35 is the flg peptide tag.

SEQ ID NO:36 is the influenza haemagglutinin peptide tau.

DETAILED DESCRIPTION OF THE INVENTION

As an aid to understanding the invention, certain definitions are provided herein.

"Export" of a protein refers to a metabolically active process, which may or may not be energy-dependent, of transporting a translated cellular product to the cell membrane or the extracellular space by a mechanism other than secretion via a canonical leader sequence. Further, "export," unlike secretion that is leader sequence-dependent, is resistant to brefeldin A (i.e., the exported protein is not transported via the ER/Golgi; brefeldin A is expected to have no direct effect on trafficking of an exported protein) and other similar compounds. As used herein, "export" may also be referred to as "non-classical secretion."

"Leaderless protein" refers to a protein or polypeptide that lacks a canonical leader sequence, and is exported from inside a cell to the extracellular environment. Leaderless proteins in the extracellular environment refers to a protein located in the extracellular space, or associated with the outer or inner surface of the cell membrane.

In contrast to an exported leaderless protein, a secreted protein has an N-terminal leader sequence or internal domain that mediates translocation into the ER/Golgi and is recognized by signal recognition proteins (SRP). Secreted proteins may also be found in the extracellular environment or associated with the membrane, but not as an integral membrane protein. The prototypic leader sequence has 15–25 amino acids, which has the following three regions: (1) an amino-terminal positively charged region, (2) a central hydrophobic region, and (3) a more polar carboxy-terminal region (see, von Heijne, *J. Membrane Biol.* 115:195–201, 1990). The central hydrophobic domain is important for secretion and is generally composed of 7–15 amino acids, such as leucine, isoleucine, valine, glycine, phenylalanine, methionine, threonine, serine, proline, cysteine, alanine, tyrosine, and tryptophan. The terms "signal sequence," "leader peptide," "leader sequence," and "canonical leader sequence" are used interchangeably herein.

"Transport molecule" refers to any protein involved directly or indirectly in the trafficking of leaderless proteins (e.g., a chaperonin). For example, a "transport molecule" may be one or more components of a cell transport pathway, which may be associated with the membrane surface, be integrally inserted into the membrane, or be associated with the membrane through a complex with another membrane or soluble protein. As used herein, a complex of one or more "transport molecules" may be interchangeably referred to as a "plasma membrane translocation apparatus," "cell transport pathway," "cell transport apparatus," and "transport apparatus."

"Complex" of two or more proteins refers to a specific association between proteins involving electrostatic or hydrogen bonding or the like, but not including a permanent covalent attachment. For example, a "complex" may be an antibody/antigen association or a leaderless protein/transport molecule association. Also, a "complex" may involve a transient covalent association of proteins, such as when one or more proteins of the complex are chemically modified. As used herein, protein "complex" may be used interchangeably with "protein binding" and "protein interaction."

"Modulator" refers to a molecule that can alter the export of a leaderless protein from a cell as compared to export in the absence of the modulator. In other words, a "modulator" alters export if there is a statistically significant change in the amount of protein detected extracellularly and/or intracellularly in an assay performed with a "modulator" compared to the assay performed without the modulator. Typically, the "modulator" will alter export of a leaderless protein by altering a protein complex. A "modulator" may alter a protein complex of two or more proteins by increasing, decreasing or completely disrupting protein binding. As used herein, "altered" binding refers to binding that has been prevented, dissociated, interfered with, or augmented. Furthermore, a "modulator" that alters a protein complex of a leaderless protein and a transport molecule may cause the export of a leaderless protein to be increased (enhanced), decreased (inhibited), or completely inhibited. For example, a "modulator" functions as an inhibitor of leaderless protein export when it prevents the interaction of a leaderless protein with one or more transport molecules or with a transport apparatus.

"Stability" of a protein complex refers to the natural, specific interaction or binding of two or more proteins that may be altered by a modulator. Altered "stability" may result when the protein binding is increased, decreased, or completely disrupted. A skilled artisan would appreciate that "stability" of protein interactions may be monitored by gel electrophoresis, competition assays, ELISA, co-precipitation, immunoaffinity columns, and other techniques known in the art. See, generally, Ausubel et al., 1995 Current Protocols in Molecular Biology, John Wiley & Sons, Inc., Boston, Mass.; and as illustrated in Example 14 herein.

Leaderless Proteins

As noted above, leaderless proteins are proteins that arrive in the extracellular environment, including at or in the cell membrane, but lack a signal sequence. A preliminary means to classify potential leaderless proteins is to compare the primary amino-terminal sequence with the canonical leader sequence, as described herein (von Heijne, supra). Any primary translation sequence of a protein that lacks such a leader sequence is a candidate exported leaderless protein.

Several leaderless proteins have been identified by virtue of their location in the extracellular environment, transport by a mechanism other than through the ER/Golgi, and lack of a canonical leader sequence. Leaderless proteins include fibroblast growth factor (FGF)-1, FGF-2 (SEQ ID NOS:1–3; cDNA, 18 kD form), interleukin(IL)-1α (SEQ ID NOS: 6, 7 and 8, 9; precursor, mature forms), IL-1 β (SEQ ID NOS: 10, 11, 12, and 13; precursor; mature forms), vas deferens protein/aldose reductase (GenBank Accession No. J105663): platlet-derived endothelial cell growth factor/thymidine phosphorylase (GenBank Accession No. M63193); ciliary neurotrophic factor (GenBank No. M29828); prothymosin a (GenBank Accession No. M14483); parathymosin (GenBank Accession No. M24398); galectin-l (GenBank No. J04456); galectin-3 (GenBank Accession No. M57710);L-29 (GenBank Accession No. M36682); Prostate carcinoma tumor antigen (GenBank Accession No. 1,78132); transglutaminase (GenBank Accession No. D90287); ATP synthase alpha subunit (GenBank Accession No. X59066); ATP synthase beta subunit (GenBank Accession No. M27132); aminoacyl-tRNA synthetase fragments (GenBank Accession No. U89436, Wakasugi et al., Science 284:147–150, 1999); endothelial monocyte activating polypeptide (GenBank Accession No. U10117); thioredoxin (GenBank Accession No. AF106697); factor XIIIa (GenBank Accession No. M14354); mammary-derived growth inhibitor/fatty acid binding protein (GenBank Accession No. U57623); macrophage migration inhibitory factor (GenBank Accession No. M25639); lipocortin-1/annexin-1 (GenBank Accession No. X05908); rhodanase (GenBank Accession No. D87292); HIV Tat (GenBank Accession No. M38429/M15390): interleukin 1 alpha (GenBank Accession No. X0253 1); interleukin 1 beta (GenBank Accession No. X02532); interleukin 16 (GenBank Accession No. M90391); interleukin 18 (GenBank Accession No. E17135). Within the context of the invention, leaderless proteins include naturally occurring proteins and fragments thereof as well as proteins that are engineered to lack a leader sequence and are exported, or proteins that are engineered to include a fusion of a leaderless protein, or fraction thereof, with another protein.

Other exported leaderless proteins may be identified by a two-part assay. First is identification of a protein in the extracellular environment, including at or in the membrane. For this assay, test cells expressing a leaderless protein are necessary. The test cells may produce the protein naturally or recombinantly from a transfected expression vector. Preferably, the test cells will express the protein naturally, but have increased levels of the leaderless protein due to additional expression from the transfected expression vector. For example, for FGF-2 expression, COS cells are preferred for transfection, and for IL-1 expression, THP-1 and P388D$_1$ cells are preferred. As those of skill in the art will appreciate, even test cells that do not naturally produce (i.e., chromosomally encode) a leaderless protein of interest, the cells may be readily transfected with an appropriate expression vector to produce the desired protein. This may be necessary when assaying for virally-derived proteins, such as HIV tat.

Following expression, the protein is detected by any one of a variety of well known methods and procedures. Such methods include staining with antibodies in conjunction with flow cytometry, confocal microscopy, image analysis, immunoprecipitation of cell medium, western blot of cell medium, ELISA, 1- or 2-D gel analysis, HPLC, FPLC, surface labeling (e.g., biotinylation) or bioassay. A convenient assay for initial screening is ELISA. Any candidate leaderless protein may be confirmed by one of the other assays, preferably by immunoprecipitation of cell medium following metabolic labeling. Briefly, cells expressing a potential leaderless protein are pulse labeled for 15 minutes with $^{35}$S-methionine and/or $^{35}$S-cysteine in methionine and/ or cysteine free medium, and then chased in medium supplemented with excess non-radioactive methionine and/or cysteine. Cells are sedimented by centrifugation, such as in a microfuge, and the cell supernatant media fractions are separated from the cell fraction. Lysis buffer (1% NP-40, 0.5% deoxycholate (DOC), 20 mM Tris, pH 7.5, 5 mM EDTA. 2 mM EGTA, 10 nM PMSF, 10 ng/ml aprotinin, 10 ng/ml leupeptin, and 10 ng/ml pepstatin) is added to the cell fraction, which may be a cell extract or cell membranes, and to the cell supernatant fraction. Antibody to the candidate leaderless protein is added and following incubation in the cold, a precipitating second antibody or immunoglobulin binding protein, such as protein A-Sepharose® or GammaBind™-Sepharose®, is added and further incubated. In parallel, as a control, a vector encoding a cytosolic protein is co-transfected and an antibody to the cytosolic protein is used for immunoprecipitation (IP). Immune complexes are then sedimented and washed with ice-cold lysis buffer. Complexes are further washed with ice-cold IP buffer (0.15 M NaCl, 10 mM Na-phosphate, pH 7.2, 1% DOC, 1% NP-40, 0.1% SDS). Immune complexes are dissociated directly in SDS-gel sample buffer and each protein is separated by SDS-PAGE. The percentage of acrylamide will depend upon the molecular weight of the leaderless protein. The gel is processed for fluorography, dried, and exposed to X-ray film. In one embodiment, proteins that are expressed at higher levels in the cell supernatant, as compared to the cytosolic protein control are candidate leaderless proteins that are exported.

The second: part of an assay to identify potential exported leaderless proteins is identification of brefeldin A-resistant export. Brefeldin A-resistant export indicates that a protein is being transported independent of the leader sequence-mediated pathway of the ER/Golgi. Brefeldin A-resistant protein export in test cells may be measured subsequent to or concurrent with the first part of identifying extracellularly located protein(s). Briefly, cells are transfected with an expression vector directing expression of a leaderless protein. Approximately 2 days later, the transfected cells are metabolically pulse-labeled for 15 minutes or longer with $^{35}S$ methionine and $^{35}S$-cysteine in methionine and cysteine free media. Label is removed, and the cells are further incubated in medium containing 5–15 µg/ml brefeldin A. For quantitation of FGF-2 export, for example, 25 µg/ml heparin is added to the chase medium. Lack of statistically significant reduction in leaderless protein export indicates that protein export is brefeldin A resistant. Alternatively, other compounds that disrupt ER/Golgi-mediated secretion may be used instead of brefeldin A.

Novel leaderless proteins that are exported may also be identified in an expression library. In such a method, a cDNA library from a tissue or cell source is constructed in a vector such that a fusion protein is generated with a reporter protein or peptide tag. The reporter or tag can be any protein that allows convenient and sensitive measurement in conditioned media and does not interfere with the export of the fusion protein. For example, β-galactosidase, alkaline phosphatase, and the FLAG® (Sigma, St. Louis, Mo.) epitope may be used. Furthermore, multiple tags may be used to allow detection by, for example, a sandwich assay.

In general, a vector may contain a strong promoter to drive expression of the cDNA-fusion genes and an appropriate origin of replication for the host cell. The cDNA library is transfected into host cells (e.g., COS cells) by any of the methods described herein or other known methods. Any host cell that is capable of non-classical (i.e., leaderless protein) secretion and is compatible with the vector may be used. Host cells can include animal cells, such as COS, CHO, yeast, and others. To facilitate recovery of particular cDNAs, each well of a multi-well plate containing cells is transfected with the library at a low multiplicity, such as 10 recombinant vectors per cell. Cell supernatant from each well is assayed for the presence of the fusion protein containing the reporter or tag. In addition, brefeldin A-resistant export is assessed to confirm that the transport is through a pathway other than the leader sequence-mediated pathway. Cells expressing a protein showing brefeldin A-resistant export are isolated, and the pool of vector(s) from each well are amplified, or isolated and propagated. The pool of vector(s) recovered from each well is then transfected into fresh host cells at a low multiplicity and the selection procedure repeated. Each round of transfection and selection should enrich for a cDNA encoding for an exported leaderless protein. The positive cDNA clones may be characterized, such as by DNA sequencing, tissue expression patterns, and the like.

In yet another assay to detect novel leaderless proteins, a sample is prepared from conditioned media, animal serum, or other biological fluid. The sample is passed over a column to remove all glycosylated proteins/peptides (e.g., a WGA column). Silver staining or fluorography (if metabolically labeled) detects the remaining proteins. The remaining proteins would either be secreted through the ER/Golgi and not posttranslationally modified, or may be candidate leaderless (exported) proteins or trafficking components of leaderless proteins. The candidate proteins may then be subjected to microsequencing.

Transport Molecules

This invention provides modulators of leaderless protein export wherein the modulator may interfere with or enhance the binding of a leaderless protein to a transport molecule. The transport molecule may be a single protein, a complex of proteins, or part of a larger complex. For example, as described herein, α subunit of the multi-unit $Na^+/K^+$ ATPase, gastrin binding protein/alpha subunit of mitochondrial fatty acid β-oxidation multienzyme complex (p70, GenBank Accession Nos. U4627/D16480), phosphotyrosine-independent ligand of the SH2 domain of p56lck (p62, GenBank Accession No. U4675 1), mitochondrial fatty acid β-oxidation trifunctional protein β subunit (TP-β) (p48, GenBank Accession No. D16481), actin related protein 3 (Arp3) (p48, GenBank Accession No. U29610), K-glypican (GenBank Accession No. X83577), tubulin (p50, GenBank Accession No. AF081484) are molecules that bind directly or indirectly to leaderless protein. As will be appreciated by a person of skill in the art, any functional variant, fragment, or derivative of the transport molecules are encompassed by the present invention. In this regard it should be noted that polypeptides that are functionally equivalent in their role as leaderless protein trafficking components are also transport molecules within the context of the present invention and are those molecules which are identifiable via the various assays described herein as well as equivalent assays. Accordingly, within the scope of the present invention are conserved domains which contribute to this functional aspect.

As shown herein, the $Na^+/K^+$ ATPase mediates transport of leaderless proteins. This ATPase is an integral membrane protein of eukaryotic cells and is responsible for the transport of sodium and potassium ions across the cell membrane using ATP as the driving force. The $Na^+/K^+$ ATPase consists of an a, P, and 6 subunit. In mammals, there are at least four known isoforms of the α subunit and three known isoforms of the β subunit. The α1 subunit is fairly ubiquitously expressed, being detected in virtually all rat tissues examined (Shyjan and Levenson, *Biochem.* 28:4531. 1989). As shown herein, FGF-2 and IL-1 interact with the axl subunit (see, Examples) as visualized by co-immunoprecipitation of the two proteins using anti-FGF-2 or anti-IL-1 and anti-α1 subunit antibodies. As well, export is sensitive to treatment of cardenolides, such as ouabain. Verification of the interaction is obtained by showing that co-overexpression of the α1 subunit dramatically slows the rate of FGF-2 export compared to control transfected cells. In addition, FGF-2 and IL-1 are shown by co-immunoprecipitation to interact with the α2 and α3 subunits, which are isoforms of the α subunit. Furthermore, overexpression of the α2 or α3 subunits also slows the rate of FGF-2 export.

Other ion channels may function as transport molecules or as part of a transport complex. Well known ion channels, in addition to $Na^+/K^+$ ATPase, include $Ca^+$ ATPase, $H^+/K^+$ ATPase, $Na^+$ channel, $Cl^-$ channel and $K^+$ channel. The involvement of these channels in transport of leaderless proteins may be assessed by treating cells exporting one or more leaderless proteins with a modulator of channel activity. Some known modulators that function as inhibitors of these channels are listed below.

anti-leaderless protein antibodies, but not by control antibodies, may be isolated and subjected to analysis and subsequent identification. In general, the protein will be subjected to partial amino acid sequence analysis and either a sequence match with a known protein is made, or a clone containing the sequence is isolated by standard recombinant DNA technologies and cloning procedures (e.g., hybridization of a degenerate probe on a library, generate antibodies and immunoscreen an expression library, or amplification of the sequence). Verification of a specific interaction may be made by one of several methods, including overexpression of the transport molecule or mutants of the molecule(s) and demonstrating that export is altered, co-immunoprecipitation of the transport and leaderless protein using anti-transport molecule antibodies, in vitro interactions assayed by western blots, ELISA and the like.

Alternatively, additional transport molecules may be identified by other methods, such as yeast two-hybrid system or transfection of a leaderless fusion protein followed by isolation of the fusion protein. Briefly, in a two-hybrid system, a fusion of a DNA-binding domain-leaderless protein (e.g., GAL4-FGF-2 fusion) is constructed and transfected into a cell containing a GAL4 binding site linked to a selectable marker gene. A library of cDNAs fused to the

| $Na^+/K^+$ ATPase Inhibitors | $Ca^+$ ATPase Inhibitors | $H^+/K^+$ ATPase Inhibitors | $Na^+$ Channel Blockers | Cl Channel Blockers | $K^+$ Channel Blockers |
|---|---|---|---|---|---|
| Ouabain | Cyclopiazonic Acid | Bafilomycin | Amiloride | N-Phenyl-anthranillic Acid | Diazoxide |
| Ouabagenin | Nifedipine | | Benzamil HCl | R (+)-1AA-94 5-Nitro-2-(3-phenylpropyl-aminobenzoic acid) | Gilbenclamide |
| Digoxin | Verapamil | | | | |
| Digoxigenin | Trifluroperazine | | | | |
| Digitoin | Thapsigargin | | | | |
| Digitoxigenin | | | | | |

These modulators may be assayed for their ability to decrease or otherwise modulate the export of any of leaderless protein, such as FGF-2, IL-1, and HIV tat. In an exemplary assay, a cell line that exports a leaderless protein (e.g., THP-1 cells export IL-1β) is seeded in 48 well tissue culture plates. When export of the protein is induced (e.g., by addition of LPS for IL-1β) or when the cells have recovered, a panel of ion channel inhibitors is added to individual wells for approximately 4–24 hours. At the end of this incubation period, cell supernatant is removed and assayed by any of the assays described herein for the leaderless protein. An modulator that decreases the amount of export identifies one or more components of a particular ion channel as a candidate transport molecule or cell transport apparatus.

Additional transport molecules of leaderless proteins may be identified by a variety of methods, including isolation after binding to a leaderless protein. Briefly, cells expressing and exporting a leaderless protein are metabolically labeled for a short period of time. The label is optionally chased, and cell and media fractions are immunoprecipitated with anti-leaderless protein antibodies. The antibodies may be monoclonal, a mixture of different monoclonal antibodies, or polyclonal antibodies. Immune complexes are collected and fractionated by PAGE. Libeled proteins. precipitated by GAL4 activation domain is also constructed and co-transfected. When the cDNA in the cDNA-GAL4 activation domain fusion encodes a protein that interacts with FGF-2, the selectable marker is expressed. Cells containing the cDNA are then grown, the construct isolated and characterized. Verification of specific interaction is made as described above.

In another method to identify transport proteins, a fusion protein is constructed comprising a leaderless protein or fragment thereof and a tag peptide or protein (e.g., green fluorescent protein, (GFP); glutathione-S-transferase, GST), which tag may be bound by an antibody or other molecule (e.g., glutathione) or detected by fluorescence. A vector encoding the fusion protein is transformed into bacteria. The fusion protein is purified. For example, a GST-FGF-2 fusion protein in pGEX-4T-3 (Pharmacia, Uppsala. Sweden) is induced by IPTG and purified using glutathione-beads (see, Kaelin et al., *Cell* 64:521. 1991). Cells that express transport proteins may be metabolically labeled. Cell extracts and/or cell membranes are incubated with GST-FGF2 charged glutathione-Sepharose beads. Alternatively, the fusion protein may be immunoprecipitated or the like. Unbound protein is washed away, and bound protein is eluted. The bound proteins may be further fractionated by, for example, gel electrophoresis. The isolated proteins may then be used for raising antibodies, amino acid sequence analysis, and in vitro tests as described herein. Clones encoding the bound proteins may be isolated by any one of a variety of standard methods, including immunoscreening of an expression library, probe hybridization where the probe is based on a partial amino acid sequence, and other known methods.

Antisense expression libraries may also be utilized to indentify transport molecules. In this regard, cells expressing an exported protein for which an assay system exits or which may be designed is transfected with an antisense expression library. The overexpressed antisense mRNA reduces synthesis of a cellular protein necessary for export and as a consequence the level of the exported protein detected extracellularly (media or cell surface) is reduced. Once detected, the antisense cDNA is isolated by any one of a number of possible techniques and the sequence may be determined.

As shown herein, several candidate transport molecules have been found to complex with a GST-leaderless protein fusion. One such protein, K-glypican, is part of a growing family of cell surface heparin sulfate proteoglycans (HSPGs) that play a role in regulating cellular proliferation, differentiation, and migration. The core polypeptide of the HSPGs is typically sulfated and some of these HSPGs have been shown to interact with the leaderless protein FGF-2, which may even facilitate FGF-2 binding with its receptor (see Schlessinger, *Cell* 83:357, 1995). In addition, the sulfation of the HSPGs is considered to be the domain that interacts with FGF-2 (see Schriever el al., *Biol. Chem.* 378: 701, 1997). It is demonstrated here for the first time that K-glypican (or a protein comprising the leaderless protein binding region thereof) can form a complex with FGF-2. Also. in contrast to other glypicans, the results described herein indicate that the core polypeptide sequence of K-glypican is the FGF-2 interactive domain. Another protein, which is homologous to gastrin binding protein (disclosed in GenBank as cysteine-rich FGF receptor associated protein. Accession No. U83249, and as FGF-2 binding protein, Accession No. AJ003123), is shown herein to complex with the GST-FGF fusion protein. This protein is also homologous to TP-α (GenBank Accession No. P40939), α subunit of the mitochondrial fatty acid oxidation protein complex (i.e., mitochondrial trifunctional protein) (see Ushikubo et al., *Am. J. Hum. Genet.* 58:979, 1996). The identification of K-glypican and homologs of gastrin binding protein as proteins capable of complexing with FGF-2 indicates that these proteins may play a role in the export of FGF-2 as well as other leaderless proteins.

In addition to K-glypican and gastrin binding protein, the GST-FGF fusion protein was used to isolate and identify other potential transport molecules not previously known to interact with leaderless proteins or to be involved in export. One protein that forms a complex with the GST-FGF fusion protein is p62, which was initially identified as a phosphotyrosine-independent ligand of the SH2 domain of the kinase p56$^{lck}$ and later identified as a ubiquitin binding protein as well (see Vadlamudi et al., *J. Biol. Chem.* 271:20235, 1996). Protein p62 is a cytoplasmic protein that may serve as a common signal transduction molecule, and with the present results, may be involved in the export of leaderless proteins. Another protein that complexes with the GST-FGF fusion protein is a second subunit of the mitochondrial fatty acid oxidation protein complex, TP-β (p48) (GenBank Accession No. D16479)(see Kamijo et al., *J. Biol. Chem.* 268:26452, 1993).

Another protein that was found to interact with the GST-FGF fusion protein was actin-related protein, Arp3. In a cell, Arp3 associates with Arp2 to form the Arp2/3 complex, which is involved as a nucleator of actin polymerization at the inner surface of the cell membrane to promote lamellipodial protrusion (i.e., the formation of protrusions are most likely the driving force of cell locomotion) (see Welch et al., *J. Biol. Chem.* 138:375, 1997). Thus, cellular locomotion and transport apparatus proteins may be coupled to deliver the leaderless proteins to specific sites external to or on the outer surface of the cell to signal, differentiation and/or proliferation of neighboring cells.

In another method, membrane components of the export pathway are identified. Briefly, cell membrane fractions are prepared according to well-known methods (e.g., Biomembranes, Methods in Enzymology vol 172; Klein et al., *Growth Factors* 13:219, 1996). To reduce non-specific association of the leaderless protein with proteoglycans, cells can be grown in a medium containing 25 mM sodium chlorate (Guimond et al., *J. Biol. Chem.* 268: 23906, 1993). Isolated cell membranes are incubated with the leaderless protein, such as FGF-2, and solubilized. Complexes of FGF-2/membrane components may be immunoprecipitated with anti-FGF-2 antibodies. The leaderless protein/transport molecule complex may be assessed for stability in a variety of assays known in the art, such as competition assays (see Example 14), gel electrophoresis, and immunoaffinity columns. Optionally, prior to immune precipitation, membranes may be crosslinked, such as with a reversible crosslinking agent, so as to more permanently maintain the protein interactions during analysis. Characterization of the components by SDS-PAGE will allow size determination. Proteins may be visualized by autoradiography (if cells are radiolabeled) or by staining (e.g., Coomassie blue or silver stain). Isolated proteins may be subjected to amino acid sequence analysis to facilitate molecular cloning.

Yet another method for identifying and isolating transport proteins is by virtue of homology or sequence similarity to export proteins in other organisms, such as yeast and bacteria. For example, export proteins in yeast are known (NCE2, Cleves and Kelly, *J. Cell Biol.* 133:1017, 1996, GenBank Accession No. U 41659; NCE3, Cleves and Kelly, ibid., GenBank Accession No. U 52369; and NCE1, Cleves and Kelly, ibid., GenBank Accession No. U 41658). Non-stringent hybridization of the yeast genes to mammalian cDNA libraries can be used to identify similar gene sequences (see Ausubel et al., supra). These sequences can be experimentally shown to function homologously by virtue of interaction with leaderless proteins, by conferring transport capability on a cell lacking the corresponding gene, or by other methods described herein.

In addition to the yeast export proteins, a secretion system in *E. coli*, Yersinia spp., and Shigella spp. for the transport of leaderless proteins (Salmond and Reeves, *TIB* 18:7–12, 1993) may be used to screen for sequence similarity. At least seven proteins responsible for export in *E. coli* have been identified (Jarvis et al., *Proc. Natl. Acad Sci. USA* 92:7996, 1995; Bost and Belin, *EMBO J.* 14:4412, 1995). DNA probes from the locus hybridize to genomic DNA of pathogens from other genera (McDaniel et al., *Proc. Natl. Acad. Sci. USA* 92:1664, 1995). DNA probes from these *E. coli* genes, as well as the homologous Ysc genes of Yersinia and Mxi./Spa genes of Shigella, may be used to detect homologues in other species, including mammalians.

In preferred embodiments, subdomains of transport molecules are used in assays for identifying modulators of the interaction with a leaderless protein. For example, see Example 20, wherein the N-terminal domain of p62 is identified as important for FGF-2 interaction as is the indication that phosphorylation plays a role in protein export. Accordingly, analyzing and modulating the phosphorylation levels of the various transport molecules may have a significant impact on the control of protein export.

For transport molecules that are transmembrane bound, both a cytosolic and an anchored subdomain are constructed. Other methods to redirect the protein to a different subcellular fraction may also be used. Merely by way of example, the $Na^+/K^+$ ATPase $\alpha1$ subunit lacking a transmembrane domain(s) is constructed in an expression vector. An FGF-2 construct is co-transfected, and the interaction between FGF-2 and the $\alpha1$ fragment is assessed. Alternatively, $\alpha1$ fragments may be anchored in the membrane. Because the $\alpha1$ subunit generally does not insert into the plasma membrane of animal (vertebrate animals) cells in the absence of a $\beta1$ subunit, a fusion protein construct to direct the $\alpha1$ subunit to the cell surface is made. Briefly, a fusion protein, including the transmembrane region of another protein; such as VSV-G, is fused to the N-terminus of $\alpha1$ and various other deletions and truncations of $\alpha1$. To assist in detecting the $\alpha1$ subunit in the membrane, an extracellular region of a readily assayed protein, such as hCG-$\alpha$ (human chorionic gonadotropin), may be fused to the construct adjacent to the VSV-G transmembrane domain. Other reporter genes may be interchanged as long as the gene product is readily assayed (e.g., by antibody, staining, or enzymatic activity). hCG-$\alpha$ may be detected by antibody staining. When the $\alpha1$ subunit is verified to be inserted into the membrane, interaction with FGF-2 is assessed and export of FGF-2 is assayed by methods described herein.

Modulators (Inhibitors and Enhancers)

Candidate "modulators" (inhibitors and/or enhancers) may be isolated or procured from a variety of sources, such as bacteria, fungi, plants, parasites, chemical and small molecule libraries, random peptides, or the like. Potential modulators that function as inhibitors include compounds known to inhibit angiogenesis, inflammation, or other specific functions of leaderless proteins. For example, inhibitors of angiogenesis include Adriamycin, angiostatin, etoposide, ansacrino, camptothecin, $\epsilon$-(4-hydroxy-1-naphthalenyl)-2-proponoic acid derivatives, 2,5-di-test-butylhydroquinone, amiloride and derivatives, aurintricarboxylic acid, captopril, dioxopiperazines, methylprednisolone, suramin, and minocycline. Inhibitors of inflammation include 8-hydroxyquinoline, choline chloride, cyclopiazonic acid, indoprofen, monensin, nicotine, Mycostatin, verapamil, and thiamine. These and other inhibitors may be pleiotropic in their action and, as such, may be tested for their ability to alter export of many or all of the leaderless proteins. In addition to modulators with known function, other candidate inhibitors of protein export may be procured from chemical libraries, small molecule libraries, plants, fungi, and the like, by using assay methods as described herein. For example, modulators that function as inhibitors, which were found in small molecule and chemical libraries, include those identified in FIGS. 29A–29C herein, and derivatives and analogues thereof.

Modulators and potential modulators that inhibit or enhance leaderless protein export, and are useful as disclosed herein, also include derivatives, analogues and mimics of molecules and compounds with identified and potential modulatory effects. For example, derivatives, analogues and mimics of compounds known to inhibit angiogenesis, inflammation, or other specific functions of leaderless proteins are modulators or potential modulators within the context of the present invention. To cite a more specific example, for the purpose of illustration, derivatives, analogues and mimics of Adriamycin, Mycostatin, and atebrine are modulators and/or potential modulators within the scope of the present invention.

In preferred embodiments, modulators alter the interaction of a leaderless protein with a transport protein or protein complex. The modulator may act by preventing binding of the leaderless protein with the transport protein, by causing dissociation of the leaderless/transport protein complex, by decreasing the stability of the leaderless/transport protein complex, by increasing the stability of the leaderless/transport protein complex, or by another mechanism. The modulator may act directly or indirectly. For example, reduced or enhanced binding of $Na^+/K^+$ ATPase $\alpha1$, $\alpha2$, or $\alpha3$ subunits with FGF-2 or IL-1 will alter (i.e., reduce or eliminate) protein export. Such an modulator generally acts intracellularly or even within the membrane. In contrast, cardenolides (i.e., cardiac glycosides and aglycone derivatives) act extracellularly and reduce export of FGF-2, but the interaction between FGF-2 and the $Na^{30}/K^+$ ATPase $\alpha1$ subunit may not be altered.

In certain embodiments, the modulator of export is an antibody or fragment thereof that interacts with components of the transport machinery such as a translocation complex at the cell surface. Briefly, in this embodiment an antibody or fragment thereof may be directed to the cell surface machinery which allows the exported protein to escape the cell membrane.

Modulators should have a minimum of side effects and are preferably non-toxic. For some applications, modulators that can penetrate cells are preferred. Modulators should be specific for export and not merely inhibit metabolism, such as $NaN_3$.

For example, modulators that alter the export of ATP synthase are good candidates as inhibitors of angiogenesis that are not toxic to cells in general. ATP synthase is generally a cytoplasmic protein, but under hypoxic conditions, such as during tumor growth, cells may generate extra energy for angiogenesis in the form of ATP by exporting ATP synthase. Angiostatin, a protein fragment of plasminogen that inhibits angiogenesis, blocks endothelial cell growth by interacting with $\alpha/\beta$ subunits of the cell surface located ATP synthase and inhibit this enzyme's activity. Small molecules that mimic angiostatin would be toxic for cells because ATP synthase activity is required for all energy production in all tissues. However, modulators of the present invention are functionally equivalent to angiostatin because they simply alter ATP synthase (a leaderless protein) export without affecting activity. In a preferred embodiment, the modulator would be a small molecule that alters the export of ATP synthase by reducing or increasing complex formation with transport molecules or a cell transport pathway. In other embodiments, the mechanism of action is unimportant as long as ATP synthase export to the cell surface is decreased and classical secretion and protein translation are not substantially altered. Similarly, any other cell surface required activity that is not essential for survival, except in diseased cells, may be targeted with modulators that either inhibit or enhance export of leaderless proteins. Accordingly, the present invention provides assays for identifying such ATP synthase modulators. In brief, one such assay utilizes ATP synthase in an expression construct either alone or as a tagged fusion protein. A cell would be transformed with this expression cassette and the cell would be treated with the candidate compound and the presence of ATP synthase on the cell surface would be determined.

Also provided herein are ribozymes that cleave leaderless protein and/or transport molecule encoding mRNA, and nucleic acid molecules that are complementary to the coding strand or the mRNA encoding leaderless protein and/or transport molecule. The expression of antisense RNA molecules will act to directly block the translation of mRNA by binding to targeted mRNA and preventing protein translation. The expression of ribozymes, which are enzymatic RNA molecules capable of catalyzing the specific cleavage of RNA may also be used to block protein translation. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RNA sequences. RNA molecules may be generated by transcription of DNA sequences encoding the RNA molecule.

Nucleic acids and oligonucleotides for use as described herein can be synthesized by any method known to those of skill in this art (see, e.g., WO 93/01286, U.S. application Ser. No. 07/723,454: U.S. Pat. No. 5,218,088; U.S. Pat. No. 5,175,269; U.S. Pat. No. 5,109,124). Identification of oligonucleotides and ribozymes for use as antisense agents and involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., Tetrehedron Lett. 28:3539–3542, 1987; Miller et al., J. Am. Chem. Soc. 93:6657–6665, 1971; Stec et al., Tetrehedron Lett. 26:2191–2194, 1985; Moody et al. Nucl. Acids Res. 12:4769–4782, 1989; Uznanski et al., Nucl. Acids Res., 1989; Letsinger et al., Tetrahedron 40:137–143, 1984; Eckstein, Annu. Rev. Biochem. 54:367–402, 1985; Eckstein, Trends Biol. Sci. 14:97–100, 1989; Stein, In: Oligodeoxynucleotides. Antisense Inhibitors of Gene Expression, Cohen, Ed, Macmillan Press, London, pp. 97–117, 1989; Jager et al., Biochemistry 27:7237–7246, 1988).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to. Burch; U.S. Pat. No. 5,087,617 to Smith and Clusel et al. Nucl. Acids Res. 21:3405–3411, 1993, which describes dumbbell antisense oligonucleotides). Triplex molecules refer to single DNA strands that bind duplex DNA forming a colinear triplex molecule, thereby preventing transcription (see, eg., U.S. Pat. No. 5,176,996 to Hogan et al. which describes methods for making synthetic oligonucleotides that bind to target sites on duplex DNA).

Targeting leaderless protein or transport molecule with antisense nucleotides will decrease expression, as antisense nucleotides have been demonstrated to be useful within the context of decreasing AUG initiated MIF concentrations. See, e.g. Takahashi et al., Microbiol. Immunol. 43(1):61–67, 1999 and Takahashi et al. Mol. Med. 4:707–714, 1998. Particularly useful antisense nucleotides and triplex molecules are molecules that are complementary to or bind the at least the first 10 nucleotides of the sense strand of DNA or mRNA that encodes a leaderless protein or transport molecule, or which binds a region N-terminal of the predicted AUG-initiation site of the targeted gene. Thus, the present invention provides nucleic acid molecule-based modulators that alter leaderless protein export.

Assays for Detecting Modulators of Leaderless Protein Export

Modulators of export of a leaderless protein are identified by an assay, such as the assays described herein. Briefly, in a preferred assay, a cell expressing a leaderless protein is contacted with the candidate compound and the amount of leaderless protein detected as an extracellular protein is compared to the amount detected in the absence of the candidate compound. In another embodiment, a cell expressing a leaderless protein is contacted with a candidate compound and the amount of leaderless protein extracellularly or intracellularly is detected and compared to the amount detected in the absence of the candidate compound. Additionally, extracellular and/or intracellular levels of a leaderless protein may be detected individually, sequentially, and concomitantly. One of ordinary skill in the art will readily appreciate that while mammalian cells are exemplified herein, that any cell type may be utilized including, but not limited to, prokaryotic cells and plant cells. In one embodiment, the cells may be primary tumor biopsies or cells derived therefrom.

Within the context of the present invention, a preferred modulator should: (1) decrease or increase export of a leaderless protein and (2) not substantially inhibit secretion of a leader sequence-containing protein. In other embodiments the modulator should also alter the stability of a complex, where the complex is comprised of a leaderless protein and a transport molecule. Generally, test compounds will be assayed first for decreasing export of a leaderless protein. Successful modulators will be further assayed for the other desired characteristics. All candidate compounds may subsequently or concurrently be tested for enhanced leaderless protein export. Appropriate controls may be used to distinguish true and false positives or negatives.

In any of the assays described herein, a test cell may express the leaderless protein naturally or following introduction of a recombinant DNA molecule encoding the protein. Transfection and transformation protocols are well known in the art and include $CaPO_4$-mediated transfection, electroporation, infection with a viral vector, DEAE-dextran mediated transfection, and the like. Recombinant expression of the leaderless protein is preferred, whether or not the leaderless protein is expressed from the chromosome. As an alternative to the leaderless proteins described above, chimeric leaderless proteins (i.e., fusion of a leaderless protein with another protein or protein fragment), or protein sequences engineered to lack a leader sequence may be used. In similar fashion, the secreted protein and cytosolic protein may be naturally expressed by the host cell or expressed following transfection of a vector encoding the protein. The host cell can also express the leaderless protein as a result of being diseased, infected with a virus, and the like. Proteins that are secreted by virtue of a leader sequence are well known and include human chorionic gonadatropin (hCGα) (SEQ ID NO:3), growth hormone, hepatocyte growth factor, transferrin, nerve growth factor, vascular endothelial growth factor, ovalbumin, and insulin-like growth factor. Similarly, cytosolic proteins are well known, including actin and other cytoskeletal proteins, and enzymes such as protein kinase A or C, neomycin phosphotransferase, and β-galactosidase. The most useful cytosolic or secreted proteins are those that are readily measured in a convenient assay, such as ELISA or colorimetric assay. The three types of proteins (leaderless, secreted, and cytosolic) may be co-expressed naturally, be expressed recombinantly by co-transfection into the test cells, or be expressed separately by transfection into separate host cells. Furthermore, for the assays described herein, cells may either be stably transformed or express the protein transiently.

Leaderless protein expressed from a recombinant vector may be native protein, any isoform or allele, a fusion protein designed to aid detection of the protein, or any functional derivative, fragment, or variant thereof. For example, a fusion protein of FGF-2 and a polypeptide tag may be constructed. The polypeptide tag is a short sequence, usually derived from a native protein, which is recognized by an antibody or other molecule. Such polypeptide tags include without limitation hexa-histidine tag, FLAG® (Sigma), Glu-Glu tag (Chiron Corp., Emeryville, Calif.), KF3 tag (Chiron Corp.), T7 gene 10 tag (Invitrogen, La Jolla, Calif.), T7 major capsid protein tag (Novagen, Madison, Wis.), and HSV tag (Novagen). Other, similar systems may be used as long as the fusion protein containing the tag is exported. Other types of tags that are detectable may be used, such as full length proteins, polypeptides, or peptides. For example, GST or any sequence specifying an enzymatic activity may be fused to the leaderless protein. Such enzymes include β-galactosidase, chloramphenicol acetyl transferase, thioredoxin, alkaline phosphatase, luciferase, green fluorescent protein and color-shifted mutants of wild-type GFP (Clontech, Palo Alto, Calif.), and the like. The activity of each of these enzymes are readily assayed, or the proteins are detectable with available antibodies.

Merely by way of example and not limitation, a construct containing the 18 kD isoform of FGF-2 is described. Plasmid 18dx encodes the 18 kD isoform of FGF-2, which is derived from the wild-type human FGF-2 cDNA as previously described (Florkiewicz and Sommer, *Proc. Natl. Acad. Sci. USA* 86:3978, 1989). The FGF-2 sequence is truncated 11 bp 5' of the ATG codon for the 18 kD isoform. Thus, only the 18 kD form is expressed. A fragment containing the cDNA is inserted into pJC119, an SV40-based expression vector, which uses the SV40 late promoter to control expression of the inserted gene. (Sprague et al., *J. Virol.* 45:773, 1983.) It will be apparent that other expression vectors may be used interchangeably and that the choice of the vector will depend in part upon the host cell to be transfected. In this example, FGF-2 cDNA was expressed in COS cells using an SV40-based expression vector. COS cells are chosen because they normally express low levels of FGF-2 and, as such, possess the appropriate cellular machinery for export of this leaderless protein.

With regard to generation of a fusion protein, a gene encoding a leaderless protein may be fused to a DNA sequence encoding a polypeptide tag to aid in detecting export or identifying proteins that interact with the leaderless protein. For example, the FLAG® peptide is fused to HIV tat, FGF-1 and FGF-2. This peptide does not interfere with export of FGF-2. Alternatively, GST is fused to a leaderless protein such as FGF-2 and IL-1.

Other leaderless proteins described above may be used in these constructs. DNA molecules encoding these proteins may be obtained by conventional methods, such as library screening or PCR amplification and cloning, or obtained from the ATCC/NIH repository of human and mouse DNA probes. Nucleotide sequences of these proteins are generally available from the GenBank and EMBL databases, or from publications.

It will be recognized that other cell types, vectors, promoters, and other elements used for expression may be readily substituted according to well-known principles. At minimum, a vector construct containing the leaderless protein must have a promoter sequence that is active in the target cell. Optionally, and preferably, the construct contains an enhancer, a transcription terminator, poly(A) signal sequence, bacterial or mammalian origins of replication, and a selectable marker. Such vectors are chosen to be suitable for the species or tissue type of the transfected cell. The cell may be mammalian, avian, or other eukaryotic cell, including yeast or prokaryote in origin.

Mammalian cells suitable for carrying out the present invention include, amongst others, COS-1 (ATCC No. CRL 1650), BHK (ATCC No. CRL 6281), CHO (ATCC No. CCL 61), HeLa (ATCC No. CCL2), 293 (ATCC No. 1573), NS-1 (ATCC No. T1B18), Hep G2 (ATCC No. HB 8065), J774A.1 (ATCC No. TIB 67), HEC-1-A (ATCC No. HTB 112), HEC-1-B (ATCC No. HTB 113), 3T3 (ATCC No. CCL 92), D10.G4.1 (ATCC No. TIB 224), $P388D_1$ (ATCC No. CCL 46), 5637 (ATCC No. HTB 9), SK-HEP-1 (ATCC No. HTB 52), THP-1 (ATCC No. TIB 202), Caco-2 (ATCC No. HTB 37), MDCK (ATCC No. CCL 34). and Jurkat (ATCC No. TIB 152).

A wide variety of promoters may be used within the context of the present invention. The choice of promoter will depend, at least in part, on the recipient cell line for transfection. By way of examples, promoters such as the SV40 promoter described above, MoMuLV LTR, RSV LTR, adenoviral promoter, and cytomegalovirus (CMV) immediate early promoter or late promoter may be used. Inducible promoters, such as the TET on/off system (Clontech Life Technologies. Palo Alto, Calif.) and metallothionein gene promoter, may be used. A tissue specific or cell-type promoter may also be used, as long as it is activated in the target cell. For example, the immunoglobulin promoter can be used to express genes in B lymphocytes. Other tissue-specific promoters include those isolated from t-feeto protein, γ- and Δ-crystallin, α-actin, carcinoembryonic antigen, prostate-specific antigen, and tyrosinase promoters. Preferred promoters express the leaderless protein at high levels, preferably expression is at least equal to or greater than levels expressed from the chromosome.

Enhancer sequences, transcription terminators and selectable markers are well known in the art. Enhancer sequences may be included as part of the promoter region used or additionally included to improve expression from a particular promoter. Enhancer sequences from CMV-IE, RSV LTR, SV40, and others may be used. Transcription terminators are sequences that stop RNA polymerase-mediated transcription. The poly(A) signal may be contained within the termination sequence or incorporated separately. A selectable marker includes any gene that confers a phenotype on the host cell that allows transformed cells to be identified and preferably allows a growth advantage under specified conditions. Suitable selectable markers for bacteria are well known and include, for example, resistance genes for ampicillin, kanamycin, and tetracycline. Suitable selectable markers for mammalian cells include hygromycin, neomycin, genes that complement a deficiency in the host (e.g., thymidine kinase and TK⁻ cells), and others well known in the art.

Once a test cell (or cells) has been constructed or procured, an export modulator (either inhibitor or enhancer) may be identified by a cell-based screening assay, or an in vitro binding assay where one or more isolated transport molecule(s) and one or more isolated leaderless protein(s) form a complex or otherwise associate. It will be readily apparent that these assays are adaptable for concurrently measuring the level of leaderless proteins export, leader sequence-mediated protein secretion, and cytosolic protein (s). In general, specific reagents (e.g., antibodies and enzymatic substrates) for these other proteins are substituted for reagents to detect export of leaderless proteins.

Assays to detect export of leaderless protein, leader sequence-mediated protein secretion, and cytosolic protein in a cell-based assay include immunoprecipitation of proteins labeled in a pulse-chase procedure, ELISA, 1- and 2-D gels, protein stains (e.g., Coomassie blue), HPLC, western blot, biological assays, and phagokinetic tracts. In all these assays, test cells expressing and exporting a leaderless protein are incubated with and without the candidate modulator.

Immunoprecipitation is an assay, that may be used to detect altered export of leaderless proteins. Briefly, cells expressing a leaderless protein from an introduced vector construct are labeled with $^{35}$S-methionine and/or $^{35}$S-cysteine for a brief period of time, typically 15 minutes or longer, in methionine- and/or cysteine-free cell culture medium. Following pulse-labeling, cells are washed with medium supplemented with excess unlabeled methionine and cysteine plus heparin if the leaderless protein is heparin-binding. Cells are then cultured in the same chase medium for various periods of time. Candidate modulators are added to cell cultures at various concentrations. Cell culture supernatant is clarified and collected. Cell supernatants are incubated with anti-FGF-2 immune serum (i.e., polyclonal antibodies) or a monoclonal antibody, or with anti-tag antibody if a peptide tag is present, followed by a developing reagent such as *Staphylococcus aureus* Cowan strain I, protein A-Sepharose®, or Gamma-bind™ G-Sepharose®. Immune complexes are sedimented by centrifugation, washed in a buffer containing 1% NP-40 and 0.5% deoxycholate, EGTA, PMSF, aprotinin, leupeptin, and pepstatin. Precipitates are then washed in a buffer containing sodium phosphate pH 7.2, deoxycholate, NP-40, and SDS. Immune complexes are dissociated directly in SDS-gel sample buffer and separated by SDS-PAGE. The gel is processed for fluorography, dried, and exposed to x-ray film.

Alternatively, ELISA may be used to detect and quantify the amount of leaderless protein, secreted protein, and cytosolic protein present in cell supernatants. ELISA is preferred for detection in high throughput screening. Briefly, when FGF-2 is the test leaderless protein, 96-well plates are coated with an anti-FGF-2 antibody or anti-tag antibody, washed, and blocked with 2% BSA. Cell supernatant is then added to the wells. Following incubation and washing, a second antibody (e.g., anti-FGF-2) is added. The second antibody may be coupled to a label or detecting reagent, such as an enzyme or biotin. Following further incubation, a developing reagent is added and the amount of FGF-2 determined using an ELISA plate reader. The developing reagent may be a substrate for an enzyme coupled to the second antibody (typically an anti-isotype antibody) or for an enzyme coupled to strepltavidin. Suitable enzymes are well known in the art (e.g., horseradish peroxidasel, which acts upon a substrate (e.g., 2,2'-azino-di-3-ethylbenzthiazoline sulfonic acid, ABTS) resulting in a calorimetric reaction. It will be recognized that rather than using a second antibody coupled to an enzyme, the anti-FGF-2 antibody may be directly coupled to an enzyme or other equivalent detection reagent. If necessary, cell supernatants may be concentrated to increase the sensitivity of detection.

ELISA, or other solid support high density or chip arrays, may be readily adapted for screening multiple candidate modulators with high throughput assays. Briefly, for example, such an assay is conveniently cell based and may be performed in 96-well plates. If test cells naturally or stably express the leaderless protein, the cells are plated at 20,000 cells/well. If the cells do not naturally express the protein, transient expression is achieved by introducing a leaderless protein expression vector, such as by electroporation or $CaPO_4$-mediated transfection. For electroporation, 100 µl of a mixture of cells (150,000 cells/ml) and vector DNA (5 µg/ml) is dispensed into individual wells of a 96-well plate. The cells are electroporated using an apparatus with a 96-well electrode (e.g., ECM 600 Electroporation System, BTX, Genetronics, Inc.). Optimal conditions for electroporation are experimentally determined for the particular host cell type. Voltage, resistance, and pulse length are the typical parameters varied. Guidelines for optimizing electroporation may be obtained from manufacturers or found in protocol manuals, such as *Current Protocols in Molecular Biology* (Ausubel et al., 1995). Cells are diluted with an equal volume of medium and incubated for 48 hours. Electroporation may be performed on various cell types, including mammalian cells, yeast cells, bacteria, and the like. Following incubation, medium with or without modulator is added and cells are further incubated for 1–2 days. At this time, culture medium is harvested and assayed for protein by any of the assays described or incorporated herein. Preferably, ELFSA is used to detect the protein. An initial concentration of 50 µM modulator is tested If this amount gives a statistically significant reduction of export, the candidate modulator is further tested in a dose response.

Alternatively, co-culture systems may be utilized by incubating with a reporter cell type that reports the presence of a particular exported protein or the cell culture supernatant may be concentrated for analysis by electrophoresis. The proteins are separated by SDS-PAGE and transferred to a solid support, such as nylon or nitrocellulose. Leaderless protein is then detected by an immunoblot (see Harlow, *Antibodies: A Laboratory Manual*, Cold Spring Harbor Laboratory, 1988), using an antibody to the leaderless protein containing an isotopic or non-isotopic reporter group. These reporter groups include without limitation enzymes, cofactors, dyes. radioisotopes, luminescent molecules, fluorescent molecules and biotin. Preferably, the reporter group is $^{125}$I or horseradish peroxidase. The presence of horseradish peroxidase may be detected by incubation with a substrate such as ABTS. The detection assays described above are readily adapted for use with a leaderless protein engineered to contain a peptide tag. In such a case, an antibody that binds to the peptide tag is used. Other detection assays include size or charge-based chromatography, including HPLC, FPLC, affinity chromatography, and the like.

Alternatively, a bioassay may be used to quantify the amount of leaderless protein exported into the culture medium and to measure the intracellular levels of leaderless protein. For example, the bioactivity of the 18 kD FGF-2 protein of promoting cell growth may be measured by a cell proliferation assay, such as the incorporation of tritiated thymidine. Briefly, cells transfected with an expression vector containing FGF-2 are cultured for approximately 30 hours, during which time a candidate modulator is added. Following this initial incubation, cells are transferred to a low serum medium for a further 16 hours of incubation. The medium is harvested and clarified by centrifugation. The cells may be resuspended in a lysis buffer containing protease inhibitors to prepare cell extracts, or the cells may be resuspended in a solution to prepare cell membrane fractions as described herein. FGF-2 is enriched from the cell supernatant, cell extracts, and cell membrane fractions by binding to heparin-Sepharose® CL-6B and eluted with 1.5

M NaCl. Bioactivity of the FGF-2 is then measured by adding various amounts of the eluate to cultured quiescent 3T3 cells or endothelial cells. Tritiated thymidine is added to the medium and TCA precipitable counts are measured approximately 24 hours later. The amount of tritiated thymidine incorporated into the 3T3 or endothelial cells will reflect the level of FGF-2 export and allow a determination of the extracellular and/or intracellular levels of leaderless protein. Reduction of the vital dye MTT is an alternative way to measure proliferation. For a standard, purified recombinant human FGF-2 may be used. Other angiogenic leaderless proteins (e.g., FGF-1, PD-ECGF) may be assessed in a similar manner. Leaderless proteins displaying other functions may be assayed in other appropriate bioassays available in the art.

Other in vitro angiogenic assays include measuring proliferation of endothelial cells within collagen gel (Goto et al., *Lab Invest.* 69:508, 1993), co-culture of brain capillary endothelial cells on collagen gels separated by a chamber from cells exporting the leaderless protein (Okamure et al., *B.B.R.C.* 186:1471, 1992; Abe et al., *J. Clin. Invest.* 92:54, 1993), or a cell migration assay (see, Warren et al., *J. Clin. Invest.* 95:1789, 1995) which is also useful in measuring MIF activity and thus export.

Alternatively, or as a further assessment of candidate modulators, assays may be performed to analyze the extent of binding between a leaderless protein and a transport molecule or transport apparatus. A host cell expressing both the leaderless protein and transport protein endogenously, or following transfection, are treated with candidate modulators. The binding may be measured by a variety of different methods. A co-precipitation assay in which antibodies to either protein may be used to precipitate the leaderless protein/transport molecule(s) complex. The precipitate complexes are assayed by gel electrophoresis for disruption of the interaction or excess leaderless protein may be added to determine whether the complex with transport molecule(s) is enhanced or inhibited. The leaderless protein may be a fusion protein with a tag peptide, where anti-tag peptide antibodies may be used to precipitate the complex. As described above, the membrane bound $Na^+/K^+$ ATPase $\alpha 1$ subunit or fragment may be used in this assay.

An assay for identifying a modulator of export may be performed using isolated transport molecule(s) and leaderless protein. Isolated transport apparatus components are preferably obtained by recombinant expression and purified by standard methodologies. In a competition assay, for example the isolated components are mixed, along with any necessary cofactors, in the presence or absence of the candidate modulator. The extent of binding of the leaderless protein and transport molecule is measured. This competition assay may be conveniently performed on a solid support, such as in multi-well plates for an ELISA or on any solid support for high density or chip array analysis. For example, for an ELISA, the transport molecule is adsorbed to a solid support such as the wells of a 96-well plate. The leaderless protein, with or without candidate modulators, is added to the wells and incubated. Unbound protein is washed away and, for example, the presence of leaderless protein is detected by labeled antibody as described herein. Variations on this assay may be used. By way of illustration, the components may be attached to Biacore chips (Biacore, Uppsala, Sweden) or similar solid support detection device.

Modulator activity may be measured by in vivo models of disease. A cell that exports the leaderless protein of interest to the extracellular environment is introduced into a local milieu where the activity of the protein can be measured. In the case of a cell that exports, for example, ATP synthase, FGF-1, FGF-2, PD-ECGF, IL-1, thioredoxin, mammary-derived growth inhibitor, and/or Factor XIIIa, the cell will promote vascularization or angiogenesis, inflammation, clotting, or gliosis on neighboring cells. For example, in the case of a cell exporting FGF-1 or ATP synthase that is inoculated along with tumor cells, vascularization of the tumor will ensue. Accordingly, a modulator that inhibits FGF-1 or ATP synthase export will inhibit growth of the tumor. One skilled in the art will recognize that the export levels of the protein may be varied through the use of promoters of varying strength. As well, cells exporting the protein may be transformed stably or express the protein transiently. The site and route of administration depends in part upon the protein and its normal site of action.

When the transport molecule is $Na^+/K^+$ ATPase, a rubidium uptake assay may be performed to confirm that the inhibitor does not affect ions transport. Briefly, cells transfected with a vector expressing $Na^+/K^+$ AT-Pase are grown in the absence or presence of the inhibitor. Radioactive rubidium is added for a further short incubation. Cells are washed, extracted with base, neutralized and counted. An inhibitor that allows rubidium uptake that is not reduced by a statistically significant level compared to the control is useful within the context of this invention.

For leaderless proteins that cause cell motility, such as FGF-2 and MIF, a phagokinetic tract assay may be used to determine the amount of leaderless protein exported (Mignatti et al., *J. Cellular Physiol.* 151:81–93, 1992). In this assay, cells are allowed to migrate on a microscope cover slip coated with colloidal gold. Under dark field illumination, the gold particles appear as a homogenous layer of highly refringent particles on a dark background. When a cell migrates on the substrate, it pushes aside the gold particles producing a dark track. An image analyzer may be used to measure the length of the tracks. Under particular conditions, cell motility directly correlates with the amount of FGF-2 produced by the cells. The choice of the bioassay will depend, at least in part, by the leaderless protein tested.

In vivo assays may be used to confirm that a modulator affects export of eaderless protein. For measuring angiogenic activity, standard assays include the hicken chorioallantoic membrane assay (Aurbach et al., *Dev. Biol.* 41:391, 1974; Taylor and Folkman, *Nature* 247:307, 1982) and inhibition of angiogenesis in tumors. For some leaderless proteins, an assay measuring inhibition of tumor growth, such as in a murine xenogeneic tumor model, may be appropriate.

Inflammation-inducing leaderless proteins (e.g., IL-1, Dinarello, *J. Am. Soc. Hematology* 87:2095, 1996) may be measured by in vitro or in vivo assays. Briefly, an in vitro assay is performed by adding cell culture supernatant from cells exporting the protein to a murine T cell line, such as D10.G4.1, and assaying cytokine production or proliferation (Ichinose et al., *Cancer Immunol. Immunother.* 27:7, 1988). Cell supernatant may be added to IL-1 sensitive radiolabeled tumor cells and the release of radioactivity is determined. Alternatively, LPS can be used to induce IL-1β synthesis and release. In vivo inflammation assays include subcutaneous implants of a chamber containing cells exporting IL-1 and assessing infiltration of macrophages and fibroblasts (Hurtenbach et al., *J. Exp. Pathol.* 76111, 1995; Giller et al., *J. Immunol.* 1:1331, 1995; Xing et al. Am. *J. Respir. Cell Mol. Biol.* 10:148, 1994; Dawson et al., *Agents Actions* 38:247, 1993). Still other assays include hepatic and pulmonary animal models of granulomatosis inflammation due to injections of agents causing chronic inflammation (Allen et al., *J. Clin. Invest.* 76:1042, 1985; Matheny et al., *Growth Factors* 4: 17, 1990, Chensue et al., *J. Immunol.* 1:148, 1992).

In any of these assays, a compound that functions as a modulator alters export if there is a statistically significant change in the amount of protein detected extracellularly and/or intracellularly in the assay performed with the modulator, compared to the assay performed without the modulator. Preferably, a modulator reduces export of the leaderless protein by at least 50% even more preferably 80% or greater, and also preferably, in a dose-dependent manner. In addition, there should be no statistically significant effect on the appearance of secreted protein in extracellular environment or leakage from the cell of cytosolic protein. Preferably, there is less than a 10% alteration in the localization of these two protein types.

As shown in certain Examples and in FIGS. 29A–29C, a library of small molecules is screened for a modulator that decreases export. A number of compounds that inhibit export are re-tested at two different concentrations and also for inhibition of secretion of the leader sequence-containing protein, hCGα. Ten different compounds decrease FGF-2 export, but do not markedly affect hCGα secretion. Accordingly, similar assays may be carried out for detecting altered export of any leaderless protein.

In a logical extension of the assays described herein, lead small molecules once identified as modulators of export can themselves be attached to a solid support and used to screen for the molecular target of a specific small molecule thereby identifying additional trafficking pathway components. Further such small molecules could be attached to a chip or other highthroughput substrate and used to screen expression levels of their binding counterparts. In any of these assays the binding components may be eluted and characterized.

Administration

As described above, an modulator of leaderless protein export is useful for treating tumors, inhibiting angiogenesis, inhibiting inflammation, inhibiting cell migration, inhibiting proliferation of cells including smooth muscle cells that cause restenosis, and treating complications of diabetes, among other uses. In addition, modulators may limit viral, bacterial, or fungal infections. Treatment means that symptoms may be lessened or the progression of the disease or conditions halted or delayed. Cells to be treated are contacted with an modulator at a therapeutically effective dosage. Contacting may be effected by incubation of cells ex vivo or in vivo, such as by topical treatment, delivery by specific carrier, or by vascular supply.

The conjugates herein may be formulated into pharmaceutical compositions suitable for topical, local, intravenous and systemic application. Time release formulations are also desirable. Effective concentrations of one or more of the conjugates are mixed with a suitable pharmaceutical carrier or vehicle. The concentrations or amounts of the conjugates that are effective requires delivery of an amount, upon administration, that ameliorates the symptoms or treats the disease. Typically, the compositions are formulated for single dosage administration. Therapeutically effective concentrations and amounts may be determined empirically by testing the conjugates in known in vitro and in vivo systems, such as those described herein; dosages for humans or other animals may then be extrapolated therefrom.

Candidate tumors for treatment, as described herein, include those with receptors for FGF. Such tumors include, but are not limited to, melanomas, teratocarcinomas, ovarian carcinomas. bladder tumors, and neuroblastomas.

Other diseases, disorders, and syndromes are suitable for treatment. Diabetic complications, such as diabetic retinopathy, restenosis, polycystic kidney disease, and atherosclerosis are also candidates for such treatments. Cells in the eye, kidney and peripheral nerve, which are affected in diabetes, may be treated with the conjugates described herein. Viral, fungal, and bacterial infections may be treated.

Pharmaceutical carriers or vehicles suitable for administration of the conjugates provided herein include any such carriers known to those skilled in the art to be suitable for the particular mode of administration. In addition, the modulator may be formulated as the sole pharmaceutically active ingredient in the composition or may be combined with other active ingredients.

The compositions of the present invention may be prepared for administration by a variety of different routes. Local administration is preferred. The modulator may be mixed with suitable excipients, such as salts, buffers, stabilizers, and the like. If applied topically, such as to the skin and mucous membranes, the modulator may be in the form of gels, creams, and lotions. Such solutions, particularly those intended for ophthalmic use, may be formulated as 0.01%–10% isotonic solutions, pH about 5–7, with appropriate salts (see, e.g., U.S. Pat. No. 5,116,868).

Solutions or suspensions used for parenteral, intradermnal, subcutaneous, or topical application can include any of the following components: a sterile diluent such as water for injection, saline solution, fixed oil, polyethylene glycol, glycerine, propylene glycol or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of toxicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents such as glucose, polyethylene glycol, and polypropylene glycol and mixtures thereof. Liposomal suspensions may also be suitable as pharmaceutically acceptable carriers. These may be prepared according to methods known to those skilled in the art.

The modulator may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commnercially available surgical sponge (see, e.g., U.S. Pat. Nos. 3,956,044 and 4,045,238).

The modulators can be administered by any appropriate route, for example, orally, parenterally, intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors, restenosis, and infections will typically be treated by systemic, intradermal or intramuscular modes of administration.

The modulator is included in the pharmaceutically acceptable carrier in an amount sufficient to exert a therapeutically useful effect in the absence of undesirable side effects. It is understood that number and degree of side effects depends upon the condition for which the conjugates are administered. For example, certain toxic and undesirable side effects are tolerated when treating life-threatening illnesses, such as tumors, that would not be tolerated when treating disorders of lesser consequence. The concentration of conjugate in the composition will depend on absorption, inactivation and excretion rates thereof, the dosage schedule, and amount administered as well as other factors known to those of skill in the art.

The modulator may be administered one time, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The following examples are offered by way of illustration and not by way of limitation.

EXAMPLES

Example 1

CONSTRUCTION OF PLASMIDS EXPRESSING FGF-2

The expression vector containing the 18 kD isoform of FGF-2 is constructed as follows. The sequence of the 18 kD isoform of human FGF-2 is provided by plasmid 18dx (Florkiewicz and Sommer, *Proc. Natl. Acad. Sci. USA* 86:3978–3981, 1989). This vector only expresses the 18 kD isoform because the sequences upstream of the ApaI site located 11 bp 5' of the ATG codon initiating translation of the 18 kD FGF-2 isoform are deleted. Briefly, plasmid p18dx is linearized with ApaI and an oligonucleotide adapter containing an XVhoI site is ligated to the plasmid. The XhoI restriction fragment containing FGF-2 is purified and subcloned into the XhoI site of pJC119 (Sprague et al., supra).

An expression vector encoding hCG-cc (Guan et al., *J. Biol. Chem.* 263:5306–5313, 1988), which has a signal sequence, is used as a control to monitor proteins trafficked through the ER/Golgi.

Example 2

CELL CULTURE, TRANSFECTION, AND METABOLIC LABELING

COS cells obtained from the American Type Culture Collection (ATCC No. CRL 1650) are cultured overnight in a 48-well plate in DMEM supplemented with 10% fetal bovine serum, 2 mM L-glutamine, 1 mM sodium pyruvate, 100 nM nonessential amino acids, and 50 $\mu$g/ml gentamycin. The COS cells are then transfected with 2 $\mu$g/ml of CsCl-purified plasmid DNA in transfection buffer (140 mM NaCl, 3 mM KCl, 1 mM $CaCl_2$, 0.5 mM $MgCl_2$, 0.9 mM $Na_2HPO_4$, 25 mM Tris, pH 7.4. To each well, 300 $\mu$l of the DNA in transfection buffer is added. Cells are incubated for 30 minutes at 37° C., and the buffer is aspirated. Warm medium supplemented with 100 $\mu$m chloroquine is added for 1.5 hr. This medium is removed and the cells are washed twice with complete medium. Cells are then incubated for 40–48 hr. The plasmid 18dx is co-transfected with pMAM-neo (Clontech, Palo Alto, Calif.), which contains the selectable marker neomycin phosphotransferase. When 2 $\mu$g of p18dx are co-transfected with 10 $\mu$g of pMAMneo, greater than 70% of transfected cells express both FGF-2 and neo, as determined by immunofluorescence microscopy.

For an immunoprecipitation assay after transfection, the COS cells are metabolically pulse-labeled for 15 minutes with 100 $\mu$Ci of $^{35}$S-methionine and $^{35}$S-cysteine (Trans $^{35}$S-label, ICN Biomedicals, Irvine, Calif.) in 1 ml of methionine and cysteine free DMEM. Following labeling, the cell monolayers are washed once with DMEM supplemented with excess (10 mM) unlabeled methionine and cysteine for 1–2 minutes. Cells are then cultured in 2 ml of this medium for the indicated lengths of time and the cell supernatants are immunoprecipitated for the presence of leaderless protein. For the indicated cultures, chase medium is supplemented with modulator at the indicated concentrations.

Alternatively, for analysis by ELISA after transfection, the COS cells are washed once with 250 $\mu$l of 0.1 M sodium carbonate, pH. 11.4, for 1 to 2 minutes and immediately aspirated. A high salt solution may alternatively used. fhe cells are washed with media containing 0.5% FBS plus 25 Hg/ml heparin and then the cells are incubated in this same medium for the indicated lengths of time. For indicated cultures, chase medium is supplemented with a modulator. For cells transfected with vector encoding a protein containing a leader sequence, such as hCG-$\alpha$ or any other non-heparin binding protein, the carbonate wash and heparin containing medium may be omitted.

Example 3

INDUCTION OF IL-1$\alpha$ EXPORT

Either , $P388D_1$ or 5637 (human bladder carcinoma) cells are seeded at $1 \times 10^6$ cells/48-well in 0.5 ml RPMI 1640 containing 50 $\mu$g/ml gentamycin, 2mM L-glutamine and 15% FBS, and then incubated overnight at 37° C. in a humidified $CO_2$ chamber.

Cells are induced to export IL-1$\alpha$ by the addition of 1 $\mu$M ionomycin or other calcium ionophores, PMA, or 10 $\mu$g/ml LPS, and the like. Medium is removed. Cells are washed with the same medium containing 0.5% FBS, with or without test modulators, and incubated at 37° C. in a humidified $CO_2$ chamber for the indicated length of time. At the end of the incubation period, cell medium is harvested, centrifuged, and diluted 1:1 with (20 mL citrate, pH 6.0 containing 2% protease-free HSA, 2 mM EGTA, 0.5 $\mu$g/ml each leupeptin, pepstatin, aprotinin, 0.2 mM PMSF and 50 $\mu$M AEBSF. Medium is then either assayed immediately for IL-1$\alpha$ or frozen at −20° C.

Example 4

BREFELDIN-RESISTANT EXPORT OF FGF-2

Brefeldin A inhibits leader sequence-mediated protien secretion from the ER and Golgi. In contrast, export of a leaderless protein is not altered by treatment with brefeldin A.

COS cells are cultured in Dulbecco's Modified Eagle Medium (DMEM, University of California San Diego Core Facility) supplemented with 10% fetal bovine serum (Gemini Bioproducts, Inc.), 2 mM L-glutamine, 1 mM sodium pyruvate, 0.1 mM non-essential amino acids, 100 units/ml penicillin, and 100 units/ml streptomycin. An SV-40-based expression vector containing the wild type (human) cDNA encoding multiple FGF-2 isoforms (24, 23, 22 and 18-kD) has been described previously (Florkiewicz and Sommer, supra). Approximately $3\times10^5$ COS cells in a 60 mm tissue culture dish are transfected with 10 µg of CsCl-purified plasmid DNA mixed with 1.0 ml of transfection buffer (140 mM NaCl, 3 mM KCl, 1 mM $CaC'_2$, 0.5 mM $MgCl_2$, 0.9 mM $Na_2HPO_4$, 25 mM Tris pH 7.4; all from Sigma Chemical Company, Stl. Louis, Mo.). Under these co-transfection conditions using 2 µg of p18dx plus 10 µg pMAMneo, greater than 70% of transfected cells express both proteins, as determined by immunofluorescence microscopy. The ratio of plasmid DNA may be varied with an insignificant change in results. Forty to 48 hours post-DNA transfection COS cells are metabolically pulse-labeled for 15 minutes with 100 µCi of $^{35}$S-methionine and $^{35}$S-cysteine (Trans$^{35}$S-label, ICN Biomedicals, Inc.) in 1.0 ml of methionine-and cysteine-free DMEM. After pulse-labeling, the cell monolayers are washed once with DMEM supplemented with excess (10 mM) unlabeled methionine and cysteine (Sigma Chemical Company) and then cultured in 1.0 ml of the same medium (chase) for the indicated lengths of time. Cultures treated with brefeldin A include 15 µg/ml of brefeldin A in the chase medium. Chase medium is also supplemented with 25 µg/ml heparin (Sigma Chemical Company). Although heparin is not necessary to qualitatively detect FGF-2 export, it is necessary in order to quantitatively detect the export of FGF-2 in this assay.

Cell and medium fractions are prepared for immunoprecipitation essentially as described previously (Florkiewicz et al., 1991) except that 400 µl of lysis buffer without NaCl (1% NP-40, 0.5% deoxycholate, 20 mM Tris pH 7.5, 5 mM EDTA, 2 mM EGTA, 0.01 mM phenylinethylsufonyl fluoride, 10 ng/ml aprotiniul, 10 ng/ml leupeptin, and 10 ng/ml pepstatin) is added to the medium fraction clarified by microfuge centrifugation for 15 minutes at 4° C. before adding immune serum. Both cell and medium fractions are incubated with a 1:200 dilution of guinea pig anti-FGF-2 immune serum (prepared in our laboratory) at 21° C. for 40 minutes and then GammaBind G Sepharose® (Pharmacia LKB Biotechnology) is added for an additional 30 minute incubation. G-Sepharose-bound immune complexes are sedimented, washed three times with lysis buffer, and four times with ice cold immunoprecipitation wash buffer (0.15 M NaCl, 0.01 M Na-Phosphate pH 7.2, 1% deoxycholate, 1% NP-40, 0.1% sodium dodecyl sulfate). Immune complexes are dissociated directly in SDS-gel-sample buffer and then separated by 12% SDS-PAGE. The gel is processed for fluorography, dried and exposed to X-ray film at –70° C. For immunoprecipitations involving neomycin phosphotransferase (NPT), rabbit anti-NPT antibody (5 Prime-3 Prime, Inc., Boulder, Colo.) was used.

As shown in Florkiewicz et al., 1995 (supra), the export of 18 kD FGF-2 is brefeldin A-resistant and is energy dependent. Sample A was chased with medium alone, sample B was chased with medium supplemented with 25 µg/ml brefeldin A and sample C was chased with medium supplemented with 50 mM 2-deoxy-D-glucose and $NaN_3$. FGF-2 is exported to the medium by 2 hours. Brefeldin A had no substantial effect on this export. However, when $NaN_3$, a metabolic inhibitor, is present, export is substantially reduced. In contrast, hCG-α is secreted into the medium by 4 hours and is brefeldin sensitive and energy dependent. hCG-α (SEQ ID NOS: 4, 5) contains a hydrophobic leader (signal) sequence and as a consequence is secreted via the ER and Golgi.

Example 5

IMMUNOPRECIPITATION AND WESTERN BLOT ANALYSIS

Cell and conditioned medium fractions are prepared for immunoprecipitation essentially as described pieviously (Florkiewicz el al., *Growth Factors* 4:265–275, 1991; Florkiewicz et al., *Ann. N.Y. Acad. Sci.* 638:109–126) except that 400 µl of lysis buffer (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) is added to the medium fraction after clarification by centrifugation in a microfuge for 15 minutes. Cell or medium fractions are incubated with guinea pig anti-FGF-2 immune serum (1:200) at 21° C. for 40 minutes. GammaBind™ G Sepharose® (Pharmacia LKB Biotechnology, Uppsala, Sweden) was added for an additional 30 minutes incubation. Immune complexes are sedimented by microfuge centrifugation, washed three times with lysis buffer, and four times with ice cold immunoprecipitation wash buffer (0.15M NaCl, 0,01 M Na-phosphate pH 7.2, 1% deoxycholate, 1% NP-40, 0.1% sodium dodecyl sulfate). Immune complexes are dissociated directly in SDS gel sample buffer 125 mM Tres, pH 6.8, 4% SDS, 10% glycerol, 0.004% bromphenol blue, 2 mM EGTA, and separated by 12% SDS-PAGE. The gel is processed for fluorography, dried, and exposed to X-ray film at –70° C. When neomycin phosphotransferase is immunoprecipitated, a rabbit anti-NPT antibody (5Prime-3Prime, Boulder, Colo.) was used.

For western blot analysis, proteins are transferred from the 12% SDS-PAGE gel to a nitrocellulose membrane (pore size 0.45 µm in cold buffer containing 25 mM 3-[dimethyl (hydroxymethyl)methylamino]-2-hydroxypropane-sulfonic acid, pH 9.5, 20% methanol for 90 minutes at 0.4 amps. Membranes are blocked in 10 mM Tris, pH 7.5, 150 mM NaCl, 5 mM $NaN_3$, 0.35% polyoxyethylene-sorbitan monolaurate, and 5% nonfat dry milk (Carnation Co., Los Angeles, Calif.) for 1 hr at room temperature. Membranes are incubated with a monoclonal or polyclonal anti-FGF-2 antibody (Transduction Laboratories, Lexington, Ky.) at 0.3 µg/ml in blocking buffer at 4° C. for 16 hr. Following incubation, membranes are washed at room temperature with 10 changes of buffer containing 150 mM NaCl, 500 mM sodium phosphate pH 7.4, 5 mM $NaN_3$, and 0.05% polyoxyethylene-sorbitan monolaurate. Membranes are then incubated in blocking buffer containing 1 µg/ml rabbit anti-mouse IgG (H+L, affinipure, Jackson Immuno Research Laboratories, West Grove. Pa.) for 30 minutes at room temperature. Membranes are subsequently washed in 1 L of buffer described above. and incubated for 1 hr in 100 ml of blocking buffer containing 15 µCi $^{125}$I-protein A (ICN Biochemicals, Costa Mesa, Calif.), and washed with 1 L of buffer. The radiosignal is visualized by autoradiography.

Example 6

FGF-2 BIOASSAY

The bioactivity of FGF-2 may be measured in a thymidine incorporation assay. Cells transfected with FGF-2 as described above are incubated for 30 hr. At this time, the culture medium is replaced with 6 ml of DMEM containing 0.5% FBS (low serum medium) for 16 hr. The medium is removed, clarified by centrifugation in a microfuge for 15 minutes at 4° C. An equal volume of lysis buffer and heparin-Sepharose® CL-6B is added and the mixture incubated with rocking for 2 hr at 4° C. The Sepharose is pelleted and washed three times with lysis buffer followed by three washes with HS-wash buffer (20 mM Tris, pH 7.4, 5 mM EDTA, 2 mM EGTA, plus protease inhibitors, 0.5 M NaCl) and washed three times with HS-wash buffer containing 1 M NaCl. Proteins that remained bound to the Sepharose were eluted into HS wash buffer containing 3 M NaCl.

The stimulation of DNA synthesis was measured in quiescent Swiss 3T3 cells (clone NR-6) as previously described (Witte et al., J. Cell Physiol. 137:86–94, 1988; Florkiewicz and Sommer, Proc. Natl. Acad. Sci. USA 86:3978–3981, 1989). Briefly, cells were plated at low density and growth arrested by culturing for 72 hr in 1 ml of media containing 0.1% FBS. Various amounts of the 3 M NaCl HS-eluate are added directly to the culture medium and the level of [$^3$H]-tbymidine incorporation into TCA precipitable counts was measured 20–24 hr later. As a control, 1 pg to 1 ng of recombinant human FGF-2 was added to the cells in a similar manner.

Example 7

HIGH THROUGHPUT SCREENING ASSAY FOR MODLATORS

A high throughput screening assay is performed in a 48-well format. In this example, COS cells expressing FGF-2 are screened with modulators that inhibit export.

On the day of transfection, subconfluent to confluent COS cells are removed from a flask by the treatment with 0.25% trypsin for 5 to 10 minutes at 37° C. Detached cells are collected by centrifugation and washed once with PBS. COS cells are resuspended to 150,000 cells/ml in DMEM medium. Plasmid DNA (p18dxFGF) in a DEAE-dextran solution is added to the cells to a final concentration of 5 µg/ml. This amount is determined from optimization experiments using standard procedures. A solution containing FGF-2 DNA/DEAE-dextran is added, and the cells are incubated for 30 minutes at 37° C. The cells are then centrifuged and media containing 100 µM chloroquine is added. Chloroquine is subsequently removed, and the cells are plated at 20,000 cells per well in a 48-well tissue culture plate (Corning). The cells are incubated for 48 hours at which time the media is removed and a 100 mM sodium carbonate solution is added for approximately one minute. The sodium carbonate solution is removed, and the cells are washed with media containing 0.5% FGS and 25 µg/ml heparin. Media supplemented with Ouabain or other test compounds are added to the wells at the indicated concentrations and the cells are incubated for 20–24 hours.

Approximately 20 to 24 hours following the addition of ouabain or other test compounds, cell supernatant is assayed for the presence of FGF-2 using a standard ELISA based assay. Briefly, 96-well half area (Costar #369096) ELISA plates are coated with an anti-FGF2 monoclonal antibody at a concentration of 3 µg/ml for two hours at 37° C. Culture supernate samples are diluted in an equal volume of buffer containing protease inhibitors and added to the ELISA plate for an overnight incubation at 2–6° C. The wells are then washed, a biotinylated anti-FGF2 polyclonal antibody (R&D Systems) is added followed by Strepavidin-HRP and a chromogenic substrate. The amount of FGF2 is calculated by interpolation from an FGF2 standard curve.

As shown in FIGS. 29A–29C, ten different small molecules inhibit FGF-2 export from 55–74% at an approximately 10–15 µM concentration.

Example 8

DETECTION OF EXPORT AFTER TREATMENT WITH MODUJLATOR

COS cells are co-transfected as described above with plasmids expressing FGF-2, hCG-α, or neomycin phosphotransferase. Metabolic labeling is performed as described above, except that during the chase period, modulator that inhibits export is added at 10 nM to 1 mM in log increments. At the end of the chase, cells and cell media are harvested and processed for immune precipitations as described above.

Ouabain and digoxin inhibit the export of FGF-2, but not hCG-α. Ouabain inhibits 50% of leaderless protein export at approximately 0.1 µM and digoxin at approximately 5 µM. Further experiments with ouabain demonstrate that inhibition is time-dependent, does not affect secretion of hCG-α, and inhibits export of FGF-2 in a dose-dependent manner.

The ten small molecules that inhibit FGF-2 export are tested for altered leader sequence-mediated secretion of hCG-α. None dramatically reduce hCG-α secretion (FIGS. 29A–29C).

Example 9

ASSOCIATION OF LEADERLESS PROTEIN WITH A TRANSPORT MOLECULE

Co-transfecting COS cells with two plasmid expression vectors, one encoding 18 kDa FGF-2 and the other encoding the rat Na$^+$/K$^+$ ATPase α1 isoform, reveals whether the ATPase is a component of the transport apparatus. The plasmid (pCMV/ouabain) encoding the rat Na$^+$/K$^+$ ATPase α1 subunit may be purchased from PharMingen Inc. (cat #40002P). Forty eight hours post-transfection, cells are metabolically pulse-labeled with $^{35}$S-methionine (Met) plus cysteine (Cys) for 15 minutes washed with media containing excess (10 mM) unlabeled Cys and Met, then incubated for various lengths of time Cell and corresponding media fractions are immunoprecipitated with guinea pig polyclonal anti-FGF-2 immune serum. Immune complexes are dissociated directly in SDS-gel sample buffer and fractionated by 12% PAGE.

Figure 1B:
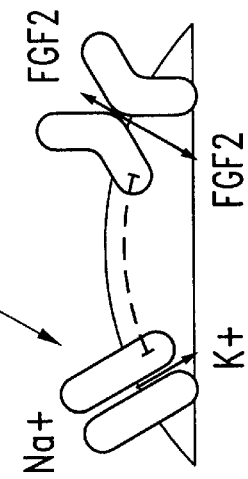
Figure 1D:
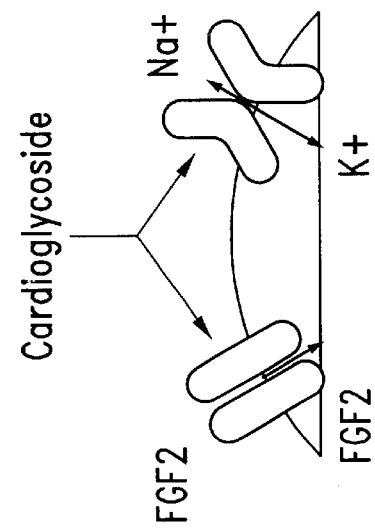
Figure 1A:
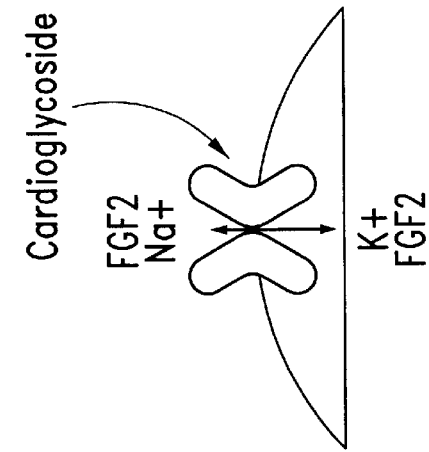
Figure 1C:
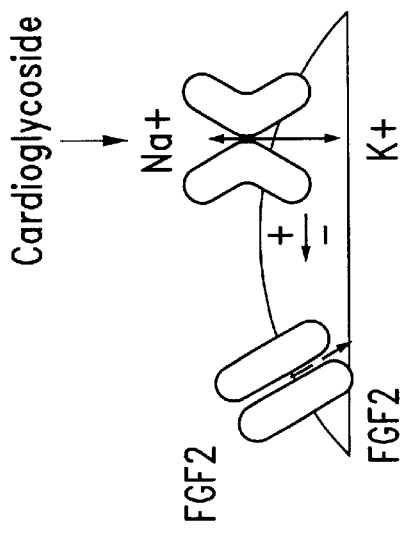
Figure 2A:
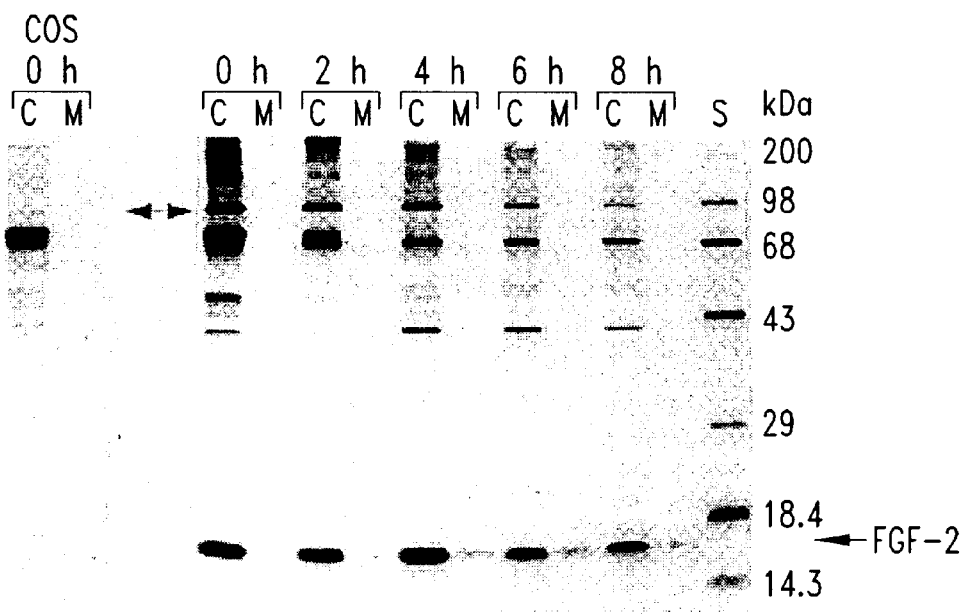
Figure 2B:
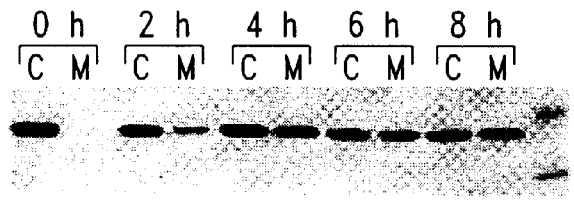

As shown, co-overexpression of rat Na$^+$/K$^+$ ATPase α1 along with 18 kDa FGF-2 interferes with FGF-2 export (FIG. 2). Compare FGF-2 (arrow) in panel A to panel B. Coexpression of the α1 subunit of rat Na$^{30}$/K$^+$ ATPase dramatically slows the rate of FGF-2 export (panel A) compared to control transfected cells (panel B). For reference, the rightmost lane (S) in panel A shows the location of $^{14}$C-labeled protein molecular weight standards, their molecular weights (kDa) are listed.

Figure 3A:
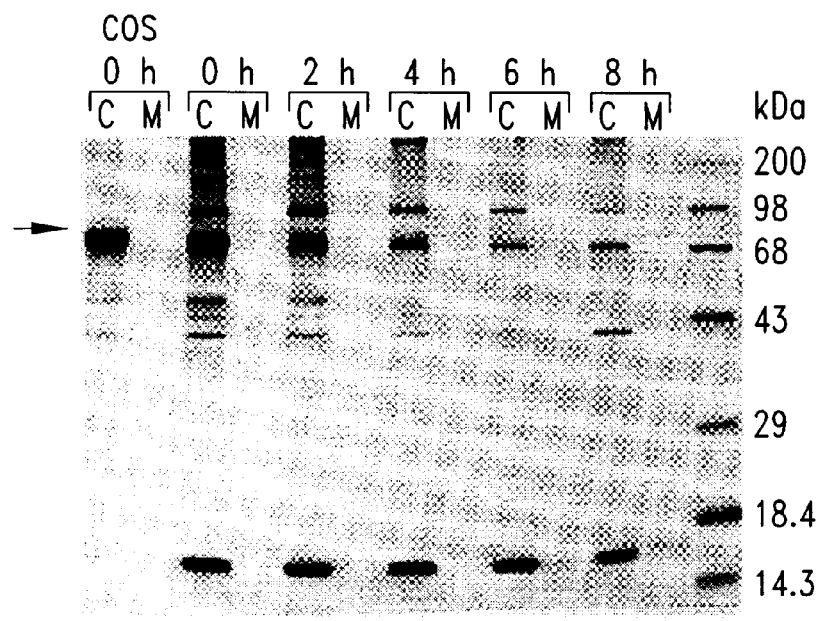
Figure 3B:
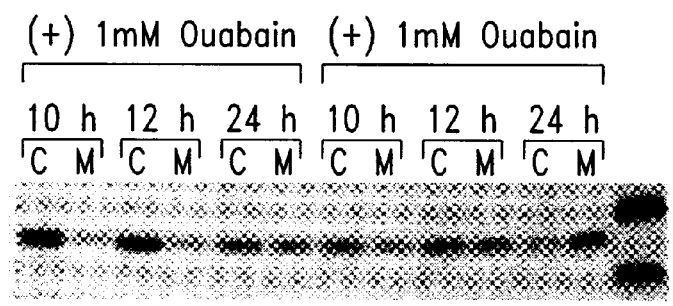

However, export of FGF-2 is not completely inhibited (FIG. 3). It requires greater than 12 hours for metabolically pulse labeled FGF-2 to become equally distributed between cell and media fractions (panel B). By twenty-four hours labeling export is essentially quantitative. Although 1 mM ouabain would completely inhibit export from FGF-2 only transfected COS cells, significant amounts of FGF-2 can be detected in media of Na$^+$/K$^+$ ATPase α1 co-transfected cells twenty-four hours post labeling. Since the rat Na$^{30}$/K$^+$ ATPase α1 isoform is 100 times more resistant to ouabain inhibition, these data further implicate Na$^+$/K$^+$ ATPase in export. These data also suggest that ouabain is not binding to a previously unidentified cell surface protein that functions as the FGF-2 exporter. If it were, then co-overexpression would have had no effect on FGF-2 export and/or the sensitivity to ouabain would have been the same.

Figure 4:
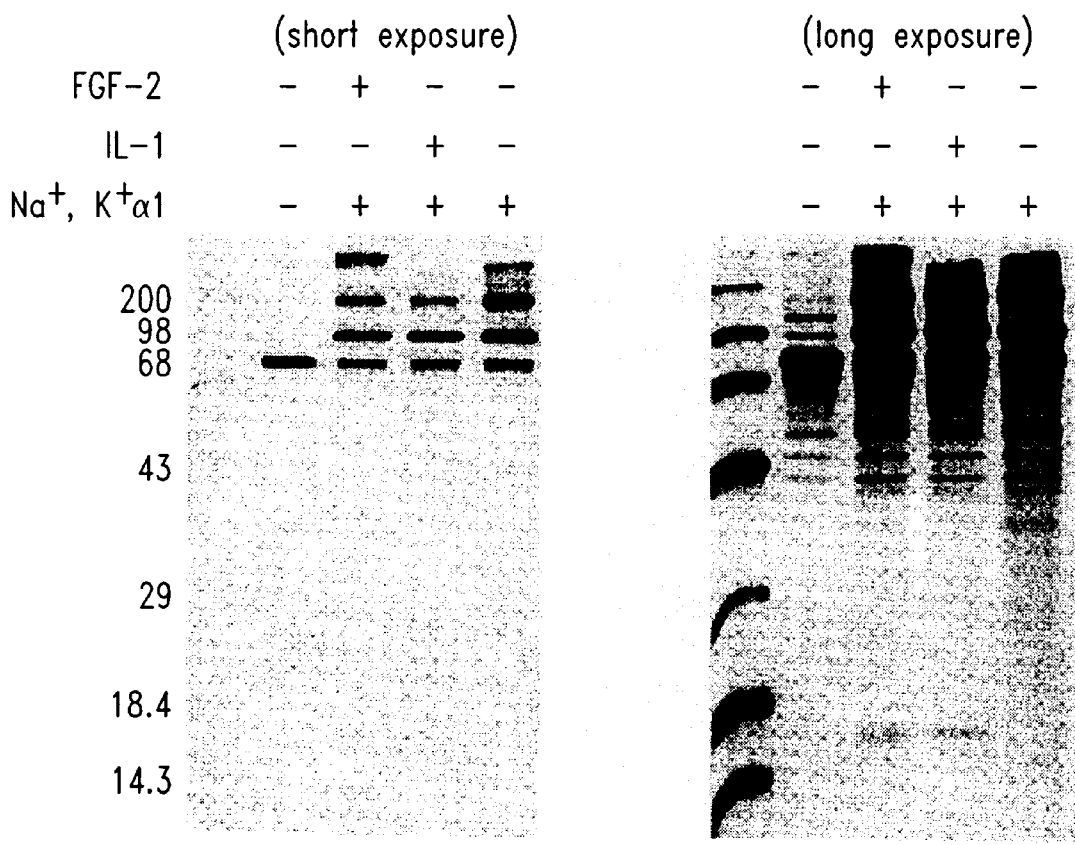
FIG. 4 is an autoradiogram of an immunoprecipitation with anti-Na$^+$/K$^+$ ATPase α1 antibody following transfection into COS cells. The table at the top indication the transfected genes.

The approximately 110 kDa protein band (FIG. 2, double arrow in panel A) is co-immunoprecipitated with FGF-2 using FGF-2 immune serum. This band is not detected in singly transfected or control non-transfected COS cells and is the correct size to be rat $Na^{30}/K^+$ ATPase $\alpha 1$. Immunoprecipitation of metabolically labeled COS cell extracts with monoclonal anti-rat $Na!/K^+$ ATPase $\alpha 1$ antibody, purchased from Upstate Biotechnology Inc. (cat #05–369), detects the same 110 kDa band plus an additional band, approximately 150 kDa (FIG. 4, panel A). When this gel is exposed to X-ray film for a longer period of time, an 18-kDa FGF-2 band can also be detected (FIG. 4, panel B). IL-1$\alpha$ can also be co-immunoprecipitated with rat $Na^+/K^+$ ATPase $\alpha 1$ from similarly co-transfected COS cells (FIG. 4, panel B). However, the 150 kDa band was not detected when immune complexes were prepared from co-expressing COS cells using anti-FGF immune serum. This suggests that the 150-kDa band is either a modified $Na^+/K^+$ ATPase $\alpha 1$ or represents a protein complex that includes $Na^+/K^+$ ATPase $\alpha 1$. Taken together, co-immunoprecipitation shows that FGF-2 directly interacts with $Na^+/K^+$ ATPase $\alpha 1$. This interaction is specific and not a consequence of our detergent lysis procedure, because complexes are not detected when singly transfected COS cell extracts are mixed, incubated for 4 hours and then immune precipitated.

Figure 5:
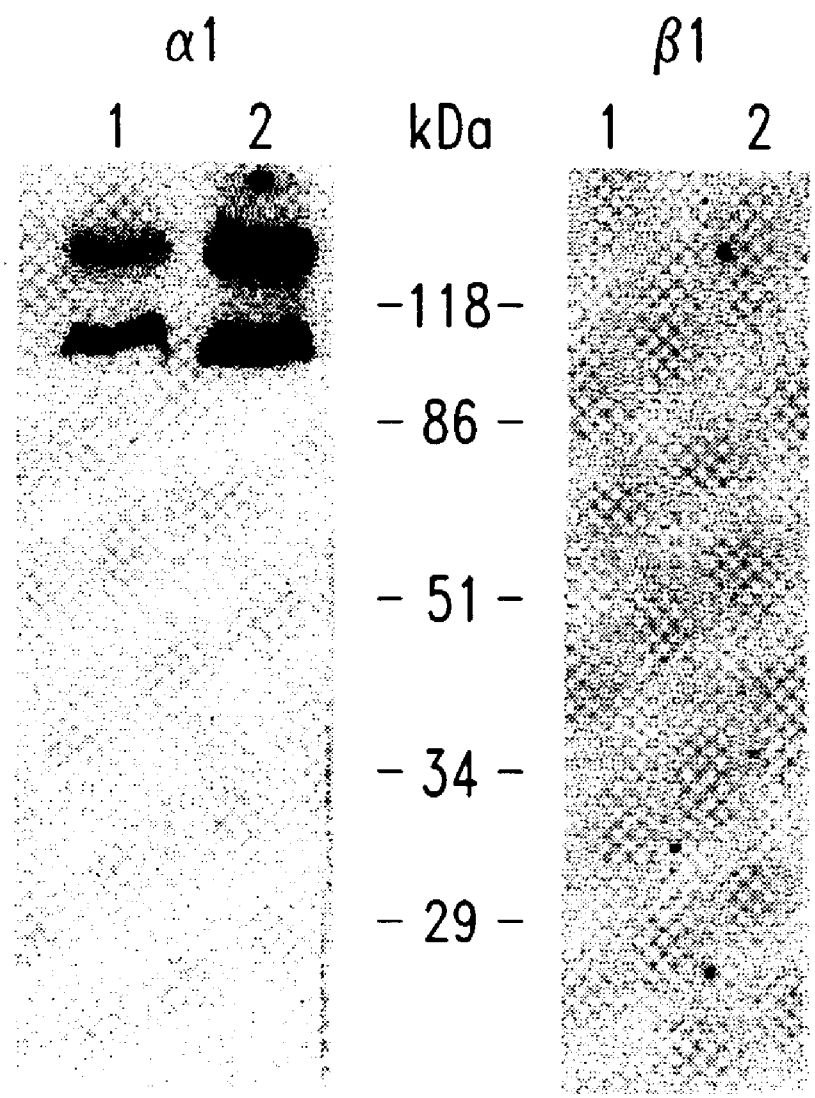
FIG. 5 is a Western blot of total COS cell extracts from nontransfected (lane 1) and pCMV/ouabain transfected (lane 2) cells. The antibody used for the left panel is an anti-Na$^+$/K$^+$ ATPase α1 antibody and for the right panel is an anti-Na$^+$/K$^+$ ATPase β1 antibody.
Figure 6:
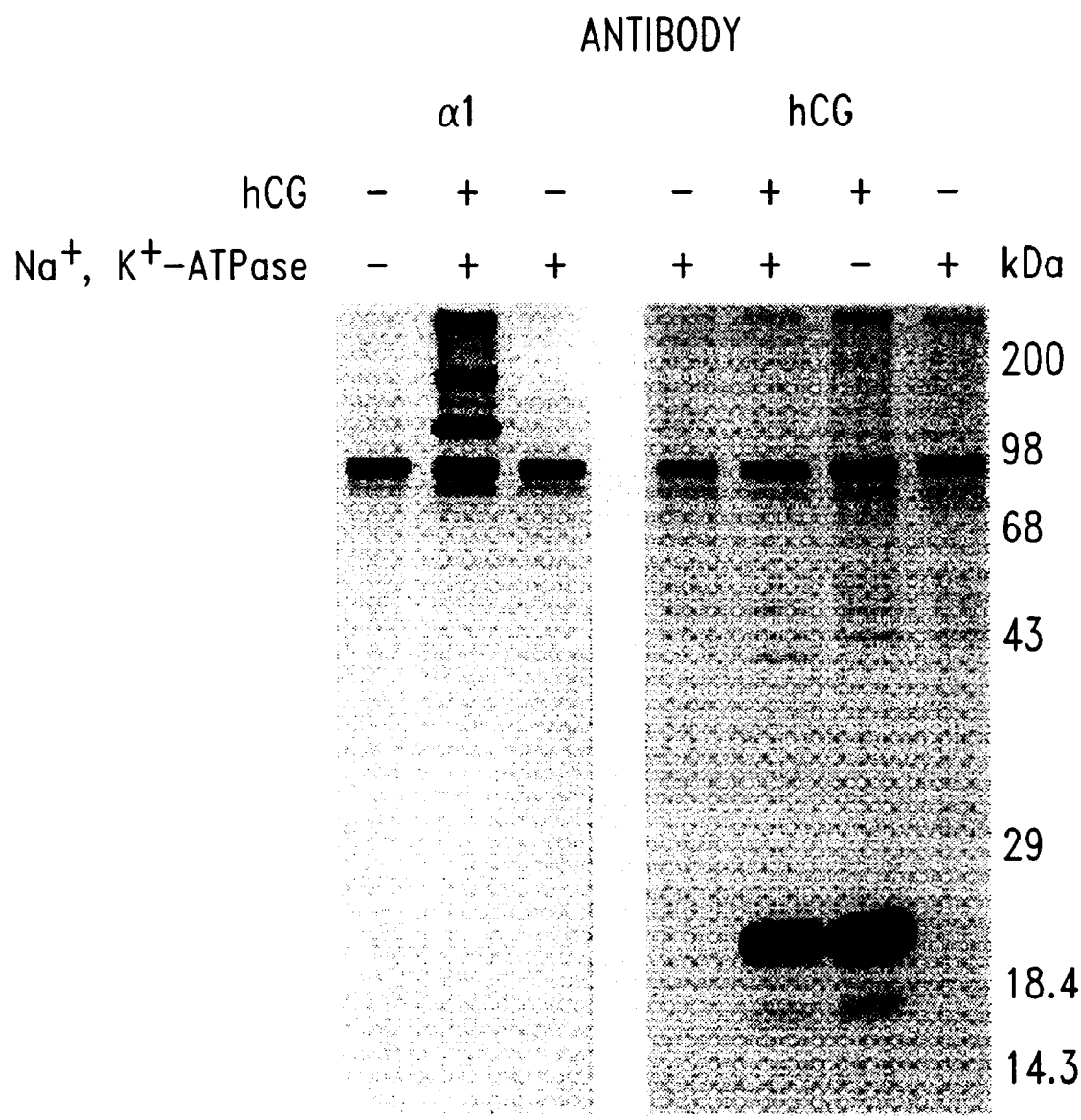
FIG. 6 is an autoradiogram of an immunoprecipitation with either anti-Na$^+$/K$^+$ ATPase α1 or anti-hCG antibody. The table at the top indicates the transfected genes.

Western blot analysis was used to confirm the identity of the 110 kDa band as rat $Na^+/K^+$ ATPase $\alpha 1$ (FIG. 5). Total cell extracts in 100 $\mu$l of standard detergent lysis buffer are prepared from 60 mm plates of non-transfected (lane 1) as well as pCMV ouabain transfected COS cells (lane 2). Mixed with 60 $\mu$l of this extract is 20 $\mu$l of 4× concentrated SDS-gel sample buffer, which is heated at 65° C. for 20 minutes. Samples are fractionated by 12% PAGE and transferred to nitrocellulose membrane supports. The probe was the same monoclonal anti-rat $Na^+/K^+$ ATPase $\alpha 1$ antibody used for the immunoprecipitation experiments described above. However, in this case, steady state levels of endogenous gene expression are detected as well as expression from the transfected gene, both non-transfected and pCMV ouabain transfected COS cells contain an approximately 110 kDa immunoreactive band. A significant increase in this band is detected in pCMV ouabain transfected COS cells, i.e., from those cells expressing rat $Na^+/K^+$ ATPase $\alpha 1$.

Co-immunoprecipitation of rat $Na^+/K^+$ ATPase $\alpha 1$ from co-transfected COS cells is specific for FGF-2. Results from a series of control experiments using overexpressing transiently transfected COS cells are shown in FIGS. 6–10. For example, using a plasmid expression vector encoding hCG-$\alpha$, leader sequence-dependent secretion of hCG-$\alpha$ is clearly distinguished from export of the leaderless protein FGF-2. Moreover, hCG-$\alpha$ does not co-immunoprecipitate with $Na^+/K^+$ ATPase $\alpha 1$ (FIG. 6) even though $Na^{30}/K^+$ ATPase $\alpha 1$ subunit and hCG-$\alpha$ both possess a signal sequence, which would place the two proteins in close proximity during transport through the ER/Golgi apparatus.

A number of cytosolic proteins other than FGF-2 have been overexpressed in transiently transfected COS cells and remain cell associated in metabolic labeling pulse chase experiments. 'Jhese include neomycin phosphotransferase (NPT) and $\beta$-galactosidase ($\beta$-gal). However, the exported phenotype can be conferred to both proteins when expressed as chimeras with 18 kDa FGF-2. The FGF-2 NPT chimeric (i.e., fusion) protein is termed FPT, and the FGF-2 $\beta$-gal chimeric protein F-gal. Export of both FPT and F-gal chimeric proteins can be inhibited by ouabain, in a manner paralleling that for FGF-2. Therefore, the FPT chimeric protein was tested in more detail for its ability to be co-immunoprecipitated with $Na^{30}/K^+$ ATPase $\alpha 1$ from co-transfected COS cells (FIGS. 7–9). The data indicate that FPT interacts with $Na^{30}/K^+$ ATPase $\alpha 1$ and is co-immunoprecipitated. In contrast. authentic NPT does not co-immunoprecipitate with $Na^{30}/K^+$ ATPase $\alpha 1$ regardless of which antibody or immune serum was employed. The same results are achieved with the F-gal chimeric protein. In FIGS. 10 and 11, COS cells are co-transfected with plasmids encoding the $Na^+/K^+$ ATPase $\alpha 1$ subunit and FGF-2, or with plasmid encoding a FGF-2 plus VSVG chimeric protein.

In addition to interaction of $\alpha 1$ subunit with FGF-2, both $\alpha 2$ and $\alpha 3$ isoforms also bind to FGF-2. The isoforms $\alpha 2$ and $\alpha 3$ are co-expressed at 4:1 ratio with FGF-2 in transfected COS cells as described above. As seen in FIGS. 13–16, $\alpha 2$ and $\alpha 3$ interfere with the export of FGF-2. As well, a protein of approximately 110 kDA is also detected; this is the size expected for the $\alpha 2$ and $\alpha 3$ subunits. Immune complexes prepared from metabolically labeled co-transfected COS cells using anti-$\alpha 2$ or anti-$\alpha 3$ antibody show a protein band the size of FGF-2 (FIG. 16).

Example 10

OUABAIN SENSITIVITY OF LEADERLESS PROTEIN EXPORT

A vector containing a leaderless protein gene. IL-1$\alpha$, is transfected into COS cells. Cells are metabolically labeled and protein precipitated with anti-IL-1$\alpha$ antibody. As seen in FIGS. 12, 17, 19 and 21, IL-1$\alpha$ is exported into the cell supernatant (i.e., media) fraction (M). This export is inhibted by incubation with 5 mM ouabain (FIGS. 18, 20 and 21). In contrast to the export of FGF-2, the rate of IL-1 export is slower, having a $T_{1/2}$ of greater than 24 hrs. However, like FGF-2, the export is sensitive to ouabain. In addition, IL-1$\alpha$ can be immunoprecipitated from co-transfected COS cells (transfected with IL-1$\alpha$ and the Na/K ATPase $\alpha 1$ subunit) using anti-$\alpha 1$ subunit antibody (FIG. 4).

Example 11

RUBIDIUM UPTAKE ASSAY TO MEASURE ION TRANSPORT ABILITY OF $NA^+/K^+$ ATPASE

The ion transport activity of $Na^+/K^+$ ATPase may be measured by a rubidium uptake assay in the presence and absence of a modulator.

In this assay, cells that express the $Na^+/K^+$ ATPase are grown in the presence of a modulator that inhibits $Na^{30}/K^+$ ATPase activity. The mutated rat $\alpha 2$ isoform, referred to as rat $\alpha 2^*$, is modified by the substitutions L111R and N122D at the borders of the first intracellular domain. This makes rat $\alpha 2^*$ resistant to ouabain ($IC_{50}$ approximately 50 $\mu$M). Site-directed mutagenesis is used to make further mutations at position 327.

Wild type COS cells, HeLa cells, and Hela cells transfected with the rat $\alpha 2^*$ mutants are maintained in DMEM with 10% calf serum, 100 units/ml penicillin, 0.1 mg/ml streptomycin, and 250 ng/ml amphotericin B at 37° C. in a 5% $CO_2$ atmosphere. $^{86}$Rb is obtained from DuPont-New England Nuclear. The specific radioactivity varies from approximately 2–10 mCi/mg. Otiabain and furosemide are obtained from Calbiochem or Sigma.

Native HeLa, or cells transfected with rat α2*, are plated at 3×10⁴ cells per ml in 24-well tissue culture plates (1 ml per well). The rat α2* transfected cells are grown in the absence or presence of 1 µM inhibitor to examine ouabain dose response in cells that display both endogenous and transfected ion transport activities or with cells that display the transfected activity alone. Cells are incubated until about 80% confluent. then rinsed with PBS (135 mM NaCl, 3.5 mM KCl, 0.5 mM CaCl$_2$, 0.5 mM MgCl$_2$, 5 mM glucose, 6.5 mM Na$_2$HPO$_4$, 1.5 mM KH$_2$PO$_4$,) and further incubated with PBS containing the indicated inhibitor concentrations for 30 min at 37° C. $^{86}$Rb is then added at approximately 2 µCi per ml for 10 min at 37° C. The concentration of $^{86}$Rb typically ranges from 2–15 µM. The incubation is stopped by submerging the plate in an ice cold solution of 0.9% NaCl and 5 mM HEPES, pH 7.4. Wells are then rinsed 8 times in this solution. Total rinse time is less than 1 minute. Cells are extracted with 0.5 ml 0.2 N NaOH for 1 hour, then neutralized with HCl before counting. Samples are counted in a Packard Tricarb Liquid Scintillation Analyzer, Model 2000CA, which has an efficiency for $^{86}$Rb of 97%.

Example 12

CONSTRUCTION OF A LEADERLESS PROTEIN FUSION AND IDENTIFICATION OF INTERACTING PROTEINS

In this example, a fusion of glutathione S-transferase (GST) with the leaderless protein, FGF-2, is constructed. The resulting fusion protein is then used in affinity column chromatography to identify proteins or protein complexes that interact with FGF-2.

An expression vector encoding the 18 kDa isoform of FGF-2 (pGEXF18) is prepared. The plasmid pGEXF18 is constructed by amplifying a sequence encoding the 18 kDa FGF-2 and inserting the amplified fragment into the NotI site of pGEX-4T-3 (Pharmacia, Uppsala, Sweden). The template for amplification is p18dx (see Example 1), which encodes only the 18 kDa isoform of FGF-2. The forward amplification primer (SEQ ID NO: 20) is

5'-AAGGACAGAAGCGGCCGCGGGACCATGGC AG-3', and the reverse amplification primer (SEQ ID NO: 21) is

5'-AAGGACAGAAGCGGCCGCTCAGCTCTTAGCA GCCATTGG-3'.

The amplification conditions are 2 cycles of 94° C. for 5 min. 45° C. for 5 min, 72° C. for min; 4 cycles of 94° C. for 1 min, 450 for 1 min, 72° C. for 1 min; 25 cycles of 94° C. for 1 min, 55° C. for 1 min, 72° C. for 1 min; and 1 cycle of 72° C. for 10 min.

Bacteria (for example, DH5α or BL21) containing the GST-FGF-2 expression plasmid are induced with IPTG (0.2 mM) for 3 hours. Cell extracts are prepared and the GST-FGF-2 fusion protein purified using glutathione-Sepharose as described by the manufacturer. Purified fusion protein is eluted from glutathione beads by 10 mM glutathione.

COS cells (100 mm plates 80% confluent) are metabolically labeled for 4 hours in cysteine/methionine-free DMEM supplemented with 100 µCi/ml of $^{35}$S-trans label (ICN, Irvine, Calif.). After labeling, cell monolayers are washed with buffer containing 25 mM Tris, pH 8.0, 150 mM NaCl. Cells are lysed with 2.0 ml NETN buffer (20 mM Tris pH 8.0, 100 mM NaCl, 1 mM EDTA, 0.5% NP40) as described (Kaelin et al., Cell 64:521–532, 1991). This cell extract is clarified of insoluble material by microcentrifugation at 4° C. for 15 minutes. Other cell types can be substituted for COS cells and other wild type or mutant GST fusion proteins may be used.

Glutathione-Sepharose beads (100 µl) are charged with purified GST-FGF-2 fusion protein (25 µg) in buffer containing NETIN plus 0.5% powdered milk while rocking for 30 minutes at 4° C. The metabolically labeled COS cell extract (0.5 ml) is incubated with 25 µl of the charged beads for 1 hour at 4° C. Alternatively, cell membrane fractions from metabolically labeled cells may be used. Sepharose beads with bound proteins are then pelleted by centrifugation and washed 4 times with cold NETN buffer. Protein complexes are dissociated directly in SDS-sample buffer and incubated at 70° C. for 20 minutes. The proteins are fractionated on 12%-PAGE (FIG. 22). Non-specific background is detected in lanes corresponding to metabolically labeled COS cell protein bands binding control GST alone (GST 4T) and a control unrelated GST fusion protein (GST-R2). At least 4 distinct COS cell proteins appear to bind specifically to GST FGF-2. Proteins identified may represent those transport molecules that directly interact with FGF-2 to fonn a protein complex, or transport molecules in the form of a cell transport apparatus that interacts as a protein complex with FGF-2. COS cell proteins that detectably interact with the GST-FGF-2 fusion are approximately 35, 45/50 and 70 kDa. The pattern of protein bands detected by SDS-PAGE is reproducible in all cases. Additional very large proteins or protein complexes are not identified at this time.

Example 13

IDENTIFICATION OF CANDIDATE TRANSPORT MOLECULES

In this example, several specific proteins are identified that interact with exported forms of the leaderless proteins, FGF-2 and IL-1β. Essentially, the procedures followed in Example 12, above are utilized.

The expression vector pGEXF18 was prepared as indicated above. In addition, an expression vector encoding the 55 amino acid N-terminal extension of the non-exported 24 kDa isoform of FGF-2, designated pGEX43 (expression product designated GST55F24), is prepared. Plasmid pGEX43 is constructed by amplifying a sequence encoding the 55 amino acid N-terminal extension of the non-exported 24 kDa isoform of FGF-2 and inserting the amplified fragment into the IotI site of pGEX-4T-3 (Pharmacia, Uppsala, Sweden). The template for amplification is described in Florkiewicz and Sornrner, Proc. Nail. Acad. Sci. USA 86–3978, 1989.

DH5α containing either the pGEXF18 or pGEX43 expression plasmid are used to inoculate 5 ml of LB containing 50 µg/ml ampicillin in 50 ml tubes and shaken overnight at 37° C. The cultures are then used to inoculate 500 ml of LB media containing 50 µg/ml of Ampicillin. The cultures are grown to log phase and induced with 1 mM IPTG and grown for an additional 4–5 hours at 30° C. Following growth the cultures are centrifuge for 20 minutes, 4° C., and 4000 rpm in a JA-10 rotor. J2-HS Beckman centrifuge. Cell pellets are resuspended in 25 ml total voume LB and centrifuged at 4° C. for 10 minutes at 4000 rpm, the cell supernatant is then aspirated, and cell pellets are either used immediately or stored at –80° C.

The cell pellets are lysed by adding 12.5 ml of 50 mM Tris, 5 mM EDTA, 50 mM NaCl, pH 7.0 with 0.1 mM PMSF, 1 mM DTT, and ½ of a protease inhibitor cocktail tablet (Complete™, Boehringer Manheim #1697498). The GST fusion proteins are then purified using glutathione-Sepharose as described by the manufacturer. Purified fusion protein is eluted from glutathione beads by 10 mM glutathione.

COS cells (150 mm plates 80% confluent) are washed two times in cysteine, methionine free DMEM (3 ml per wash).

5 ml of cys/met free DMEM is added and the cells are incubated for 20 minutes at 37° C. and washed again with the same medium. Following washing, 5 ml of cys/met free DMEM containing 500 pCi of $^{35}$S-TransMet (ICN) is added to the cells and the cells are allowed to incubate for 4 hours at 37° C. with occasional rocking. The cells are then washed twice with 5 ml of PBS and the cells are lysed for 30 minutes at 4° C. by the addition of 1 ml NETN buffer (50 mM Tris pH 8, 5 mM EDTA, 120 mM NaCl, 1.0% NP-40, protease inhibitor cocktail) per plate. Insoluble material is pelleted for 15 minutes at 14,000 rpm, 4° C., in amicrocentrifuge. The cell supernatant is then used for affinity experiments.

Affinity experiments are carried out essentially as discussed in Example 12. Briefly, the ethanol preservative is removed from glutathione Sepharose 4B Pharmacia cat#17–0756–01) by washing 3 times with 1 ml NETN buffer (50 mM Tris pH 8, 5 mM EDTA, 120 mM NaCl, 1.0% NP-40, protease inhibitor cocktail). Following washing, approx 4 μg of GST18 or GST43 is bound to 20 μl glutathione Sepharose for 20 minutes on ice then washed 3 times with 1 ml NETN buffer. The washed GST fusion protein/glutathione-Sepharose complex is then added to the labeled cell supernatant and bound for 60 minutes at 4° C. with rocking. Beads are then collected by microcentrifugation then washed 6 times in 1 ml EBC buffer (20 mM Tris pH 8, 0.2 mM EDTA, 150 mM KCl, 0.5% NP-40, 0.05% SDS, 20% glycerol, 5 mM DTT) and 2 times with PBS before solublization in 50 μl of SDS-PAGE sample buffer. The sample is then run on SDS-PAGE and stained.

As demonstrated in FIG. 30, SDS-PAGE analysis yields several bands, which are apparent in the GSTF18 lanes. but absent or decreased in the GST55F24 lanes. The experiment is also performed using GSTF18 and cell types HEC-1B and U87 in addition to COS-1 cells. As demonstrated in FIG. 31, the results using different cell lines are qualitatively similar, but quantitatively different, thus indicating the possiblity of up or down regulation of certain transport molecules in different cell types.

GST fusion constructs of mature and precursor interleukin-1β are also created and utilized to screen for interactive proteins derived from metabolically labeled ($^{35}$S-Methionine) THP-1 cells. In the various experiments, metabolically labeled proteins derived from THP-1 cell extracts or conditioned media were tested for their ability to bind fusion constructs of GST and mature interleukin-1β (GST-mIL1β) and precursor interleukin-1β (GST-pIL1β) in the presence and absence of lipopolysacharride (LPS) and nigericin-(nig). See FIGS. 32–34. As is depicted in FIG. 32, their appears to be different proteins that interact with mature and precursor forms. Accordingly, in FIGS. 33 and 34, precursor IL-1β interactions are further probed by examining non-LPS treated cell extracts (FIG. 33) and media from cells not stimulated for IL production with LPS. The conditioned media experiments are performed by metabolic labeling with $^{35}$S-Methionine for four hours, followed by collection and clarification of media (e.g., by centrifugation) and analysis of binding as detailed in Example 12, above.

While a number of potential candidate molecules bind to preIL-1β within the cell (FIG. 33), several interesting candidates are also present in the conditioned media. One such candidate (p50) is characterized by microsequencing using mass spec/mass spec (using a commercial facility such as Harvard Univ. Microchemistry Facility) as tubulin and preferentially associates with preIL-1β. The other bands may be sequenced by the same methodology.

For the above interleukin 1β experiments, a plasmid containing the complete mRNA sequence encoding human IL-1 β (GenBank Accession No. M15330) was used as template for PCR-based subcloning and preparation of bacterial expression vectors synthesizing glutathione S-transferase (GST)-IL-1β chimeric proteins. Under normal cell conditions only precursor IL-1β is expressed as a primary translation product, the mature form of IL-1β results only from the proteolytic processing of precursor while it resides in the cytosol. Therefore the same cDNA template is used for PCR amplification of precursor and mature IL-1β. For mature IL-1β, PCR primers were designed to begin at the first amino terminal amino acid of mature IL-1β that would exist after processing of the precuisor form.

The PCR amplification product for precursor IL-1β was TA cloned into pCR3.1 (Invitrogen) and the nucleotide sequence confirmed. The insert-encoding precursor IL-1β was then excised with BamHI plus SmaI and directionally subcloned into BamHI/SmaI digested pGEX-4T-3 (Pharmacia, Uppsala. Sweden), allowing bacterial expression and subsequent purification of GST-preIL-1β. The forward amplification primer for precursor IL-1β was (SEQ ID NO:37):

5' GCGTGGATCCGCAGAAGTACCTGAGCTCGCC 3'
and the sequence of the reverse amplification primer was (SEQ ID NO:37):
5'ATGTCCCGGGTTAGGAAGACACAAATTGC-ATGG 3'

The amplification conditions for PCR of precursor IL-1β are 1 cycle of 95° for 5 min; 12 cycles 95° for 1 min. 55° for 1 min, 73° for 2 min; 20 cycles of 95° for 1 min, 63° for 1 min, 72° for 2 min; 1 cycle 72° for 5 min.

The forward amplification primer for mature IL-1β was (SEQ ID NO:39):
5'GCGTGGATCCGATGCACCTGTACGATCACTG 3'
and the sequence of the reverse amplification primer was (SEQ ID NO: ):
5'ATGTCCCGGGTTAGGAAGAC-ACAAATTGCATGG 3'

The PCR product for mature IL-1β was TA cloned into pCR3.1 (Invitrogen), then excised with BamHI plus SmaI and directionally ligated into the polylinker site of pGEX-4T-3 (Pharmacia). Clones were correct based on sequencing from both directions. The amplification conditions Lor PCR of mature IL-1β are 1 cycle of 95° for 5 min; 12 cycles 95° for 1 min, 550 for I min, 730 for min; 20 cycles of 95° for 1 ml, 63° for 1 min, 72° for 2 min; 1 cycle 72° for 5 min. extracts are then prepared and the GST-IL-1 fusion protein purified using glutathione-Sepharose as described by the manufacturer. Purified fusion protein is eluted from glutathione beads by 10 mM glutathione.

Human THP1 cells (ATCC No. TIB 202) are metabolically labeled for 3 hours in cysteine/methionine free RPMI supplemented with 100 μCi/ml of $^{35}$S-trans label (ICN, Irvine, Calif.). Interacting proteins are detected from metabolically labeled human THP1 cell extracts after lysis with buffer containing 20 mM Tris pH 8.0, 100 mM NaCl, 1 mM EDTA and 0.5% NP40, as described (Kaelin et al., Cell 64:521–532, 1991). This cell extract is clarified of insoluble material by microcentrifugation at 4° C. for 15 minutes. Cell extract is then incubated with glutathione Sepharose 4B (Pharmacia #17–0756–01) charged with the appropriate GST-fusion protein.

For LPS stimulation 2.5 μg/ml for 4 hours. For nigericin treatment 20 μM final concentration was utilized to treat cells for 20 to 30 minutes prior to pull down experiments.

Example 14

COMPETITION ASSAYS TO DETECT THE STABILTY OF LEADERLESS PROTEIN/TRANSPORT MOLECULE COMPLEXES

In this example, labeling and preparation of COS extracts and affinity purification is performed as indicated above.

After binding the GST-FGF-2 fusion protein to glutathione Sepharose (i.e. "charging" of the glutathione Sepharose), the cell extracts were added to the charged Sepharose. However, to compete for binding to the GST-FGF-2 fusion protein, various amounts of recombinant FGF-2 or other components are added with the cell extract. Accordingly, during binding competition, the cell extract is added with a) no recombinant FGF-2; b) 4 μg of recombinant FGF-2; c) 12 μg recombinant FGF-2; d) 24 μg recombinant FGF-2; e) 25 μg/ml Heparin; and f) 1 μg /ml low molecular weight Heparin octasaccharide.

As illustrated in FIG. 35, FGF-2. competes with GST18 for binding to p47 and p80, but apparently does not reduce binding to p35, p150–200, or p400. Heparin allows numerous additional bands to complex with the GST-FGF-2 fusion protein. In contrast, heparin and the heparin octasaccharide reduce or completely inhibit the binding of p35, p48, p80, p150–200, and p400 to the GST-FGF-2 fusion protein. Proteins p48 and p80 bind to FGF-2 with approximately the same affinity, while p35 appears to bind the fusion either with higher affinity or a higher order stoichiometry.

Example 15

CONSTRUCTION OF AN FGF-1 FUSION PROTEIN

Several fusion proteins are constructed in which FGF-1, either full-length or a fragment, is fused at the N-terminus to GST or at the C-terminus to a peptide tag.

The FGF-1 designer gene clone, BBG21 (R&D Systems, Minneapolis, Minn.), does not encode a full-length wild type protein. It lacks 14 amino acids at the N-terminus of the wild type primary translation product. A full length wild type FGF-1 is prepared from the plasmid BBG21 (R&D Systems). Based on that sequence the forward amplification primer (SEQ ID NO: 22) is 5'-CTAGGGATCCACCATGGCCGAGGGCGAAATT ACAACATTCACCGCCCTCACCGAAAAGTTTA ATCTCCCTCCCG-3' and the reverse amplification primer for wild type FGF-1 (SEQ ID NO: 23) is

5'-GATCGAATTCTCAATCAGAAGAAGCTGGCAG-3'.

The forward primer recreates the following N-terminal amino acids: AEGEITTFTALTEK (SEQ ID NO: 24). This primer set is designed for insertion into the BamHI/EcoRI sites of pcDNAIII (Invitrogen, La Jolla, Calif.). This vector allows expression in mammalian cells, including transient over-expression in COS cells. The amplified product is designed to have a preferred sequence context for translation initiation. In addition the same amplified product and restriction sites allow an inframe N-terminal fusion with GST (pGEX-4T-3). Amplification conditions consist of 1 cycle 1 of 94° C. for 1 min; 8 cycles of 94° C. for 45 sec, 48° C. for 45 sec, and 72° for 1 min 25 cycles of 94° C. for 45 sec, 65° C. for 45 sec, and 72° C. for 1 min; and 1 cycle of 72° C. for 5 min.

In order to have additional antibodies to choose from for immunoprecipitation of a full-length and/or N-terminal truncated FGF-1, FGF-1 is also fused to C-terminal sequences that encode peptide tags recognized by antibodies that are commercially available. The C-terminal epitope tags include the fig peptide DYKDDDDK (SEQ ID NO: 35) and influenza haemagglutinin (HA) peptide YPYDVPDYA (SEQ ID NO: 36). The reverse amplification primer sequence adding the HA epitope tag to FGF-1 (SEQ ID NO: 25) is:

5'-CTAGTCTAGATCAGGCGTAGTCGGGCACGTC GTATGGGTAATCAGAAGAGACTGGCAGG-3'.

The reverse primer adding the flg epitope tag to FGF-1 (SEQ ID NO: 26) is

5'-GATCGAATTCTCACTTGTCATCGTCGCCTTGT AGTCACGCGTATCAGAAGAGACTGGCAG-3'.

In both cases, the forward primer is as described above. Amplification conditions are 1 cycle of 94° C. for 1 min; 8 cycles of 94° C. for 45 sec, 48° C. for 45 sec, for 45 sec, 72° C. for 1 min 25 cycles of 94° C. for 45 sec, 65° C. for 45 sec, and 72° C. for 1 min; and 1 cycle of 72° C. for 5 min.

Example 16

CONSTRUCTION OF HIV TAT FLSION PROTFINS

Both an 85 amino acid and a 72 amino acid tat gene product is constructed as a fusion with C-terminal epitope tag sequences. The template for Tat85 is BBG34 (R&D Systems; Minneapolis, Minn.) and for Tat72 is pSV2tat72. For subcloning HIV Tat 72 or TAt 85, the forward amplification primer (SEQ ID NO: 27) is

5'-CTAGGGATCCACCATGGAACCAGTCGACC-3'

The reverse primer for wild type Tat 85 (SEQ ID NO: 28) is

5'-GATCGAATTCTCATTCCTTAGGACCTGTCGG-3' and the reverse primer encoding the C-terminal HA-tag epitope (SEQ ID NO: 29) is

5'-CTAGTCTAGATCAGGCGTAGTCGGGCACGTC GTATGGGTATTCCTTAGGACCTGTCGG-3'.

The reverse primer for Tat 72 (SEQ ID NO: 30) is

5'-CTAGGAATTCAGATCACTGTTTAGACAGAG-3' and the reverse primer encoding the C-terminal flg tag (SEQ ID NO: 31) is

5'-CTGAGAATTCTCACTTGTCATCGTCGTCCTTG TAGTCCTGTTTAGACAGAGAAACC-3'.

The reverse primer for Tat72 plus C-terminal HA-tag (SEQ ID NO: 32) is

5'-CTGAGAATTCCAGGCGTAGTCGGGCACGTCG TATGGGTACTGTTTrAGACAGAGAAACCTG-3'.

Reaction conditions for amplification of wild type Tat 85 and Tat85HA-tag are: 1 cycle of 94° C. for 1 min; 8 cycles of 94° C. for 45 sec, 52° C. for 45 sec, and 72° C. for 1 min; 25 cycles of 94° C. for 45 sec, 65° C. for 45 sec, and 72° C. for 1 min; and 1 cycle of 72° C. for 5 min. Reaction conditions for amplification of Tat72 using the above primers are: 1 cycle of 94° C. for 1 min; 8 cycles of 94° C. for 45 sec, 52° C. for 45 sec, and 72° C. for 1 min; 25 cycles of 94° C. for 45 sec. 65° C. for 45 sec, and 72° C. for 1 min; and 1 cycle of 72° C. for 5 min. Amplification conditions for Tat72 plus flg-tag are: 1 cycle of 94° C. for 1 min: 8 cycles of 94° C. for 45 sec, 50° C. for 45 sec, and 72° C. for 1 min; 28 cycles of 94° C. for 45 sec. 65° C. for 45 sec, and 72° C. for 1 min; and 1 cycle of 72° C. for 5 min. Amplification conditions for Tat72 HA-tag are: 1 cycle of 94° C. for 1 min; 8 cycles of 94° C. for 45 sec, 55° C. for 45 sec, and 72° C. for 1 min; 28 cycle of 94° C. for 45 sec, 70° C. for 45 sec, and 72° C. for 1 min; and 1 cycle of 72° C. for 5 min.

Example 17

CONSTRUCTION OF IL-1α FUSION PROTEINS

A vector encoding mature human IL-1α is used to transfect COS cells. As described above, subclone in pGEX4T-3 is prepared to detect cell associated protein(s) that bind with mature IL-1α. The forward PCR primer (SEQ ID NO: 33) is

5'-CTAGGGATCCACCAT-GAGGATCATCAAATACGAATTC-3' and the reverse PCR primer (SEQ ID NO: 34) is

5'-GCACTTCTCGAGCTACGCCTGGTTTTCCAGTA TC3'.

The PCR amplification conditions are: 1 cycle of 94° C. for 1 min; 8 cycles of 94° C. for 45 sec, 60° C. for 45 sec, and 72° C. for 1 min; 25 cycles of 94° C. for 45 sec. 70° C. for 45 sec, and 72° C. for 1 min; and 1 cycle of 72° C. for 5 min.

Both IL-1α: and FGF-2 are exported from transfected COS cells in a ouabain-sensitive manner. Therefore, the profile of binding proteins for each leaderless protein that is present in COS cells is compared to determine if there are common and/or distinct binding proteins. In addition, IL-1α will be expressed in the rodent macrophage cell line P388D$_1$. A similar strategy can be used for IL-1α.

Example 18

CONSTRUCTION OF VSV N GENE PRODUCT FUSION PROTEINS

A GST-VSV N gene product fusion is prepared in pGEX4T-3 vector. The data presented in FIGS. 23–28 show that VSV N protein expressed in transiently transfected COS cells can be detected in conditioned media. The N protein does not contain a hydrophobic signal peptide sequence and is therefore predicted to reside in the cytosol. Polyclonal rabbit anti-VSV antibody is used to precipitate the N protein from metabolically labeled cells. As shown herein, the N protein is detected extracellularly in a time dependent manner (FIG. 23). Also, N protein export is ouabain-resistant (FIGS. 24, 27), ATP-dependent (FIG. 25), and ER/Golgi-independent (FIG. 26).

Example 19

Construction of FGF-2 Mutagens

Dissection of the contact sites of FGF-2 with the α subunit of $Na^{30}$ /$K^+$ ATPase is pursued by constructing muteins of FGF-2 and assessing the effect of each mutation on export of FGF2.

The initial construct, called pBSSK+FGF-2, is generated by ligating the XhoI fragment containing FGF-2 from pl 8dx into the XhoI site of pBSSK+. Mutagenesis is accomplished using a kit (Chameleon™ Double-Stranded Site-Directed Mutagenesis Kit; Stratagene Cloning Systems, San Diego, Calif.). Briefly, the mutagenic and selection primers are designed to be (a) 25–45 bases long with 10–15 bases on either side of the mutation, (b) have at least a 40% G+C content, and (c) terminate in 1 or more G or C. Primers are phosphorylated and annealed at a 100:1 molar ratio with template DNA by boiling for 5 min, quenching on ice, then incubating at room temperature for 30 min. The primers are extended and ligated using T7 DNA polymerase, T4 DNA ligase and single stranded binding protein. The ligase is heat inactivated and the reaction mix is digested with a restriction enzyme that cuts parental plasmid only (the mutant containing plasmid has abolished the restriction site with the selection primer). The mutant plasmids are transformned into XLmutS competent cells. Transformed cells are grown in liquid culture. DNA from the transformants is recovered and digested again with the selection restriction enzyme. The uncut plasmid is used to transform XLI-Blue competent cells. Approximately 70% or greater colonies contain mutagenized plasmids. Individual colonies are picked, and plasmid DNA isolated. Mutants are verified by restriction digestion and DNA sequence analysis.

The following FGF-2 mutants are constructed:

| | | | | | |
|---|---|---|---|---|---|
| Ser5 → | Val | Glu108 → | Pro, Ala | Ser122 → | Trp |
| Tyr33 → | Ala, Leu | Tyr112 → | Ala | Lys128 → | Asp, Pro |
| Arg53 → | Trp, Ile | Tyr115 → | Ala | Arg129 → | GIu, Leu |
| Ser73 → | Trp, Val, Thr | Ser117 → | Ala | Lys134 → | Thr |
| Cys78 → | Ser | Arg118 → | Ile | Lys144 → | Vaf |
| Cys96 → | Ser | Tyr120 → | Ala | Met151 → | Arg |
| Glu105 → | Pro, Lys | Thr121 → | Pro | Ser152 → | Val, Trp |

A positive clone for each mutant is subcloned back into p18dx via the XhoI site. These clones are expressed in COS cells and assayed by metabolic labeling using $Tran^{35}S$ Label (ICN, Irvine Calif.) as described herein. Results for some of these muteins are presented below.

| Mutation | Changes | Effect of Mutation on Export | Effect of Ouabain on Export |
|---|---|---|---|
| Arg53Trp | CGG/TGG | decrease at 7 hr | decrease |
| Ser73Trp | TCT/TGG | decrease | N.D. |
| Tyr112Ala | TAC/GCC | unstable protein | protein unstable at 7 hr |
| Arg118Ile | AGG/ATC | decrase at 7 hr | decrease |
| Thr121Pro | ACC/CCG | unstable protein | |
| Lys134Thr | AAA/ACC | large decrease at 7 hr | |
| Lys144Val | AAA/GTA | decrease | decrease |
| Cys78Ser | | decrease | N.D. |
| Cys96Ser | | decrease | N.D. |
| Cys78Ser + Cys96Ser | | small increase | decrease |

N.D., not done

In addition, the relative amounts of wild-type FGF-2, some of the muteins found in the intracellular compartament, and some of the exported muteins are presented below. At 7 hours, export of all FGFs is inhibited by ouabain.

| Mutant | 7 hr (−) Ouabain | | 7 hr (+) Ouabain | | ratio 7 hr/0 hr |
|---|---|---|---|---|---|
| | Cells | Media | Cells | Media | Cells |
| 18dx (wt) | 46% | 54% | 82% | 18% | 1.48 |
| Y112/115A | | Unstable | | Unstable | 0 |
| R118I | 47% | 53% | 79% | 21% | 0.45 |
| K144V | 50% | 50% | 70% | 30% | 0.41 |
| 18dx (wt) | 39% | 61% | 50% | 50% | 0.36 |
| R53W | 40% | 60% | 70% | 30% | 0.25 |
| K134T | 53% | 47% | 70% | 30% | 0.26 |
| C78,96S | 42% | 58% | 62% | 38% | 0.68 |

Example 20

CHARACTERIZATION OF P62-FGF2 INTERACTION

Based upon the nucleotide sequence set forth in GenBank Accession No. U46751, p62 was cloned by PCR from polyA selected RNA prepared from HEC-1B cells using the one-step RTPCR kit (cat #2016338, Boehringer). The forward amplification primer was (SEQ ID NO:41):

5'TCCGCCAGCTCGCCG-CTCGCTATGG 3'.

The sequence of the reverse amplification primer was (SEQ ID NO:42):

5'GCACGC-AGAAGAGGTGGGCAAAAGTGGTCA 3'.

The conditions used for RTPCR are 1 cycle 68°; 1 cycle 94° for 2 min; 10 cycles 94° for 30 sec, 68° for 1 min, 70° for 4 min; 30 cycles of 94° for 30 sec, 68° for 1 min, 70° for 5 min. The RTPCR product was TA cloned into pCR3.1 (Invitrogen) and the nucleotide sequenced confirmed. Following transfection, COS cells produce a protein product of the predicted size and immuno reactive to C-terminal anti-peptide immune serum. The peptide sequence used to prepare rabbit immune serum was IQYSKHPPL. Iminunore-activity was also confirmed using commercially available mouse monoclonal antibody from Transduction Laboratory (cat #P65620).

As summarized by the diagram set forth in FIG. 38, to confirm interactions with FGF2 and distinguish cloned from endogenous p62, cDNA clones encoding full length p62 prepared by RTPCR were modified to include an HA epitope tag at the COOH terminus. To do this, the sequence of the forward amplification primer is (SEQ ID NO:44):

5' GCCGGTACCATGGCGTCGC-TCACCGTGAAGGCCTAC 3'

The sequence of the reverse amplification primer is (SEQ ID NO: ):

5'CTGGTACCTCAGGCG-TAGTCGGGCACGTCGTATGGGTACAACG-GCGGGGGATGCTTTGAAT 3'.

The conditions for PCR amplification using the Advantage-GC cDNA PCR kit (Clontech cat # K1907-1) are 1% GC melt, 1 cycle of 94° for 2 min; 30 cycles of 94° for 30 sec, 60° for 1 min, 70° for 2 min; 1 cycle of 70° for 10 min. In order to map FGF2 interaction domains on p62, amplification primers are designed to remove the first 42 amino-terminal amino acids, keeping the COOH-terminal HA epitope tag for detection. The sequence of the forward amplification primer is (SEQ ID NO:45):

5'GCCGGTACCATGGG-ACCCTGCGAGCGGCTGCTGAGC 3' and the sequence of the corresponding reverse amplification primer is (SEQ ID NO:48):

5'CTGGTACCTCAGGCG-TAGTCGGGCACGTCGTATGGGTACAACG-GCGGGGGATGCTTTGAAT 3'.

The conditions for PCR amplification using the Advantage-GC cDNA PCR kit (Clontech cat #K1907-1) are 1% GC melt, 1 cycle of 94° for 2 min; 30 cycles of 94° for 30 sec, 60° for 1 min, 70° for 2 min; 1 cycle of 70' for 10 min. In order to create a COOH-terminal deletion of p62 (removing the last 172 amino acids) blat also containing the HA epitope tag, the sequence of the forward amplification primer is (SEQ ID NO:47):

5'GCCGGTACCAT-GGCGTCGCTCACCGTGAAGGCCTAC 3' and the sequence of the reverse amplification primer is (SEQ ID NO:48):

5'CTGGTACCTCAGGCG-TAGTCGGGCACGTCGTATGGG-TAGGGGGTCAGGCGGCTTCTTTTC 3'.

The conditions for PCR amplification using the Advantage-GC cDNA PCR kit (Clontech cat #K1907–1) are 1% GC melt, 1 cycle of 94° for 2 min; 30 cycles of 94° for 30 sec, 60° for 1 min, 70° for 2 min; 1 cycle of 700 for 10 min.

Transfection of COS and HEC-1B cells (FIG. 36 and 37):

1) 100 mm plates of cells are prepared at $1 \times 10^6$ COS cells or $1.5 \times 10^6$ HEC cells per plate in DMEM+10% FBS. Cells were 40% confluent at the beginning of the experiment.

2) 100 mm plates were transfected with pCR3.1/p62 or pCR3.1/p62HA using the Effectene reagent from Qiagen (cat #301399).

3) Conditions of transfection were as follows:
   a) 2 µg of plasmid was diluted in 250 ul EC buffer and vortexed.
   b) 1 µl of enhancer was added. revortexed and incubated at room temperature for 10 min.
   c) 20 µl of effectene was added, vortexed and incubated 10 min, r.t.
   d) 1 ml of DMEM+10% FBS was added to complete the transfection mixture.
   e) Cells were washed with PBS 2× and incubated in 9 ml DMEM+10% FBS prior to addition of the transaction mixture. Cells were incubated overnight at 37° C.

$^{32}$P labeling of cell cytosol (FIG. 36):

1) One plate of cells was washed 2× in Phosphate free DMEM (3 ml per wash). 5 ml of Phosphate free DMEM was added, incubated 20 min at 37° C.

2) 10 ml of Phosphate free DMEM+5% dialyzed FBS (GibcoBRL) containing 1000 µCi of Ortho$^{32}$P was added. Cell were incubated 4 hrs at 37° C. with occasional rocking.

3) Cells were washed with 2×5ml PBS.

4) Plates of cells were lysed for 30 min at 4° C. by the addition of 5 ml NETN buffer (50 mM Tris pH8, 5mM EDTA, 120 mM NaCl, 1.0% NP-40, protease inhibitor cocktail).
5) Insoluble material was pelleted for 10 min at 14 krpm, 4° C., in the Sorvall microfuge. Supernatant was aliquoted for pull down experiments.

Affinity purification of cell proteins using GST fusion proteins (FIGS. 32–37):
1) To remove the 20% ethanol preservative, glutathione Sepharose 4B (Pharmacia cat #17-0756-01) was washed with 1 ml NETN buffer (50 mM Tris pH8, 5inM EDTA, 120mM NaCl, 1.0% NP-40, protease inhibitor cocktail).
2) 2 μg of GST and GST18 were bound to 20 μl glutathione Sepharose for 20 min on ice then washed with 1 ml NETN. The washed fusion proteins/Sepharose were then added each to 1.4 ml supernatant and bound for 60 min, 4° C. with rocking.
3) Beads were collected by microcentrifugation, then washed 3 times in 1 ml NETN buffer and 2× in ECB buffer (20 mM Tris pH8. 0.2mM EDTA, 150 mM KCl, 0.5% NP-40, 0.05% SDS, 200/0 glycerol, 5 mM DTT before eluting in 40 μl SDS-PAGE sample buffer.

SDS-PAGE of affinity purified proteins (FIGS. 32–37):
1) Solubilized samples were separated by SDS-PAGE on 4–12% acrylamide gradient gels/BisTris purchased from Novex Cat #NP0323. The separating buffer was NuPAGE MES SDS running buffei from Novex Cat #NP0002.
2) The gel was stained with coomassie stain in methanol:acetic acid:dH$_2$O (40:10:50). The gel was submerged in Amplify scintillation enhancer (Amersham cat #NAMP-100) for 20 min.
3) The gel was dried down on Whatman 3 mm paper and exposed by Molecular Dynamics Phosphorimaging analysis and Fuji X-omat film.

Western analysis of GST fusion protein affinity purified p62 proteins (FIGS. 36 and 37):
1) 15 μl SDS-PAGE samples from the affinity purification are run on 4–12% BisTris SDS-PAGE; controls were glutathione Sepharose, GST fusion protein, and Post Nuclear Supernatant (PNS).
2) Proteins were transferred for 1 hr at 25v in Tris/glycine western transfer buffer onto nitrocellulose.
3) Blots were blocked in TBS/5% non-fat dried milk/0.1%NaN$_3$ for 1 hr.
4) 1:1000 dilution of Transduction Labs anti p62 Mab was incubated with the blots in 7 ml TBS/5% non-fat dried milk/0.1% NaN$_3$, in sealed bags overnight.
5) Blots were washed 5× in TBS, 0.1% Tween-20 then incubated for 1 hr in TBS/5% non-fat dried milk/0.1% Tween-20 containing 1:20000 dilution of Goat anti mouse/rabbit HRP conjugated antibody
6) Blots were washed 5× in TBS. 0.1% Tween-20 then exposed to PicoWest Luminol reagent (Pierce) 5 min.
7) Blots were wrapped in plastic wrap and exposed to Fuji X-ray film for various times.

Estimate of p62 bound to GST-18 kDFGF2 based on the above western analysis (FIG. 37):
1.) 1/200$^{th}$ of each of the PNS (post nuclear supernatent) (COS and HECC) were loaded and 1/4$^{th}$ of each of the pull down products. The correction factor for load is thus 1/50 (PNS/pull-down).
2.) For HEC p62 about 4 times the signal was seen in the pull down lane compared to the PNS. Therefore 4×1/50=0.08 or 8% of the p62 bound.
3.) B) For COS p62 about 1/4$^{th}$ the signal was seen in the pull down lane compared to the PNS. Therefore 1/4×1/50=0.005 or 0.5% of the p62 bound.

As shown in FIGS. 36, 37, 38, and 39, transfected COS or HEC cells express p62HA that interacts with GST-FGF2. Although p62HA produced in vitro is not determined to interact with GST-FGF2. This indicates that posttranslation modification of p62 synthesized in vivo may be required for interactions with FGF2. In vivo metabolic labeling with 32P shows that p62 interacting with FGF2 is phosphorylated. The location of potential phosphorylation sites for p62 are shown diagrammatically in FIG. 39. Based upon GenBank Accession No. U46751 for p62 the following posttranslation modifications may be expected as determined using the PROSITE protein analysis algorithm (www.genebio.com) and available from GeneBio (Geneva, Switzerland):

| | |
|---|---|
| Position 21–24 | cAMP phosphorylation site (cAMP/cGMP-dependent) |
| Position 5–7 | protein kinase C phosphorylation site |
| Position 207–209 | protein kinase C phosphorylation site |
| Position 342–344 | protein kinase C phosphorylation site |
| Position 78–81 | casein kinase II phosphorylation site |
| Position 152–155 | casein kinase II phosphorylation site |
| Position 276–279 | casein kinase II phosphorylation site |
| Position 306–309 | casein kinase II phosphorylation site |
| Position 332–335 | casein kinase II phosphorylation site |
| Position 342–345 | casein kinase II phosphorylation site |
| Position 349–352 | casein kinase II phosphorylation site |
| Position 365–363 | casein kinase II phosphorylation site |

Summarizing, according to information shown in FIGS. 36–39, in vivo expression of p62 following transfection of COS or HEC cells compared to synthesis of amino or carboxyl-terminal deletions of p62 in vitro suggest that posttranslation modifications contained within the first 42 amino acids of p62 may be required for interaction with FGF2.

For in vitro transcription/translation the Novagen (cat #70192–3) Single Tube Protein System (STP3) was used as recommended by the manufacturer. The DNA polymerase T7 was used to produce mRNA encoding p62 HA tagged protein domains from clones prepared in the expression vector pCR3.1 (which contains the T7 promoter) as described briefly.

1) 8 μl of STP3/T7 transcription mix was added to 0.5 micrograms of plasmid and incubated 15 min at 30° C.

2) 30 μl of STP3 translation mix was added with 35S-met label and incubated 60 min at 30° C.

3) Reactions were stopped with 1 μl 10 mg/ml RNAse A.

4) Reactions were diluted into NETN and Glutathione Agarose plus GST18 kDFGF2 was added with rocking for 60 min at 4° C.

5) Beads were washed 4× with NETN buffer and solubilized in SDS-PAGE sample buffer.

All patents, patent applications and references referred to herein are incorporated in their entirety. From the foregoing, it will be appreciated that, although specific embodiments of the invention have been described bherein for purposes of illustration, various modifications may be made without deviating from the spirit and scope of the invention. Accordingly, the invention is not limited except as by the appended claims.

We claim:

1. A method for detecting one or more components of a cell transport pathway, comprising:
   (a) contacting cell extracts, cell membranes, or other sub-cellular fractions containing components of a cell transport pathway with a fusion protein of a transport molecule and a tag, wherein the transport molecule comprises a trifunctional protein β subunit, to form a complex of the fusion protein with one or more components of the cell transport pathway;
   (b) isolating the complex; and
   (c) detecting one or more components of the cell transport pathway in the complex.

2. The method of claim 1, wherein one or more components of the cell transport pathway comprise a leaderless protein.

3. The method of claim 2, wherein the leaderless protein comprises FGF-2.

4. The method of claim 2, wherein the leaderless protein comprises IL-1β.

5. The method of claim 1, wherein one or more components of the cell transport pathway comprise a transport molecule.

6. The method of claim 1, wherein the cell extracts or cell membranes containing components of a cell transport pathway are prepared from a cultured cell, wherein the cultured cell is selected from the group consisting of COS-1, BHK, CHO, HeLa, 293, NS-1, HepG2, J744, HEC-1-A, HEC-1-B, 3T3, D10.G4.1, P388D$_1$, 5637, SK-HEP-1, THP-1, Caco-2, MDCK, Jurkat, U87, LnCap, primary tumor biopsies, and other tumor derived cell lines.

7. The method of claim 1, wherein the tag comprises glutathione-S-transferase or fragment thereof that binds glutathione.

8. The method of claim 1, wherein the detecting step comprises denaturing gel electrophoresis.

* * * * *

SEQUENCE LISTING

<160> NUMBER OF SEQ ID NOS: 48

<210> SEQ ID NO 1
<211> LENGTH: 1120
<212> TYPE: DNA
<213> ORGANISM: Homo sapien

<400> SEQUENCE: 1

| | | | | | | |
|---|---|---|---|---|---|---|
| cccgccgcgg | cccggcgggt | gccagattag | cggacgcgtg | cccgcggttg | caacgggatc | 60 |
| ccgggcgctg | cagcttggga | ggcggctctc | cccaggcggc | gtccgcggag | acacccatcc | 120 |
| gtgaacccca | ggtcccgggc | cgccggctcg | ccgcgcaccc | aggggccggc | ggacagaaga | 180 |
| gcggccgagc | ggctcgaggc | tgggggaccg | cgggcgcggc | cgcgcgctgc | cgggcgggag | 240 |
| ggctgggggg | ccggggccgg | ggccgtgccc | cggagcgggt | cggaggccgg | ggccggggcc | 300 |
| ggggggacggc | ggctccccgc | ggcggctcca | gcggctcggg | gatcccggcc | gggccccgca | 360 |
| gggaccatgg | cagccgggag | catcaccacg | ctgcccgcct | tggcccgagg | atggcggcag | 420 |
| cggcggcttc | ccgcccggcc | acttcaagga | ccccaagcgg | ctgtactgca | aaaacggggg | 480 |
| ctttcttcct | gcgcatccac | cccgacggcc | gagttgacgg | ggtccgggag | aagagcgacc | 540 |
| ctcacatcaa | gctacaactt | caaggcagaa | gagagaggag | ttgtgtctat | caaggagtg | 600 |
| tgtgctaacc | gttacctggc | tatgaaggaa | gatggaagat | tactgggctt | ctaaatgtgt | 660 |
| tacggatgag | tgtttctttt | ttgaacgatt | ggaatctaat | aactacaata | cttaccggtc | 720 |
| aaggaaaata | caccagttgg | tatgtggcac | tgaaacgaac | tggcagtat | aaacttggat | 780 |
| ccaaaacagg | acctgggcag | aaagctaata | cttttcttc | caatgtctgc | taagagctga | 840 |
| ttttaatggc | cacatctaat | ctcatttcac | atgaagaag | agtatatttt | ttagaaattt | 900 |
| gttaatgaga | gtaaaagaaa | ataaatgtgt | atagctcagt | ttggataatt | ggtcaaacaa | 960 |
| ttttttatcc | cagtagtaaa | atatgtaacc | attgtcccag | taaagaaaaa | taacaaaagt | 1020 |
| tgtaaaatgt | atattctccc | ttttatattg | gcatctgctg | ttacccagtg | aagcttacct | 1080 |
| agagcatgat | cttttcacgc | atttgcttat | cgaaagagct | | | 1120 |

<210> SEQ ID NO 2
<211> LENGTH: 477
<212> TYPE: DNA
<213> ORGANISM: Homo sapien

<400> SEQUENCE: 2

| | | | | | | |
|---|---|---|---|---|---|---|
| cgcaggacca | tggcagccgg | gagcatcacc | acgctgcccg | ccttgcccga | ggatggcggc | 60 |
| agcggcgcct | tcccgcccgg | ccacttcaag | gaccccaagc | ggctgtactg | caaaaacggg | 120 |
| ggcttcttcc | tgcgcatcca | ccccgacggc | cgagttgacg | gggtccggga | gaagagcgac | 180 |
| cctcacatca | agctacaact | tcaagcagaa | gagagaggag | ttgtgtctat | caaggagtg | 240 |
| tgtgctaacc | gttacctggc | tatgaaggaa | gatggaagat | tactggcttc | taaatgtgtt | 300 |
| acggatgagt | gtttcttttt | tgaacgattg | gaatctaata | actacaatac | ttaccggtca | 360 |
| aggaaataca | ccagttggta | tgtggcactg | aaacgaactg | gcagtataa | acttggatcc | 420 |
| aaaacaggac | ctgggcagaa | agctatactt | tttcttccaa | tgtctgctaa | gagctga | 477 |

<210> SEQ ID NO 3
<211> LENGTH: 155
<212> TYPE: PRT
<213> ORGANISM: Homo sapien

-continued

<400> SEQUENCE: 3

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155
```

<210> SEQ ID NO 4
<211> LENGTH: 351
<212> TYPE: DNA
<213> ORGANISM: Homo sapien

<400> SEQUENCE: 4

```
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
tatcccactc cactaaggtc caagaagacg atgttggtcc aaaagaacgt cacctcagag     240
tccacttgct gtgtagctaa atcatataac agggtcacag taatggggggg tttcaaagtg     300
gagaaccaca cggcgtgcca ctgcagtact tgttattatc acaaatctta a              351
```

<210> SEQ ID NO 5
<211> LENGTH: 116
<212> TYPE: PRT
<213> ORGANISM: Homo sapien

<400> SEQUENCE: 5

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95
```

```
Gly Phe Lys Val Glu Asn His Thr Ala Cys His Cys Ser Thr Cys Tyr
                100                 105                 110
Tyr His Lys Ser
        115

<210> SEQ ID NO 6
<211> LENGTH: 816
<212> TYPE: DNA
<213> ORGANISM: Homo sapien

<400> SEQUENCE: 6
atggccaaag ttccagacat gtttgaagac ctgaagaact gttacagtga aaatgaagaa     60
gacagttcct ccattgatca tctgtctctg aatcagaaat ccttctatca tgtaagctat    120
ggcccactcc atgaaggctg catggatcaa tctgtgtctc tgagtatctc tgaaacctct    180
aaaacatcca agcttacctt caaggagagc atggtggtag tagcaaccaa cgggaaggtt    240
ctgaagaaga gacggttgag tttaagccaa tccatcactg atgatgacct ggaggccatc    300
gccaatgact cagaggaaga aatcatcaag cctaggtcag cacctttag cttcctgagc     360 aatgtgaaat acaactttat gaggatcatc aaatacgaat tcatcctgaa tgacgccctc    420
aatcaaagta taattcgagc caatgatcag tacctcacgg ctgctgcatt acataatctg    480
gatgaagcag tgaatttga catgggtgct ataagtcat caaggatga tgctaaaatt       540 accgtgattc taagaatctc aaaaactcaa ttgtatgtga ctgcccaaga tgaagaccaa    600
ccagtgctgc tgaaggagat gcctgagata cccaaaacca tcacaggtag tgagaccaac    660
ctcctcttct tctgggaaac tcacggcact aagaactatt tcacatcagt tgcccatcca    720
aacttgttta ttgccacaaa gcaagactac tgggtgtgct tggcaggggg gccaccctct    780
atcactgact ttcagatact ggaaaaccag gcgtag                              816

<210> SEQ ID NO 7
<211> LENGTH: 271
<212> TYPE: PRT
<213> ORGANISM: Homo sapien

<400> SEQUENCE: 7

Met Ala Lys Val Pro Asp Met Phe Glu Asp Leu Lys Asn Cys Tyr Ser
  1               5                  10                  15

Glu Asn Glu Glu Asp Ser Ser Ser Ile Asp His Leu Ser Leu Asn Gln
             20                  25                  30

Lys Ser Phe Tyr His Val Ser Tyr Gly Pro Leu His Glu Gly Cys Met
         35                  40                  45

Asp Gln Ser Val Ser Leu Ser Ile Ser Glu Thr Ser Lys Thr Ser Lys
     50                  55                  60

Leu Thr Phe Lys Glu Ser Met Val Val Ala Thr Asn Gly Lys Val
 65                  70                  75                  80

Leu Lys Lys Arg Arg Leu Ser Leu Ser Gln Ser Ile Thr Asp Asp Asp
                 85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
    130                 135                 140

Ile Arg Ala Asn Asp Gln Tyr Leu Thr Ala Ala Ala Leu His Asn Leu
145                 150                 155                 160
```

```
Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
                260                 265                 270

<210> SEQ ID NO 8
<211> LENGTH: 480
<212> TYPE: DNA
<213> ORGANISM: Homo sapien

<400> SEQUENCE: 8
tcagcacctt ttagcttcct gagcaatgtg aaatacaact ttatgaggat catcaaatac      60
gaattcatcc tgaatgacgc cctcaatcaa agtataattc gagccaatga tcagtacctc     120
acggctgctg cattacataa tctggatgaa gcagtgaaat ttgacatggg tgcttataag     180
tcatcaaagg atgatgctaa aattaccgtg attctaagaa tctcaaaaac tcaattgtat     240
gtgactgccc aagatgaaga ccaaccagtg ctgctgaagg agatgcctga gatacccaaa     300
accatcacag gtagtgagac caacctcctc ttcttctggg aaactcacgg cactaagaac     360
tatttcacat cagttgccca tccaaacttg tttattgcca caaagcaaga ctactgggtg     420
tgcttggcag gggggccacc ctctatcact gactttcaga tactggaaaa ccaggcgtag     480

<210> SEQ ID NO 9
<211> LENGTH: 145
<212> TYPE: PRT
<213> ORGANISM: Homo sapien

<400> SEQUENCE: 9

Met Arg Ile Ile Lys Tyr Glu Phe Ile Leu Asn Asp Ala Leu Asn Gln
1               5                   10                  15

Ser Ile Ile Arg Ala Asn Asp Gln Tyr Leu Thr Ala Ala Ala Leu His
            20                  25                  30

Asn Leu Asp Glu Ala Val Lys Phe Asp Met Gly Ala Tyr Lys Ser Ser
        35                  40                  45

Lys Asp Asp Ala Lys Ile Thr Val Ile Leu Arg Ile Ser Lys Thr Gln
    50                  55                  60

Leu Tyr Val Thr Ala Gln Asp Glu Asp Gln Pro Val Leu Leu Lys Glu
65                  70                  75                  80

Met Pro Glu Ile Pro Lys Thr Ile Thr Gly Ser Glu Thr Asn Leu Leu
                85                  90                  95

Phe Phe Trp Glu Thr His Gly Thr Lys Asn Tyr Phe Thr Ser Val Ala
            100                 105                 110

His Pro Asn Leu Phe Ile Ala Thr Lys Gln Asp Tyr Trp Val Cys Leu
        115                 120                 125

Ala Gly Gly Pro Pro Ser Ile Thr Asp Phe Gln Ile Leu Glu Asn Gln
```

```
              130                 135                 140
Ala
145

<210> SEQ ID NO 10
<211> LENGTH: 810
<212> TYPE: DNA
<213> ORGANISM: Homo sapien

<400> SEQUENCE: 10
atggcagaag tacctgagct cgccagtgaa atgatggctt attacagtgg caatgaggat     60
gacttgttct ttgaagctga tggccctaaa cagatgaagt gctccttcca ggacctggac    120
ctctgccctc tggatggcgg catccagcta cgaatctccg accaccacta cagcaagggc    180
ttcaggcagg ccgcgtcagt tgttgtggcc atggacaagc tgaggaagat gctggttccc    240
tgcccacaga ccttccagga gaatgacctg agcaccttct tcccttcat ctttgaagaa     300 gaacctatct tctttgacac atgggataac gaggcttatg tgcacgatgc acctgtacga    360
tcactgaact gcacgctccg ggactcacag caaaaaagct tggtgatgtc tggtccatat    420
gaactgaaag ctctccacct ccagggacag gatatggagc aacaagtggt gttctccatg    480
tcctttgtac aaggagaaga aagtaatgac aaaataccctg tggccttggg cctcaaggaa    540
aagaatctgt acctgtcctg cgtgttgaaa gatgataagc ccactctaca gctggagagt    600
gtagatccca aaattaccc aagaagaag atggaaaagc gatttgtctt caacaagata     660
gaaatcaata acaagctgga atttgagtct gcccagttcc ccaactggta catcagcacc    720
tctcaagcag aaaacatgcc cgtcttcctg ggagggacca aggcggcca ggatataact    780 gacttcacca tgcaatttgt gtcttcctaa                                   810

<210> SEQ ID NO 11
<211> LENGTH: 269
<212> TYPE: PRT
<213> ORGANISM: Homo sapien

<400> SEQUENCE: 11

Met Ala Glu Val Pro Glu Leu Ala Ser Glu Met Met Ala Tyr Tyr Ser
 1               5                  10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160
```

```
Ser Phe Val Gln Gly Glu Glu Ser Asn Asp Lys Ile Pro Val Ala Leu
                165                 170                 175
Gly Leu Lys Glu Lys Asn Leu Tyr Leu Ser Cys Val Leu Lys Asp Asp
            180                 185                 190
Lys Pro Thr Leu Gln Leu Glu Ser Val Asp Pro Lys Asn Tyr Pro Lys
        195                 200                 205
Lys Lys Met Glu Lys Arg Phe Val Phe Asn Lys Ile Glu Ile Asn Asn
    210                 215                 220
Lys Leu Glu Phe Glu Ser Ala Gln Phe Pro Asn Trp Tyr Ile Ser Thr
225                 230                 235                 240
Ser Gln Ala Glu Asn Met Pro Val Phe Leu Gly Gly Thr Lys Gly Gly
                245                 250                 255
Gln Asp Ile Thr Asp Phe Thr Met Gln Phe Val Ser Ser
                260                 265

<210> SEQ ID NO 12
<211> LENGTH: 462
<212> TYPE: DNA
<213> ORGANISM: Homo sapien

<400> SEQUENCE: 12
gcacctgtac gatcactgaa ctgcacgctc cgggactcac agcaaaaaag cttggtgatg      60
tctggtccat atgaactgaa agctctccac ctccagggac aggatatgga gcaacaagtg     120
gtgttctcca tgtcctttgt acaaggagaa gaaagtaatg acaaaatacc tgtggccttg     180
ggcctcaagg aaaagaatct gtacctgtcc tgcgtgttga agatgataa gcccactcta     240 cagctggaga gtgtagatcc caaaaattac ccaaagaaga gatggaaaa gcgatttgtc     300 ttcaacaaga tagaaatcaa taacaagctg gaatttgagt ctgcccagtt ccccaactgg     360
tacatcagca cctctcaagc agaaaacatg cccgtcttcc tgggagggac caaaggcggc     420
caggatataa ctgacttcac catgcaattt gtgtcttcct aa                        462

<210> SEQ ID NO 13
<211> LENGTH: 153
<212> TYPE: PRT
<213> ORGANISM: Homo sapien

<400> SEQUENCE: 13

Ala Pro Val Arg Ser Leu Asn Cys Thr Leu Arg Asp Ser Gln Gln Lys
  1               5                  10                  15
Ser Leu Val Met Ser Gly Pro Tyr Glu Leu Lys Ala Leu His Leu Gln
                20                  25                  30
Gly Gln Asp Met Glu Gln Gln Val Val Phe Ser Met Ser Phe Val Gln
            35                  40                  45
Gly Glu Glu Ser Asn Asp Lys Ile Pro Val Ala Leu Gly Leu Lys Glu
        50                  55                  60
Lys Asn Leu Tyr Leu Ser Cys Val Leu Lys Asp Asp Lys Pro Thr Leu
 65                  70                  75                  80
Gln Leu Glu Ser Val Asp Pro Lys Asn Tyr Pro Lys Lys Lys Met Glu
                85                  90                  95
Lys Arg Phe Val Phe Asn Lys Ile Glu Ile Asn Asn Lys Leu Glu Phe
               100                 105                 110
Glu Ser Ala Gln Phe Pro Asn Trp Tyr Ile Ser Thr Ser Gln Ala Glu
           115                 120                 125
Asn Met Pro Val Phe Leu Gly Gly Thr Lys Gly Gly Gln Asp Ile Thr
       130                 135                 140
```

Asp Phe Thr Met Gln Phe Val Ser Ser
145                 150

<210> SEQ ID NO 14
<211> LENGTH: 454
<212> TYPE: DNA
<213> ORGANISM: Homo sapien

<400> SEQUENCE: 14

| | | | | | |
|---|---|---|---|---|---|
| atggccgagg | gcgaaattac | aacattcacc | gccctcaccg | aaaagtttaa | tctgcctccc | 60 |
| gggaattaca | agaagcccaa | actcctctac | tgcagcaacg | ggggccactt | cctgaggatt | 120 |
| cttccggatg | gcacagtgga | tgggacaagg | gacaggagcc | gaccagcaca | ttcagctgca | 180 |
| actcagtgcg | gaaagcgtgg | gggaggtgta | tataaagagt | accgagactg | gccagtactt | 240 |
| tggcaatgga | caccgacggg | cttttatacg | gctcacagac | accaaatgag | gaatgtttgt | 300 |
| tcctggaaag | gctggaggag | aaaccattac | aacacctata | tatccaagaa | gcatgcagag | 360 |
| aagaattggt | ttgttggcct | caagcggtcc | tcggactcac | tatggccaga | aagcaatctt | 420 |
| gtttctcccc | ctgccagtct | cttctgatta | ataa | | | 454 |

<210> SEQ ID NO 15
<211> LENGTH: 156
<212> TYPE: PRT
<213> ORGANISM: Homo sapien

<400> SEQUENCE: 15

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Tyr
65                  70                  75                  80

Leu Ala Met Asp Thr Asp Gly Leu Leu Tyr Gly Ser Gln Thr Pro Asn
                85                  90                  95

Glu Glu Cys Leu Phe Leu Glu Arg Leu Glu Glu Asn His Tyr Asn Thr
            100                 105                 110

Tyr Ile Ser Lys Lys His Ala Glu Lys Asn Trp Phe Val Gly Leu Lys
        115                 120                 125

Lys Asn Gly Ser Cys Lys Arg Gly Pro Arg Thr His Tyr Gly Gln Lys
    130                 135                 140

Ala Ile Leu Phe Leu Pro Leu Pro Val Ser Ser Asp
145                 150                 155

<210> SEQ ID NO 16
<211> LENGTH: 221
<212> TYPE: DNA
<213> ORGANISM: Homo sapien

<400> SEQUENCE: 16

| | | | | | |
|---|---|---|---|---|---|
| atggaaccgg | tcgacccgcg | tctggaacca | tggaaacacc | ccgggtccca | gccgaaaacc | 60 |
| gcgtgcacca | actgctactt | gcaaaaaatg | ctgcttccac | tgccaggttt | gcttcatcac | 120 |
| caaagcccta | ggtatctctt | acggccgtaa | aaaacgtcgt | tcagcgacgt | cgtccgccgc | 180 |

```
aggggatccca gacccaccag gtttctctgt ctaaacagtg a                    221
```

<210> SEQ ID NO 17
<211> LENGTH: 72
<212> TYPE: PRT
<213> ORGANISM: Homo sapien

<400> SEQUENCE: 17

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln
65                  70
```

<210> SEQ ID NO 18
<211> LENGTH: 263
<212> TYPE: DNA
<213> ORGANISM: Homo sapien

<400> SEQUENCE: 18

```
atggaaccag tcgaccctag actggaaccg tggaaacacc cgggttccca gccgaaaact    60
gcatgcacca actgttactg taaaaagtgt tgcttccact gtcaagtttg tttcatcacc   120
aaggctttgg gtatctccta cggtcgtaag aaacgtagaa cagcgcagac gtccaccgca   180
aggttctcag actcatcaag tttccttgtc caagcaaccg acctcccaat ctcgcggtga   240
acccgacagg tcctaaggaa tag                                          263
```

<210> SEQ ID NO 19
<211> LENGTH: 86
<212> TYPE: PRT
<213> ORGANISM: Homo sapien

<400> SEQUENCE: 19

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85
```

<210> SEQ ID NO 20
<211> LENGTH: 31
<212> TYPE: DNA
<213> ORGANISM: Artificial Sequence
<220> FEATURE:
<223> OTHER INFORMATION: PCR Primer

<400> SEQUENCE: 20

```
aaggacagaa gcggccgcgg gaccatggca g                              31
```

<210> SEQ ID NO 21
<211> LENGTH: 39
<212> TYPE: DNA
<213> ORGANISM: Artificial Sequence
<220> FEATURE:
<223> OTHER INFORMATION: PCR Primer

<400> SEQUENCE: 21

```
aaggacagaa gcggccgctc agctcttagc agccattgg                      39
```

<210> SEQ ID NO 22
<211> LENGTH: 75
<212> TYPE: DNA
<213> ORGANISM: Artificial Sequence
<220> FEATURE:
<223> OTHER INFORMATION: PCR Primer

<400> SEQUENCE: 22

```
ctagggatcc accatggccg agggcgaaat tacaacattc accgccctca ccgaaaagtt    60
taatctgcct cccgg                                                     75
```

<210> SEQ ID NO 23
<211> LENGTH: 31
<212> TYPE: DNA
<213> ORGANISM: Artificial Sequence
<220> FEATURE:
<223> OTHER INFORMATION: PCR Primer

<400> SEQUENCE: 23

```
gatcgaattc tcaatcagaa gaagctggca g                              31
```

<210> SEQ ID NO 24
<211> LENGTH: 14
<212> TYPE: PRT
<213> ORGANISM: Artificial Sequence
<220> FEATURE:
<223> OTHER INFORMATION: N-terminal amino acid sequence recreated by the
      forward primer for wild type FGF-1

<400> SEQUENCE: 24

```
Ala Glu Gly Glu Ile Thr Thr Phe Thr Ala Leu Thr Glu Lys
 1               5                  10
```

<210> SEQ ID NO 25
<211> LENGTH: 59
<212> TYPE: DNA
<213> ORGANISM: Artificial Sequence
<220> FEATURE:
<223> OTHER INFORMATION: PCR Primer

<400> SEQUENCE: 25

```
ctagtctaga tcaggcgtag tcgggcacgt cgtatgggta atcagaagag actggcagg    59
```

<210> SEQ ID NO 26
<211> LENGTH: 61
<212> TYPE: DNA
<213> ORGANISM: Artificial Sequence
<220> FEATURE:
<223> OTHER INFORMATION: PCR Primer

<400> SEQUENCE: 26

```
gatcgaattc tcacttgtca tcgtcgtcct tgtcgtcacg cgtatcagaa gagactggca    60
```

```
<210> SEQ ID NO 27
<211> LENGTH: 29
<212> TYPE: DNA
<213> ORGANISM: Artificial Sequence
<220> FEATURE:
<223> OTHER INFORMATION: PCR Primer

<400> SEQUENCE: 27
ctagggatcc accatggaac cagtcgacc                                29

<210> SEQ ID NO 28
<211> LENGTH: 31
<212> TYPE: DNA
<213> ORGANISM: Artificial Sequence
<220> FEATURE:
<223> OTHER INFORMATION: PCR Primer

<400> SEQUENCE: 28
gatcgaattc tcattcctta ggacctgtcg g                             31

<210> SEQ ID NO 29
<211> LENGTH: 58
<212> TYPE: DNA
<213> ORGANISM: Artificial Sequence
<220> FEATURE:
<223> OTHER INFORMATION: PCR Primer

<400> SEQUENCE: 29
ctagtctaga tcaggcgtag tcgggcacgt cgtatgggta ttccttagga cctgtcgg    58

<210> SEQ ID NO 30
<211> LENGTH: 30
<212> TYPE: DNA
<213> ORGANISM: Artificial Sequence
<220> FEATURE:
<223> OTHER INFORMATION: PCR Primer

<400> SEQUENCE: 30
ctaggaattc agatcactgt ttagacagag                               30

<210> SEQ ID NO 31
<211> LENGTH: 56
<212> TYPE: DNA
<213> ORGANISM: Artificial Sequence
<220> FEATURE:
<223> OTHER INFORMATION: PCR primer

<400> SEQUENCE: 31
ctgagaattc tcacttgtca tcgtcgtcct tgtagtcctg tttagacaga gaaacc      56

<210> SEQ ID NO 32
<211> LENGTH: 61
<212> TYPE: DNA
<213> ORGANISM: Artificial Sequence
<220> FEATURE:
<223> OTHER INFORMATION: PCR primer

<400> SEQUENCE: 32
ctgagaattc tcaggcgtag tcgggcacgt cgtatgggta ctgtttagac agagaaacct  60
g                                                              61

<210> SEQ ID NO 33
<211> LENGTH: 37
```

```
<212> TYPE: DNA
<213> ORGANISM: Artificial Sequence
<220> FEATURE:
<223> OTHER INFORMATION: PCR primer

<400> SEQUENCE: 33
ctagggatcc accatgagga tcatcaaata cgaattc                              37

<210> SEQ ID NO 34
<211> LENGTH: 34
<212> TYPE: DNA
<213> ORGANISM: Artificial Sequence
<220> FEATURE:
<223> OTHER INFORMATION: PCR primer

<400> SEQUENCE: 34
gcacttctcg agctacgcct ggttttccag tatc                                 34

<210> SEQ ID NO 35
<211> LENGTH: 8
<212> TYPE: PRT
<213> ORGANISM: Artificial Sequence
<220> FEATURE:
<223> OTHER INFORMATION: flg peptide tag

<400> SEQUENCE: 35

Asp Tyr Lys Asp Asp Asp Asp Lys
 1               5

<210> SEQ ID NO 36
<211> LENGTH: 9
<212> TYPE: PRT
<213> ORGANISM: Artificial Sequence
<220> FEATURE:
<223> OTHER INFORMATION: influenza haernagglutinin peptide tag

<400> SEQUENCE: 36

Tyr Pro Tyr Asp Val Pro Asp Tyr Ala
 1               5

<210> SEQ ID NO 37
<211> LENGTH: 31
<212> TYPE: DNA
<213> ORGANISM: Artificial Sequence
<220> FEATURE:
<223> OTHER INFORMATION: PCR primer

<400> SEQUENCE: 37
gcgtggatcc gcagaagtac ctgagctcgc c                                    31

<210> SEQ ID NO 38
<211> LENGTH: 33
<212> TYPE: DNA
<213> ORGANISM: Artificial Sequence
<220> FEATURE:
<223> OTHER INFORMATION: PCR primer

<400> SEQUENCE: 38
atgtcccggg ttaggaagac acaaattgca tgg                                  33

<210> SEQ ID NO 39
<211> LENGTH: 31
<212> TYPE: DNA
<213> ORGANISM: Artificial Sequence
<220> FEATURE:
<223> OTHER INFORMATION: PCR primer
```

```
<400> SEQUENCE: 39
gcgtggatcc gatgcacctg tacgatcact g                              31

<210> SEQ ID NO 40
<211> LENGTH: 33
<212> TYPE: DNA
<213> ORGANISM: Artificial Sequence
<220> FEATURE:
<223> OTHER INFORMATION: PCR primer

<400> SEQUENCE: 40
atgtcccggg ttaggaagac acaaattgca tgg                            33

<210> SEQ ID NO 41
<211> LENGTH: 25
<212> TYPE: DNA
<213> ORGANISM: Artificial Sequence
<220> FEATURE:
<223> OTHER INFORMATION: PCR primer

<400> SEQUENCE: 41
tccgccagct cgccgctcgc tatgg                                     25

<210> SEQ ID NO 42
<211> LENGTH: 30
<212> TYPE: DNA
<213> ORGANISM: Artificial Sequence
<220> FEATURE:
<223> OTHER INFORMATION: PCR primer

<400> SEQUENCE: 42
gcacgcagaa gaggtgggca aaagtggtca                                30

<210> SEQ ID NO 43
<211> LENGTH: 36
<212> TYPE: DNA
<213> ORGANISM: Artificial Sequence
<220> FEATURE:
<223> OTHER INFORMATION: PCR primer

<400> SEQUENCE: 43
gccggtacca tggcgtcgct caccgtgaag gcctac                         36

<210> SEQ ID NO 44
<211> LENGTH: 61
<212> TYPE: DNA
<213> ORGANISM: Artificial Sequence
<220> FEATURE:
<223> OTHER INFORMATION: PCR primer

<400> SEQUENCE: 44
ctggtacctc aggcgtagtc gggcacgtcg tatgggtaca acggcggggg atgctttgaa    60
t                                                                   61

<210> SEQ ID NO 45
<211> LENGTH: 36
<212> TYPE: DNA
<213> ORGANISM: Artificial Sequence
<220> FEATURE:
<223> OTHER INFORMATION: PCR primer

<400> SEQUENCE: 45
gccggtacca tgggaccctg cgagcggctg ctgagc                         36
```

```
<210> SEQ ID NO 46
<211> LENGTH: 61
<212> TYPE: DNA
<213> ORGANISM: Artificial Sequence
<220> FEATURE:
<223> OTHER INFORMATION: PCR primer

<400> SEQUENCE: 46
ctggtacctc aggcgtagtc gggcacgtcg tatgggtaca acggcggggg atgctttgaa        60
t                                                                         61

<210> SEQ ID NO 47
<211> LENGTH: 36
<212> TYPE: DNA
<213> ORGANISM: Artificial Sequence
<220> FEATURE:
<223> OTHER INFORMATION: PCR primer

<400> SEQUENCE: 47
gccggtacca tggcgtcgct caccgtgaag gcctac                                    36

<210> SEQ ID NO 48
<211> LENGTH: 60
<212> TYPE: DNA
<213> ORGANISM: Artificial Sequence
<220> FEATURE:
<223> OTHER INFORMATION: PCR primer

<400> SEQUENCE: 48
ctggtacctc aggcgtagtc gggcacgtcg tatgggtagg gggtcaggcg gcttctttc          60
```